United States Patent
Jackson et al.

(10) Patent No.: US 12,195,557 B2
(45) Date of Patent: Jan. 14, 2025

(54) OPTIMISED COMPOUNDS

(71) Applicant: AXELIA ONCOLOGY PTY LTD, Melbourne (AU)

(72) Inventors: David Jackson, Melbourne (AU); Ian Holmes, Melbourne (AU); Weiguang Zeng, Melbourne (AU); Christophe Demaison, Melbourne (AU)

(73) Assignee: AXELIA ONCOLOGY PTY LTD, Melbourne (AU)

( * ) Notice: Subject to any disclaimer, the term of this patent is extended or adjusted under 35 U.S.C. 154(b) by 257 days.

(21) Appl. No.: 16/768,341

(22) PCT Filed: Dec. 21, 2018

(86) PCT No.: PCT/AU2018/051397
§ 371 (c)(1),
(2) Date: May 29, 2020

(87) PCT Pub. No.: WO2019/119067
PCT Pub. Date: Jun. 27, 2019

(65) Prior Publication Data
US 2021/0230217 A1    Jul. 29, 2021

(30) Foreign Application Priority Data

Dec. 21, 2017 (AU) ................................ 2017905128
Mar. 29, 2018 (AU) ................................ 2018901056
Sep. 25, 2018 (AU) ................................ 2018903597

(51) Int. Cl.
| | | |
|---|---|---|
| C07K 5/062 | (2006.01) |
| A61K 38/00 | (2006.01) |
| A61K 47/54 | (2017.01) |
| A61K 47/60 | (2017.01) |
| A61P 11/00 | (2006.01) |
| C07C 317/48 | (2006.01) |
| C07C 323/60 | (2006.01) |

(52) U.S. Cl.
CPC .......... *C07K 5/0606* (2013.01); *A61K 47/542* (2017.08); *A61K 47/60* (2017.08); *A61P 11/00* (2018.01); *C07C 317/48* (2013.01); *C07C 323/60* (2013.01); *A61K 38/00* (2013.01)

(58) Field of Classification Search
None
See application file for complete search history.

(56) References Cited

U.S. PATENT DOCUMENTS

| | | |
|---|---|---|
| 7,316,996 B2 | 1/2008 | Muhlradt et al. |
| 8,883,174 B2 | 11/2014 | Dickey et al. |
| 8,986,700 B2 | 3/2015 | Jackson et al. |
| 9,089,508 B2 | 7/2015 | Jackson et al. |
| 9,676,819 B2 | 6/2017 | Jackson et al. |
| 9,889,195 B2 | 2/2018 | Jackson et al. |
| 10,406,100 B2 | 9/2019 | Jackson et al. |
| 11,351,114 B2 | 6/2022 | Jackson et al. |
| 2004/0191270 A1 | 9/2004 | Drane et al. |
| 2007/0066534 A1 | 3/2007 | Jackson et al. |
| 2008/0069831 A1 | 3/2008 | Duke et al. |
| 2008/0069832 A1 | 3/2008 | Chomez et al. |
| 2009/0257980 A1 | 10/2009 | Davies et al. |
| 2010/0129385 A1 | 5/2010 | Jackson et al. |
| 2010/0310595 A1 | 12/2010 | Jackson et al. |
| 2011/0280899 A1 | 11/2011 | Jackson et al. |
| 2012/0064109 A1 | 3/2012 | Jackson et al. |
| 2013/0230544 A1 | 9/2013 | Jackson et al. |
| 2015/0150966 A1 | 6/2015 | Jackson et al. |
| 2019/0380952 A1 | 12/2019 | Jackson et al. |
| 2020/0147028 A1* | 5/2020 | Bartlett .................. A61K 39/12 |
| 2021/0177795 A1* | 6/2021 | Jackson .................. A61P 31/16 |
| 2022/0347146 A1 | 11/2022 | Demaison et al. |
| 2022/0388950 A1 | 12/2022 | Holmes et al. |
| 2023/0043518 A1 | 2/2023 | Demaison et al. |
| 2023/0226004 A1 | 7/2023 | Tsitoura et al. |
| 2023/0257345 A1 | 8/2023 | Holmes et al. |
| 2023/0278954 A1 | 9/2023 | McLachlan |

FOREIGN PATENT DOCUMENTS

| | | |
|---|---|---|
| AU | 2014202674 A1 | 6/2014 |
| EP | 1550458 A1 | 7/2005 |
| EP | 1666056 A1 | 6/2006 |
| EP | 3728289 A1 | 10/2020 |
| JP | 2016-216593 A | 12/2016 |
| WO | WO-2001/037869 A1 | 5/2001 |
| WO | WO-2001/090129 A2 | 11/2001 |
| WO | WO-2004/014956 A1 | 2/2004 |
| WO | WO-2004/014957 A1 | 2/2004 |

(Continued)

OTHER PUBLICATIONS

Tan et al. "Intranasal Administration of the TLR2 Agonist Pam2Cys Provides Rapid Protection against Influenza in Mice" Molecular Pharmaceutics 9:2710-2718 (Year: 2012).*
Beaumont et al. "Design of Ester Prodrugs to Enhance Oral Absorption of Poorly Permeable Compounds: Challenges to the Discovery Scientist" Current Drug Metabolism 4:461-485. (Year: 2003).*
Ettmayer et al. "Lessons Learned from Marketed and Investigational Prodrugs" J. Med. Chem. 47:2393-2404. (Year: 2004).*
Han H "Targeted Prodrug Design to Optimize Drug Delivery" AAPS Pharmsci 2:Article 6 (Year: 2000).*

(Continued)

*Primary Examiner* — Sudhakar Katakam
*Assistant Examiner* — Zachary J Miknis
(74) *Attorney, Agent, or Firm* — McCarter & English, LLP; Michael J. DeGrazia

(57) ABSTRACT

The present invention relates to TLR2 agonist compounds and their compositions, and the use of such compounds and compositions in the prevention and/or treatment of respiratory infections, or diseases or conditions associated with viral or bacterial infections.

5 Claims, 16 Drawing Sheets

(56) References Cited

FOREIGN PATENT DOCUMENTS

| WO | WO-2005/070959 A2 | 8/2005 | | |
|---|---|---|---|---|
| WO | 2005/079419 A2 | 9/2005 | | |
| WO | WO-2005/112991 A2 | 12/2005 | | |
| WO | WO-2006/069262 A2 | 6/2006 | | |
| WO | WO-2006/084319 A1 | 8/2006 | | |
| WO | WO-2006/091591 A1 | 8/2006 | | |
| WO | 2007/059931 A1 | 5/2007 | | |
| WO | WO-2007/103322 A2 | 9/2007 | | |
| WO | WO-2008/085549 A2 | 7/2008 | | |
| WO | WO-2009/046498 A1 | 4/2009 | | |
| WO | 2009/137103 A2 | 11/2009 | | |
| WO | WO-2009/155332 A1 | 12/2009 | | |
| WO | WO-2010/028246 A2 | 3/2010 | | |
| WO | WO-2010/093436 A2 | 8/2010 | | |
| WO | WO-2010/111485 A1 | 9/2010 | | |
| WO | WO-2010/115229 A1 | 10/2010 | | |
| WO | WO-2010/115230 A1 | 10/2010 | | |
| WO | WO-2010/128303 A1 | 11/2010 | | |
| WO | WO-2011/080259 A1 | 7/2011 | | |
| WO | WO-2011119759 A1 * | 9/2011 | ............. | A61K 31/17 |
| WO | 2012/037612 A1 | 3/2012 | | |
| WO | WO-2013/049941 A1 | 4/2013 | | |
| WO | WO-2014/207708 A2 | 12/2014 | | |
| WO | 2016/037240 A1 | 3/2016 | | |
| WO | WO-2016/044839 A2 | 3/2016 | | |
| WO | WO-2017/019896 A1 | 2/2017 | | |
| WO | WO-2017/145097 A2 | 8/2017 | | |
| WO | 2018/176099 A1 | 10/2018 | | |
| WO | 2018/197582 A1 | 11/2018 | | |
| WO | WO-2019/043604 A1 | 3/2019 | | |
| WO | 2019/119069 A1 | 6/2019 | | |
| WO | 2021/042171 A1 | 3/2021 | | |

OTHER PUBLICATIONS

Muller C "Prodrug Approaches for Enhancing the Bioavailability of Drugs with Low Solubility" Chemistry & Biodiversity 6:2071-2083 (Year: 2009).*
Singh et al. "Recent Trends in Targeted Anticancer Prodrug and Conjugate Design" Curr. Med. Chem. 15:1802-1826. (Year: 2008).*
Testa B "Prodrug research: futile or fertile?" Biochem. Pharmacol. 68:2097-2106. (Year: 2004).*
Contoli et al., Viral infections in exacerbations of asthma and chronic obstructive pulmonary disease. Minerva Med. Dec. 2009;100(6):467-78.
Richard et al., TLR2 signaling decreases transmission of *Streptococcus pneumoniae* by limiting bacterial shedding In an infant mouse Influenza A co-infection model. PLoS Pathog. 2014;10(8):e1004339, 9 pages.
Tan et al., Intranasal administration of the TLR2 agonist Pam2Cys provides rapid protection against influenza in mice. Mol Pharm. 2012;9(9):2710-2718.
Voss et al., The activity of lipopeptide TLR2 agonists critically depends on the presence of solubilizers. Eur J Immunol. Dec. 2007;37(12):3489-98.
International Search Report and Written Opinion for Application No. PCT/AU2018/050295, dated May 23, 2018, 10 pages.
International Search Report and Written Opinion for Application No. PCT/AU2018/051397, dated Feb. 28, 2019, 16 pages.
International Search Report and Written Opinion for Application No. PCT/AU2018/051401, dated Feb. 12, 2019, 13 pages.
Akazawa, Development of a Functionally Designed Artificial Adjuvant. Research Report of the Uehara Memorial Foundation 23. 12 pages, (2009).
Alexopoulou et al., Recognition of double-stranded RNA and activation of NF-kappaB by Toll-like receptor 3. Nature. Oct. 18, 2001;413(6857):732-8.
Alphs et al., Protection against heterologous human papillomavirus challenge by a synthetic lipopeptide vaccine containing a broadly cross-neutralizing epitope of L2. Proc Natl Acad Sci U S A. Apr. 15, 2008;105(15):5850-5.
Amigorena, Fc gamma receptors and cross-presentation in dendritic cells. J Exp Med. Jan. 7, 2002;195(1):F1-3.
Andra et al., Enhancement of endotoxin neutralization by coupling of a C12-alkyl chain to a lactoferricin-derived peptide. Biochem J. Jan. 1, 2005;385(Pt 1):135-43.
Archer et al., MyD88-dependent responses involving toll-like receptor 2 are important for protection and clearance of Legionella pneumophila in a mouse model of Legionnaires' disease. Infect Immun. Jun. 2006;74(6):3325-33.
Asea et al., Novel signal transduction pathway utilized by extracellular HSP70: role of toll-like receptor (TLR) 2 and TLR4. J Biol Chem. Apr. 26, 2002;277(17):15028-34.
Azuma et al., The peptide sequence of diacyl lipopeptides determines dendritic cell TLR2- mediated NK activation. PLoS One. Sep. 2, 2010;5(9):e12550, 12 pages.
Basto et al., Targeting TLR2 for vaccine development. J Immunol Res. 2014;2014:619410, 22 pages.
Baz et al., Branched and linear lipopeptide vaccines have different effects on primary CD4+ and CD8+ T-cell activation but induce similar tumor-protective memory CD8+ T-cell responses. Vaccine. May 19, 2008;26(21):2570-9.
Belz et al., A previously unrecognized H-2D(b)-restricted peptide prominent in the primary influenza A virus-specific CD8(+) T-cell response is much less apparent following secondary challenge. J Virol. Apr. 2000;74(8):3486-93.
Bodmer et al., Enhanced recognition of a modified peptide antigen by cytotoxic T cells specific for influenza nucleoprotein. Cell. Jan. 29, 1988;52(2): 3486-3493.
Brown et al., Immune recognition. A new receptor for beta-glucans. Nature. Sep. 6, 2001;413(6851):36-7.
Bulut et al., Chlamydial heat shock protein 60 activates macrophages and endothelial cells through Toll-like receptor 4 and MD2 in a MyD88-dependent pathway. J Immunol. Feb. 1, 2002;168(3):1435-40.
Buwitt-Beckmann et al., TLR1- and TLR6-independent recognition of bacterial lipopeptides. J Biol Chem. Apr. 7, 2006;281(14):9049-57.
Buwitt-Beckmann et al., Toll-like receptor 6-independent signaling by diacylated lipopeptides. Eur J Immunol. Jan. 2005;35(1):282-9.
Chaturvedi et al., A review on mucoadhesive polymer used in nasal drug delivery system. J Adv Pharm Technol Res. Oct. 2011;2(4):215-22.
Cheng et al., Characterization of nasal spray pumps and deposition pattern in a replica of the human nasal airway. J Aerosol Med. 2001 Summer; 14(2):267-80.
Chow et al., Toll-like receptor-4 mediates lipopolysaccharide-induced signal transduction. J Biol Chem. Apr. 16, 1999;274(16):10689-92.
Chua et al., A Self-adjuvanting Lipopeptide Vaccine for Immunotherapy of Hepatitis C Virus Infection Activates Dendritic Cells and Induces Antigen-Specific T Cell Responses. J Hepat. 2008;48:S236-S237, Abstract 635.
Chua et al., Comparison of lipopeptide-based immunocontraceptive vaccines containing different lipid groups. Vaccine. Jan. 2, 2007;25(1):92-101.
Chua et al., Dendritic cell acquisition of epitope cargo mediated by simple cationic peptide structures. Peptides. Jun. 2008;29(6):881-90.
Chua et al., Soluble proteins induce strong CD8+ T cell and antibody responses through electrostatic association with simple cationic or anionic lipopeptides that target TLR2. J Immunol. Aug. 15, 2011;187(4):1692-701.
Chua et al., The use of a TLR2 agonist-based adjuvant for enhancing effector and memory CD8 T-cell responses. Immunol Cell Biol. Apr. 2014;92(4):377-83.
Cleret et al., Lung dendritic cells rapidly mediate anthrax spore entry through the pulmonary route. J Immunol. Jun. 15, 2007;178(12):7994-8001.
Cluff et al., Synthetic toll-like receptor 4 agonists stimulate innate resistance to infectious challenge. Infect Immun. May 2005;73(5):3044-52.

(56) References Cited

OTHER PUBLICATIONS

Deliyannis et al., Intranasal lipopeptide primes lung-resident memory CD8+ T cells for long-term pulmonary protection against influenza. Eur J Immunol. Mar. 2006;36(3):770-780.
Dikopoulos et al., Novel peptide-based vaccines efficiently prime murine "help"—independent CD8+ T cell responses in the liver. Hepatology. Aug. 2004;40(2):300-9.
Djupesland, Nasal drug delivery devices: characteristics and performance in a clinical perspective-a review. Drug Deliv Transl Res. Feb. 2013;3(1):42-62.
Duggan et al., Synergistic interactions of TLR2/6 and TLR9 induce a high level of resistance to lung infection in mice. J Immunol. May 15, 2011;186(10):5916-26.
Engering et al., The mannose receptor functions as a high capacity and broad specificity antigen receptor in human dendritic cells. Eur J Immunol. Sep. 1997;27(9):2417-25.
Farley et al., Lipopolysaccharide structure determines ionic and hydrophobic binding of a cationic antimicrobial neutrophil granule protein. Infect Immun. Jun. 1988;56(6):1589-92.
Feinberg et al., Structural basis for selective recognition of oligosaccharides by DC-SIGN and DC-SIGNR. Science. Dec. 7, 2001;294(5549):2163-6.
Firat et al., H-2 class I knockout, HLA-A2.1-transgenic mice: a versatile animal model for preclinical evaluation of antitumor immunotherapeutic strategies. Eur J Immunol. Oct. 1999;29(10):3112-21.
Frison et al., Oligolysine-based oligosaccharide clusters: selective recognition and endocytosis by the mannose receptor and dendritic cell-specific intercellular adhesion molecule 3 (ICAM-3)-grabbing nonintegrin. J Biol Chem. Jun. 27, 2003;278(26):23922-9.
Fujimoto et al., Virus clearance through apoptosis-dependent phagocytosis of influenza A virus-infected cells by macrophages. J Virol. Apr. 2000;74(7):3399-403.
Fuse et al., Role of Toll-like receptor 2 in recognition of Legionella pneumophila in a murine pneumonia model. J Med Microbiol. Mar. 2007;56(Pt 3):305-312.
Futaki et al., Arginine-rich peptides. An abundant source of membrane-permeable peptides having potential as carriers for intracellular protein delivery. J Biol Chem. Feb. 23, 2001;276(8):5836-40.
Gariepy et al., Vectorial delivery of macromolecules into cells using peptide-based vehicles. Trends Biotechnol. Jan. 2001;19(1):21-8.
Ghielmetti et al., Synthetic bacterial lipopeptide analogs facilitate naive CD4+ T cell differentiation and enhance antigen-specific HLA-II-restricted responses. Eur J Immunol. Aug. 2005;35(8):2434-42.
Gianfrani et al., Human memory CTL response specific for influenza A virus is broad and Multispecific. Hum Immunol. May 2000;61(5):438-52.
Gonzalez-Juarrero et al., Dynamics of macrophage cell populations during murine pulmonary tuberculosis. J Immunol. Sep. 15, 2003;171(6):3128-35.
Gotch et al., Cytotoxic T lymphocytes recognize a fragment of influenza virus matrix protein in association with HLA-A2. Nature. Apr. 30, 1987-May 6;326(6116):881-2.
Gratton et al., Cell-permeable peptides improve cellular uptake and therapeutic gene delivery of replication-deficient viruses in cells and in vivo. Nat Med. Mar. 2003;9(3):357-62.
Gros et al., A non-covalent peptide-based strategy for protein and peptide nucleic acid transduction. Biochim Biophys Acta. Mar. 2006;1758(3):384-93.
Guo et al., The Novel Toll-Like Receptor 2 Agonist SUP3 Enhances Antigen Presentation and T Cell Activation by Dendritic Cells. Front Immunol. Feb. 21, 2017;8:158, 15 pages.
Hayashi et al., The innate immune response to bacterial flagellin is mediated by Toll-like receptor 5. Nature. Apr. 26, 2001;419(6832):1099-103.
Heil et al., pecies-specific recognition of single-stranded RNA via toll-like receptor 7 and 8. Science. Mar. 5, 2004;303(5663):1526-9.
Hemmi et al., A Toll-like receptor recognizes bacterial DNA. Nature. Dec. 7, 2000;408(6813):740-5.
Hemmi et al., Small anti-viral compounds activate immune cells via the TLR7 MyD88-dependent signaling pathway. Nat Immunol. Feb. 2002;3(2):196-200.
Heuking et al., Stimulation of human macrophages (THP-1) using Toll-like receptor-2 (TLR-2) agonist decorated nanocarriers. J Drug Target. Sep. 2009;17(8):662-70.
Hoffmann et al., Induction of tumor cytotoxicity in murine bone marrow-derived macrophages by two synthetic lipopeptide analogues. Biol Chem Hoppe Seyler. Jun. 1989;370(6):575-82.
Huynh et al., Novel toll-like receptor 2 ligands for targeted pancreatic cancer imaging and immunotherapy. J Med Chem. Nov. 26, 2012;55(22):9751-62.
Ismaili et al., Monophosphoryl lipid A activates both human dendritic cells and T cells. J Immunol. Jan. 15, 2002;168(2):926-32.
Iwabuchi et al., Effects of intranasal administration of Bifidobacterium longum BB536 on mucosal immune system in respiratory tract and influenza virus infection in mice. Milk Science. 2009;58(3):129-133.
Jackson et al., A totally synthetic vaccine of generic structure that targets Toll-like receptor 2 on dendritic cells and promotes antibody or cytotoxic T cell responses. Proc Natl Acad Sci U S A. Oct. 26, 2004;101(43):15440-5.
Jameson et al., Human CD8+ and CD4+ T lymphocyte memory to influenza A viruses of swine and avian species. J Immunol. Jun. 15, 1999;162(12):7578-83.
Kang et al., Recognition of lipopeptide patterns by Toll-like receptor 2-Toll-like receptor 6 heterodimer. Immunity. Dec. 18, 2009;31(6):873-84.
Kawamura et al., Probing the impact of valency on the routing of arginine-rich peptides into eukaryotic cells. Biochemistry. Jan. 31, 2006;45(4):1116-27.
Kery et al., Ligand recognition by purified human mannose receptor. Arch Biochem Biophys. Oct. 1992;298(1):49-55.
Khong et al., Adjuvants for peptide-based cancer vaccines. J Immunother Cancer. Sep. 20, 2016;4:56, 11 pages.
Kutzler et al., Developing DNA vaccines that call to dendritic cells. J Clin Invest. Nov. 2004;114(9):1241-4.
Landsman et al., Lung macrophages serve as obligatory intermediate between blood monocytes and alveolar macrophages. J Immunol. Sep. 15, 2007;179(6):3488-94.
Lau et al., Lipid-containing mimetics of natural triggers of innate immunity as CTL-inducing influenza vaccines. Int Immunol. Dec. 2006;18(12):1801-13.
Licalsi et al., Dry powder inhalation as a potential delivery method for vaccines. Vaccine. Mar. 26, 1999;17(13-14):1796-803.
Martinez et al., Direct TLR2 signaling is critical for NK cell activation and function in response to vaccinia viral infection. PLoS Pathog. Mar. 12, 2010;6(3):e1000811, 13 pages.
Medical Dictionary, admixture. retrieved online at: https://medical-dictionary.thefreedictionary.com/admixture. 1 page, (2012).
Meng et al., Cellular recognition of tri-/di-palmitoylated peptides is independent from a domain encompassing the N-terminal seven leucine-rich repeat (LRR)/LRR-like motifs of TLR2. J Biol Chem. Oct. 10, 2003;278(41):39822-9.
Metzger et al., Synthesis of novel immunologically active tripalmitoyl-S-glycerylcysteinyl lipopeptides as useful intermediates for immunogen preparations. Int J Pept Protein Res. Jan. 1991;37(1):46-57.
Morr et al., Differential recognition of structural details of bacterial lipopeptides by toll-like receptors. Eur J Immunol. Dec. 2002;32(12):3337-47.
Muhlradt et al., Isolation, structure elucidation, and synthesis of a macrophage stimulatory lipopeptide from Mycoplasma fermentans acting at picomolar concentration. J Exp Med. Jun. 2, 1997;185(11):1951-8.
Muhlradt et al., Structure and specific activity of macrophage-stimulating lipopeptides from Mycoplasma hyorhinis. Infect Immun. Oct. 1998;66(10):4804-10.
Okusawa et al., Relationship between structures and biological activities of mycoplasmal diacylated lipopeptides and their recognition by toll-like receptors 2 and 6. Infect Immun. Mar. 2004;72(3):1657-65.

(56) References Cited

OTHER PUBLICATIONS

Olive et al., A lipid core peptide construct containing a conserved region determinant of the group A streptococcal M protein elicits heterologous opsonic antibodies. Infect Immun. May 2002;70(5):2734-8.
Olive et al., Enhanced protection against *Streptococcus pyogenes* infection by intranasal vaccination with a dual antigen component M protein/Sfbl lipid core peptide vaccine formulation. Vaccine. Feb. 26, 2007;25(10):1789-97.
Ozinsky et al., The repertoire for pattern recognition of pathogens by the innate immune system is defined by cooperation between toll-like receptors. Proc Natl Acad Sci U S A. Dec. 5, 2000;97(25):13766-71.
Palma et al., The toll-like receptor 2/6 ligand MALP-2 reduces the viability of *Mycobacterium tuberculosis* in murine macrophages. Open Microbiol J. Apr. 3, 2009;3:47-52.
Pascolo et al., HLA-A2.1-restricted education and cytolytic activity of CD8(+) T lymphocytes from beta2 microglobulin (beta2m) HLA-A2.1 monochain transgenic H-2Db beta2m double knockout mice. J Exp Med. Jun. 16, 1997;185(12):2043-51.
Pina et al., Shiga toxin B-subunit sequential binding to its natural receptor in lipid membranes. Biochim Biophys Acta. Mar. 2007;1768(3):628-36.
Poltorak et al., Defective LPS signaling in C3H/HeJ and C57BL/10ScCr mice: mutations in Tlr4 gene. Science. Dec. 11, 1998;282(5396):2085-8.
Raffai et al., Binding of an antibody mimetic of the human low density lipoprotein receptor to apolipoprotein E is governed through electrostatic forces. Studies using site-directed mutagenesis and molecular modeling. J Biol Chem. Mar. 10, 2000;275(10):7109-16.
Raffai et al., Molecular characterization of two monoclonal antibodies specific for the LDL receptor-binding site of human apolipoprotein E. J Lipid Res. Sep. 1995;36(9):1905-18.
Reppe et al., Immunostimulation with macrophage-activating lipopeptide-2 increased survival in murine pneumonia. Am J Respir Cell Mol Biol. Apr. 2009;40(4):474-81.
Riedl et al., Complexes of DNA vaccines with cationic, antigenic peptides are potent, polyvalent CD8(+) T-cell-stimulating immunogens. Methods Mol Med. 2006;127:159-69.
Rose et al., FSL-1, a bacterial-derived toll-like receptor 2/6 agonist, enhances resistance to experimental HSV-2 infection. Virol J. Nov. 10, 2009;6:195, 11 pages.
Rothbard et al., A sequence pattern common to T cell epitopes. EMBO J. Jan. 1988;7(1):93-100.
Schirmbeck et al., Antigenic epitopes fused to cationic peptide bound to oligonucleotides facilitate Toll-like receptor 9-dependent, but CD4+ T cell help-independent, priming of CD8+ T cells. J Immunol. Nov. 15, 2003;171(10):5198-207.
Schwandner et al., Peptidoglycan- and lipoteichoic acid-induced cell activation is mediated by toll-like receptor 2. J Biol Chem. Jun. 18, 1999;274(25):17406-9.
Seifert et al., Activation of superoxide formation and lysozyme release in human neutrophils by the synthetic lipopeptide Pam3Cys-Ser-(Lys)4. Involvement of guanine-nucleotide-binding proteins and synergism with chemotactic peptides. Biochem J. May 1, 1990;267(3):795-802.
Sekiya et al., PEGylation of a TLR2-agonist-based vaccine delivery system improves antigen trafficking and the magnitude of ensuing antibody and CD8+ T cell responses. Biomaterials. Aug. 2017;137:61-72.
Sherman et al., Extracellular processing of peptide antigens that bind class I major histocompatibility molecules. J Exp Med. May 1, 1992;175(5):1221-6.
Shiratsuchi et al., Elimination of influenza virus-infected cells by phagocytosis. Yakugaku Zasshi. Dec. 2006;126(12):1245-51.
Stambach et al., Characterization of carbohydrate recognition by langerin, a C-type lectin of Langerhans cells. Glycobiology. May 2003;13(5):401-10.
Takeuchi et al., Cutting edge: preferentially the R-stereoisomer of the mycoplasmal lipopeptide macrophage-activating lipopeptide-2 activates immune cells through a toll-like receptor 2- and MyD88-dependent signaling pathway. J Immunol. Jan. 15, 2000;164(2):554-7.
Takeuchi et al., Cutting edge: role of Toll-like receptor 1 in mediating immune response to microbial lipoproteins. J Immunol. Jul. 1, 2002;169(1):10-4.
Tannock et al., Relative immunogenicity of the cold-adapted influenza virus A/Ann Arbor/6/60 (A/AA/6/60-ca), recombinants of A/AA/6/60-ca, and parental strains with similar surface antigens. Infect Immun. Feb. 1984;43(2):457-62.
Tansey et al., Synthesis and characterization of branched poly(L-glutamic acid) as a biodegradable drug carrier. J Control Release. Jan. 8, 2004;64(10):39-51.
Tighe et al., Conjugation of protein to immunostimulatory DNA results in a rapid, long-lasting and potent induction of cell-mediated and humoral immunity. Eur J Immunol. Jul. 2000;30(7):1939-47.
Wallace et al., The cytotoxic T-cell response to herpes simplex virus type 1 infection of C57BL/6 mice is almost entirely directed against a single immunodominant determinant. J Virol. Sep. 1999;73(9):7619-26.
Wikipedia, TLR-2. Retrieved online at: https://en.wikipedia.org/wiki/TLR2. 14 pages, (2021).
Zeng et al., Characterisation of the antibody response to a totally synthetic immunocontraceptive peptide vaccine based on LHRH. Vaccine. Aug. 15, 2005;23(35):4427-35.
Zeng et al., Highly immunogenic and totally synthetic lipopeptides as self-adjuvanting immunocontraceptive vaccines. J Immunol. Nov. 1, 2002;169(9):4905-12.
Zeng et al., Synthesis of a new template with a built-in adjuvant and its use in constructing peptide vaccine candidates through polyoxime chemistry. J Pept Sci. Jan. 1996-Feb.;2(1):66- 72.
Zeng et al., Totally synthetic lipid-containing polyoxime peptide constructs are potent immunogens. Vaccine. Jan. 6, 2000;18(11-12):1031-9.
Bartlett et al., Upper Airway TLR2 Immune Modulators Prime Broad Respiratory Immunity Against Rhinovirus and Influenza Infection and Inhibit Subsequent Lung Inflammation. American Journal of Respiratory and Critical Care Medicine. 2018; 197:Abstract A7803, 3 pages.
Batzloff et al., Intranasal vaccination with a lipopeptide containing a conformationally constrained conserved minimal peptide, a universal T cell epitope, and a self-adjuvanting lipid protects mice from group A *Streptococcus* challenge and reduces throat colonization. J Infect Dis. Aug. 1, 2006;194(3):325-30.
Bogoch et al., Diagnosis of influenza from lower respiratory tract sampling after negative upper respiratory tract sampling. Virulence. Jan. 1, 2013;4(1):82-4.
Boiardi et al., Reducing transmission of SARS-COV-2 with intranasal prophylaxis. EBioMedicine. Jan. 2021;63:103170, 2 pages.
Chua et al., Enhancing immunogenicity of HCV DNA vaccines by targeted delivery to dendritic cells. Journal of Hepatology. 2008;48:S236, Abstract 634.
Duggan et al., Broad Resistance Against Pneumonia Induced By Synergistic TLR2/6 And TLR9 Stimulation. American Journal of Respiratory and Critical Care Medicine. 2010;181:Abstract A1799, 3 pages.
Ernest et al., The Toll-Like Receptor 2 agonist PEG-Pam2Cys as an immunochemoprophylactic and Immunochemotherapeutic against the liver and transmission stages of malaria parasites. Int J Parasitol Drugs Drug Resist. Dec. 2018;8(3):451-458.
Feng et al., A toll-like receptor agonist mimicking microbial signal to generate tumor-suppressive macrophages. Nat Commun. May 22, 2019;10(1):2272, 14 pages.
Jaiswal et al., Innate Immune Response Modulation and Resistance to SARS-COV-2 infection: A Prospective Comparative Cohort Study in High Risk Healthcare Workers. medRxiv. Retrieved online at: https://www.medrxiv.org/content/10.1101/2020.10.20.20214965v1. Oct. 21, 2020, 6 pages.
Proud et al., Prophylactic intranasal administration of a TLR2/6 agonist reduces upper respiratory tract viral shedding In a SARS-COV-2 challenge ferret model. EBioMedicine. Jan. 2021;63:103153, 9 pages.

(56) References Cited

OTHER PUBLICATIONS

Rathananand et al., Preparation of mucoadhesive microspheres for nasal delivery by spray drying. Indian J Pharm Sci. 2007;69(5):651-657.
Riedl et al., Peptides containing antigenic and cationic domains have enhanced, multivalent immunogenicity when bound to DNA vaccines. J Mol Med (Berl). Feb. 2004;82(2):144-52.
Sharma et al., Effect of TLR agonist on infections bronchitis virus replication and cytokine expression in embryonated chicken eggs. Mol Immunol. Apr. 2020;120:52-60.
Wali et al., Immune Modulation to Improve Survival of Viral Pneumonia in Mice. Am J Respir Cell Mol Biol. Dec. 2020;63(6):758-766.
You et al., Induced Resistance to Influenza A Infection By Cooperative TLR2/6 and TLR9 Activation. American Journal of Respiratory and Critical Care Medicine. 2010;181:Abstract A2629, 3 pages.
International Search Report and Written Opinion for Application No. PCT/AU2020/050660, dated Sep. 3, 2020, 10 pages.
International Search Report and Written Opinion for Application No. PCT/AU2021/050506, dated Jul. 13, 2021, 14 pages.
Agnihotri et al., Structure-activity relationships in toll-like receptor 2-agonists leading to simplified monoacyl lipopeptides. J Med Chem. Dec. 8, 2011;54(23):8148-60.
Li et al., Relationship of Toll like receptor-2 and some virus infectious diseases. Chemistry of Life. 2009;4:568-571.
Lu et al., Synthesis and Evaluation of Novel TLR2 Agonists as Potential Adjuvants for Cancer Vaccines. J Med Chem. Mar. 12, 2020;63(5):2282-2291.
Sasidharan Nair et al., Immune checkpoint inhibitors in cancer therapy: a focus on T-regulatory cells. Immunol Cell Biol. Jan. 2018; 96(1):21-33.
Wang et al., Adjuvant effect of the novel TLR1/TLR2 agonist Diprovocim synergizes with anti-PD-L1 to eliminate melanoma in mice. Proc Natl Acad Sci U S A. Sep. 11, 2018;115(37):E8698-E8706.
Alfredo et al., Pathophysiology of viral-induced exacerbations of COPD. International Journal of COPD. 2007;2 (4):477-483.

* cited by examiner

OPTIMISED COMPOUNDS

CROSS-REFERENCE TO RELATED APPLICATIONS

This application is a U.S. national stage filing, under 35 U.S.C. § 371(c), of International Application No. PCT/AU2018/051397, filed on Dec. 21, 2018, which claims priority to Australian Provisional Application No. 2017905128, filed on Dec. 21, 2017, Australian Provisional Application No. 2018901056, filed on Mar. 29, 2018, and Australian Provisional Application No. 2018903597, filed on Sep. 25, 2018. The entire contents of each of the aforementioned applications are herein incorporated by reference.

FIELD OF THE INVENTION

The present invention relates to compounds and their compositions, and the use of such compounds and compositions in the prevention and/or treatment of respiratory infections, or respiratory diseases or conditions associated with viral or bacterial infections.

BACKGROUND OF THE INVENTION

Respiratory infections are among the most common causes of human disease worldwide and are commonly caused by viruses. According to the World Health Organisation (WHO), worldwide, seasonal epidemics of influenza alone are estimated to result in about 3 to 5 million cases of severe illness, and about 250,000 to 500,000 deaths per year.

Although vaccines are available for some seasonal strains, for example influenza, these have not always been shown to be adequate due to several factors, such as infection between the lag phase between inoculation and the formation of antibodies and immune cells being formed. Seasonal vaccinations often also need modification, including re-formulation and administration, and may also not provide protection for the full length of time desired. For other occurrences of influenza, such as unexpected panademic outbreaks, a vaccine is not always known, developed or available.

Viral respiratory infections can also worsen the severity of diseases of the respiratory conditions leading to exacerbations (attacks). Exacerbations can occur for conditions such as asthma and chronic obstructive pulmonary disease (COPD). Asthma and COPD exacerbations are the most clinically and economically important forms of the diseases.

The vast majority of exacerbations, particularly in asthma, continue to occur despite use of the best available current therapies. When exacerbations do occur, treatment options are limited and have developed little in recent years. Treatment involves increasing doses of inhaled bronchodilators and systemic or oral corticosteroids—which are the same drugs that failed to prevent the exacerbation occurring in the first place.

There is a need, therefore, for new or improved compounds and methods for the treatment and/or prevention for respiratory infections, or respiratory conditions associated with viral or bacterial infections.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention provides Toll-Like Receptor 2 protein (TLR2) agonist compounds and their compositions. TLR2 agonists have previously been identified to show potential in treating respiratory diseases and conditions associated with infectious agents such as viruses and bacteria. The compounds and compositions of the present application have shown particularly potent activity and have use in therapeutic areas such as treating and/or preventing respiratory diseases or conditions associated with viral or bacterial infections.

In one aspect, the present invention provides a compound comprising the structure:

A-Y—B wherein A comprises or consists of:

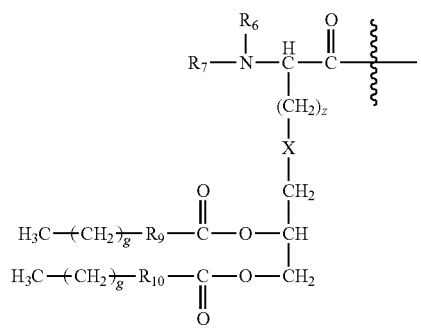

wherein each g is independently 10, 11, 12, 13, 14, 15, 16, 17 or 18;

z is 1 or 2;

X is S or S($=$O);

$R_6$ and $R_7$ are independently selected from the group consisting of H, a straight or branched $C_1$-$C_4$ alkyl, and —C($=$O)$CH_3$;

$R_9$ and $R_{10}$ are independently selected from the group consisting of —NH—, —O— or a single bond;

Y is

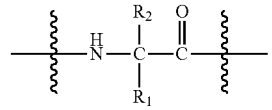

wherein $R_1$ and $R_2$ are independently selected from the group consisting of H, —$CH_2OH$, —$CH_2CH_2OH$, —CH($CH_3$)OH, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;

$R_8$ is selected from the group consisting of H and a straight or branched $C_1$-$C_6$ alkyl;

and

B comprises or consists of Polyethylene Glycol (PEG), or a pharmaceutically acceptable salt or prodrug thereof.

In one aspect, the present invention provides a compound comprising the structure:

A-Y—B wherein A comprises or consists of:

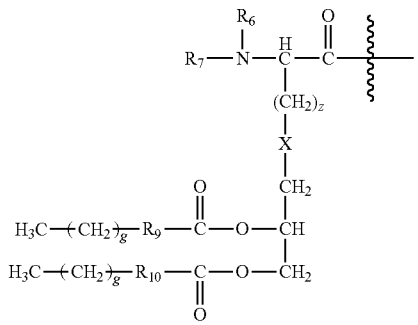

wherein each g is independently 10, 11, 12, 13, 14, 15, 16, 17 or 18;
z is 1 or 2;
X is S or S(=O);
$R_6$ and $R_7$ are independently selected from the group consisting of H, a straight or branched $C_1$-$C_4$ alkyl, and —C(=O)$CH_3$;
$R_9$ and $R_{10}$ are independently selected from the group consisting of —NH—, —O— or a single bond;
Y is

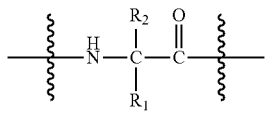

wherein $R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H; and
B comprises or consists of Polyethylene Glycol (PEG), or a pharmaceutically acceptable salt or prodrug thereof.
In one aspect, the present invention provides a compound comprising the structure:

A-Y—B wherein A comprises or consists of:

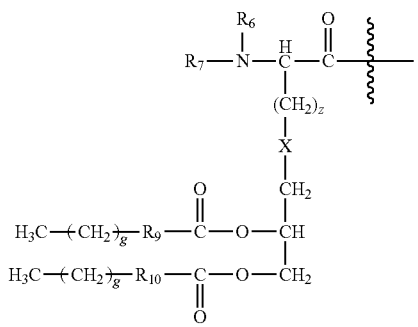

wherein each g is independently 10, 11, 12, 13, 14, 15, 16, 17 or 18;
z is 1;
X is S;
$R_6$ and $R_7$ are H;
$R_9$ and $R_{10}$ are both a single bond;
Y is

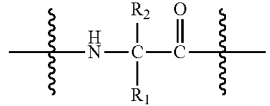

wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;
$R_8$ is selected from the group consisting of H and a straight or branched $C_1$-$C_6$ alkyl; and
B comprises or consists of Polyethylene Glycol (PEG), or a pharmaceutically acceptable salt or prodrug thereof.
In one aspect, the present invention provides a compound comprising the structure:

A-Y—B wherein A comprises or consists of:

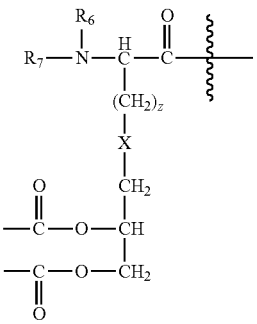

wherein each g is independently 10, 11, 12, 13, 14, 15, 16, 17 or 18;
z is 1;
X is S;
$R_6$ and $R_7$ are H;
$R_9$ and $R_{10}$ are both a single bond;
Y is

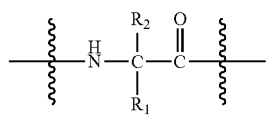

wherein $R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H; and
B comprises or consists of Polyethylene Glycol (PEG), or a pharmaceutically acceptable salt or prodrug thereof.
In one aspect, the present invention provides a compound comprising the structure:

A-Y—B wherein A comprises or consists of:

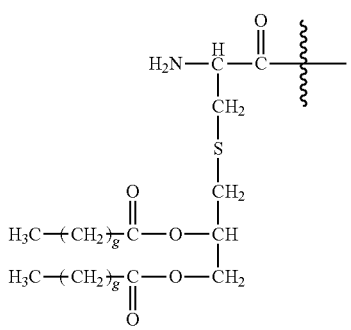

wherein each g is independently 10, 11, 12, 13, 14, 15, 16, 17 or 18;
Y is

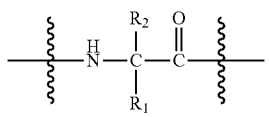

wherein $R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;
and
B comprises or consists of Polyethylene Glycol (PEG),
or a pharmaceutically acceptable salt or prodrug thereof.

The present invention also provides a compound comprising Pam2Cys and PEG, wherein the Pam2Cys and PEG are linked by a glycine, serine, homoserine, threonine, phosphoserine, asparagine or glutamine residue, or an ester of a glutamine residue,
wherein
Pam2Cys in the compound has the structure:

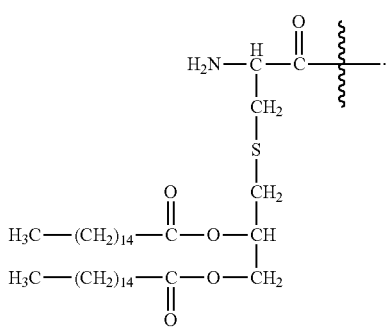

The present invention also provides a compound comprising Pam2Cys and PEG, wherein the Pam2Cys and PEG are linked by a serine, homoserine, threonine or phosphoserine residue, wherein
Pam2Cys in the compound has the structure:

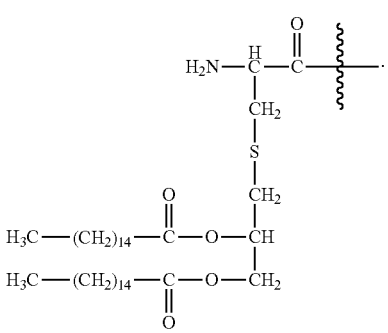

In one aspect, the present invention provides a compound comprising:

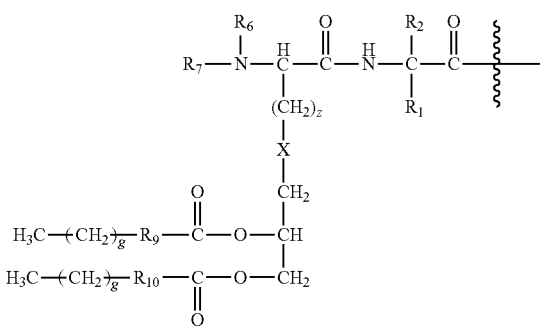

wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;
$R_6$ and $R_7$ are independently selected from the group consisting of H, a straight or branched $C_1$-$C_4$ alkyl, and —$C(=O)CH_3$;
$R_8$ is selected from the group consisting of H and a straight or branched $C_1$-$C_6$ alkyl;
$R_9$ and $R_{10}$ are independently selected from the group consisting of —NH—, —O— or a single bond;
z is 1 or 2; and
X is S or S(=O);
covalently linked to polyethylene glycol (PEG),
or a pharmaceutically acceptable salt or prodrug thereof.
In one aspect, the present invention provides a compound comprising:

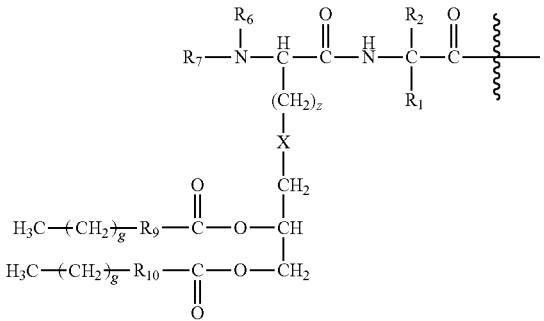

wherein $R_1$ and $R_2$ are independently selected from the group consisting of H, —CH$_2$OH, —CH$_2$CH$_2$OH, —CH(CH$_3$)OH and —CH$_2$OPO(OH)$_2$, wherein any one of the alkyl hydrogens can be replaced with a halogen, and wherein $R_1$ and $R_2$ are not both H;

$R_6$ and $R_7$ are independently selected from the group consisting of H, a straight or branched C$_1$-C$_4$ alkyl, and —C(=O)CH$_3$;

$R_9$ and $R_{10}$ are independently selected from the group consisting of —NH—, —O— or a single bond;

z is 1 or 2; and

X is S or S(=O);

covalently linked to polyethylene glycol (PEG), or a pharmaceutically acceptable salt or prodrug thereof.

In one aspect, the present invention provides a compound comprising:

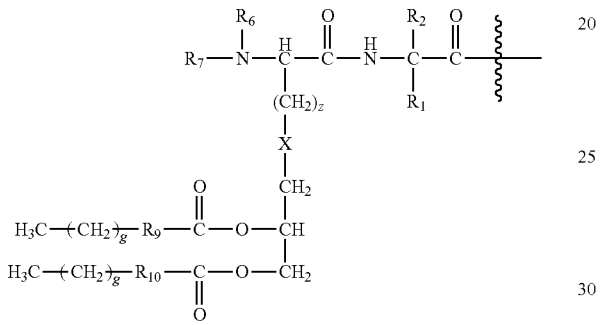

wherein $R_1$ and $R_2$ are independently selected from the group consisting of H, —CH$_2$OH, —CH$_2$CH$_2$OH, —CH(CH$_3$)OH, —CH$_2$OPO(OH)$_2$, —CH$_2$C(=O)NH$_2$, —CH$_2$CH$_2$C(=O)OH and —CH$_2$CH$_2$C(=O)OR$_8$, wherein any one of the alkyl hydrogens can be replaced with a halogen;

$R_6$ and $R_7$ are H;

$R_8$ is selected from the group consisting of H and a straight or branched C$_1$-C$_6$ alkyl;

$R_9$ and $R_{10}$ are both a single bond;

z is 1; and

X is S;

covalently linked to polyethylene glycol (PEG), or a pharmaceutically acceptable salt or prodrug thereof.

In one aspect, the present invention provides a compound comprising:

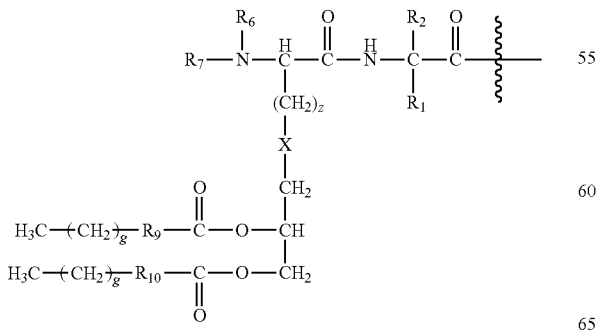

wherein $R_1$ and $R_2$ are independently selected from the group consisting of H, —CH$_2$OH, —CH$_2$CH$_2$OH, —CH(CH$_3$)OH and —CH$_2$OPO(OH)$_2$, wherein any one of the alkyl hydrogens can be replaced with a halogen, and wherein $R_1$ and $R_2$ are not both H;

$R_6$ and $R_7$ are H;

$R_9$ and $R_{10}$ are both a single bond;

z is 1; and

X is S;

covalently linked to polyethylene glycol (PEG), or a pharmaceutically acceptable salt or prodrug thereof.

In one aspect, the present invention provides a compound comprising:

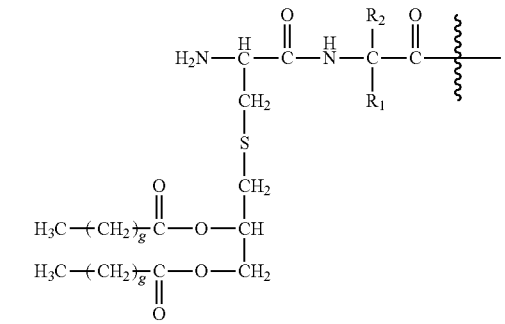

wherein $R_1$ and $R_2$ are independently selected from the group consisting of H, —CH$_2$OH, —CH$_2$CH$_2$OH, —CH(CH$_3$)OH and —CH$_2$OPO(OH)$_2$, wherein any one of the alkyl hydrogens can be replaced with a halogen, and wherein $R_1$ and $R_2$ are not both H;

covalently linked to polyethylene glycol (PEG), or a pharmaceutically acceptable salt or prodrug thereof.

In one aspect, the present invention provides a compound of formula (VI):

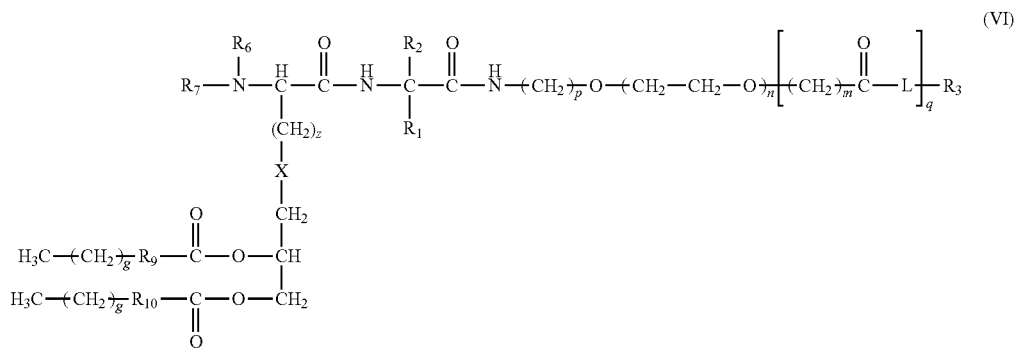

wherein
n is 3 to 100;
m is 1, 2, 3 or 4;
each g is independently 10, 11, 12, 13, 14, 15, 16, 17 or 18;
p is 2, 3 or 4;
q is null or 1;
$R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;
$R_6$ and $R_7$ are independently selected from the group consisting of H, a straight or branched $C_1$-$C_4$ alkyl, and —$C(=O)CH_3$;
$R_8$ is selected from the group consisting of H and a straight or branched $C_1$-$C_6$ alkyl;
$R_9$ and $R_{10}$ are independently selected from the group consisting of —NH—, —O— or a single bond;
z is 1 or 2;
X is S or S(=O);
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

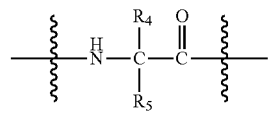

wherein $R_4$ is H; and
$R_5$ is the side chain, or second hydrogen of the amino acid or a pharmaceutically acceptable salt or prodrug thereof.
In one aspect, the present invention provides a compound of formula (VI):

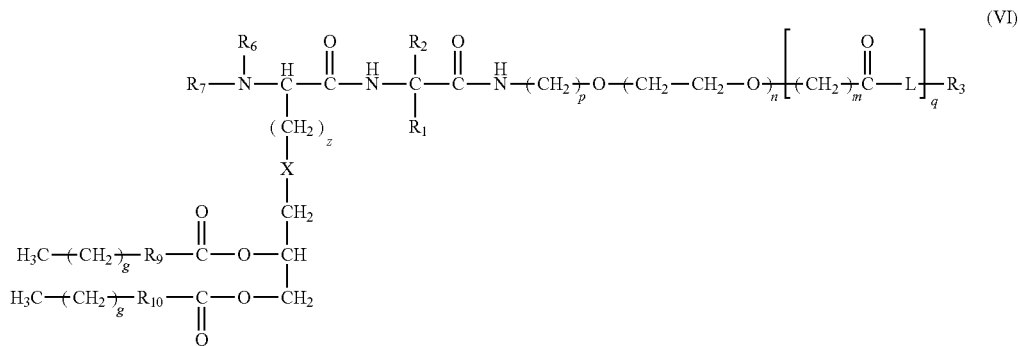

wherein n is 3 to 100;

m is 1, 2, 3 or 4;

each g is independently 10, 11, 12, 13, 14, 15, 16, 17 or 18;

p is 2, 3 or 4;

q is null or 1;

$R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;

$R_6$ and $R_7$ are independently selected from the group consisting of H, a straight or branched $C_1$-$C_4$ alkyl, and —$C(=O)CH_3$;

$R_9$ and $R_{10}$ are independently selected from the group consisting of —NH—, —O— or a single bond;

z is 1 or 2;

X is S or S(=O);

wherein when q=1, $R_3$ is —$NH_2$ or —OH;

wherein when q=0, $R_3$ is H;

L is null or consists of 1 to 10 units, wherein each unit is a natural alpha amino acid or derived from a natural alpha amino acid, and has the formula:

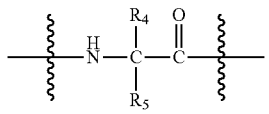

wherein $R_4$ is H; and $R_5$ is the side chain, or second hydrogen of the amino acid or a pharmaceutically acceptable salt or prodrug thereof.

In one aspect, the present invention provides a compound of formula (VI):

wherein n is 3 to 100;

m is 1, 2, 3 or 4;

each g is independently 10, 11, 12, 13, 14, 15, 16, 17 or 18;

p is 2, 3 or 4;

q is null or 1;

$R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_6$, wherein any one of the alkyl hydrogens can be replaced with a halogen;

$R_6$ and $R_7$ are H;

$R_8$ is selected from the group consisting of H and a straight or branched $C_1$-$C_6$ alkyl;

$R_9$ and $R_{10}$ are both a single bond;

z is 1;

X is S;

wherein when q=1, $R_3$ is —$NH_2$ or —OH;

wherein when q=0, $R_3$ is H;

L is null or consists of 1 to 10 units, wherein each unit is a natural alpha amino acid or derived from a natural alpha amino acid, and has the formula:

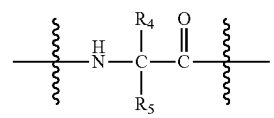

wherein $R_4$ is H; and $R_5$ is the side chain, or second hydrogen of the amino acid or a pharmaceutically acceptable salt or prodrug thereof.

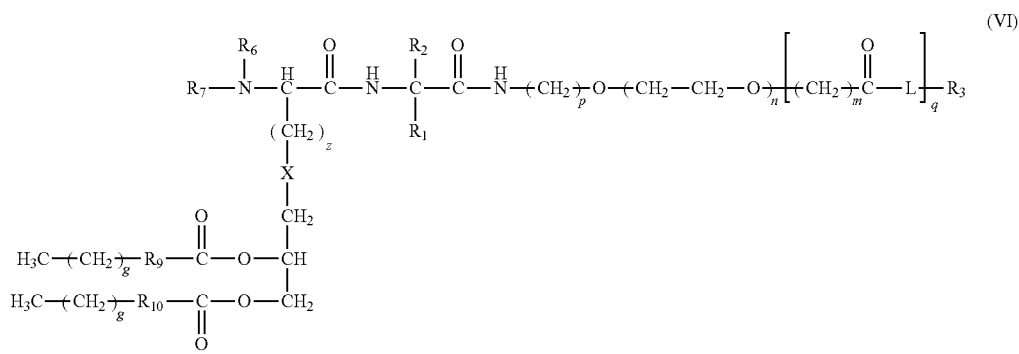

In one aspect, the present invention provides a compound of formula (VI):

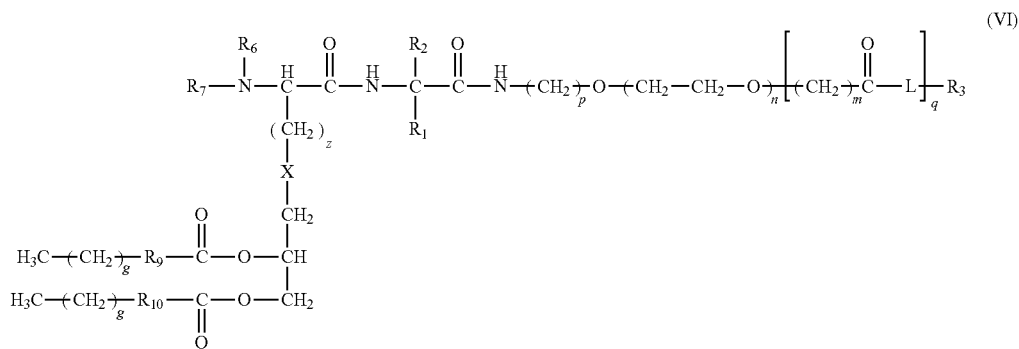

wherein
n is 3 to 100;
m is 1, 2, 3 or 4;
each g is independently 10, 11, 12, 13, 14, 15, 16, 17 or 18;
p is 2, 3 or 4;
q is null or 1;
$R_1$ and $R_2$ are independently selected from the group consisting of H, —CH$_2$OH, —CH$_2$CH$_2$OH, —CH(CH$_3$)OH and —CH$_2$OPO(OH)$_2$, wherein any one of the alkyl hydrogens can be replaced with a halogen, and wherein $R_1$ and $R_2$ are not both H;
$R_6$ and $R_7$ are H;
$R_9$ and $R_{10}$ are both a single bond;
z is 1;
X is S;
wherein when q=1, $R_3$ is —NH$_2$ or —OH;
wherein when q=0, $R_3$ is H;

L is null or consists of 1 to 10 units, wherein each unit is a natural alpha amino acid or derived from a natural alpha amino acid, and has the formula:

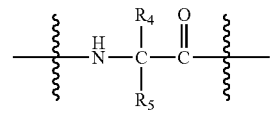

wherein $R_4$ is H; and
$R_5$ is the side chain, or second hydrogen of the amino acid or a pharmaceutically acceptable salt or prodrug thereof.

In one aspect, the present invention provides a compound of formula (I):

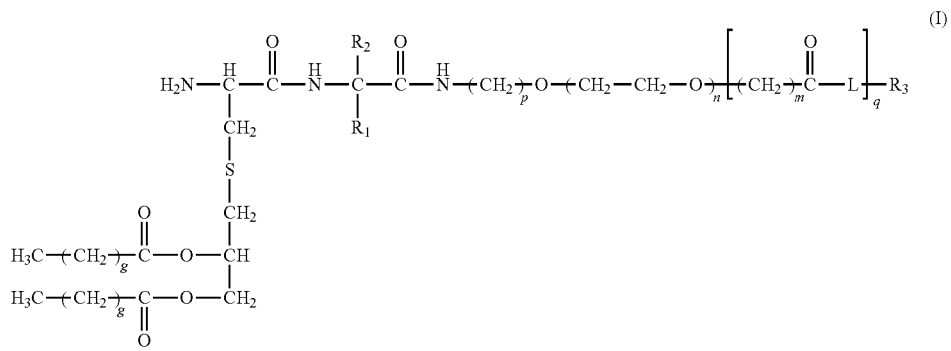

wherein
n is 3 to 100;
m is 1, 2, 3 or 4;
each g is independently 10, 11, 12, 13, 14, 15, 16, 17 or 18;
p is 2, 3 or 4;
q is null or 1;
$R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

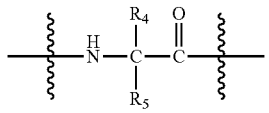

wherein $R_4$ is H; and
$R_5$ is the side chain, or second hydrogen of the amino acid or a pharmaceutically acceptable salt or prodrug thereof.
In one embodiment, the present invention provides a compound of formula (VII):

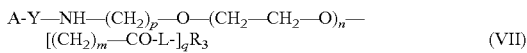 (VII)

wherein
A has the structure:

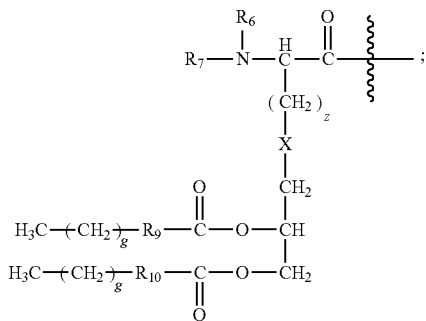

Y is

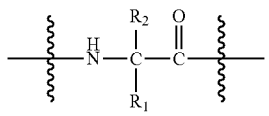

wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;
$R_6$ and $R_7$ are independently selected from the group consisting of H, a straight or branched $C_1$-$C_4$ alkyl, and —$C(=O)CH_3$;

$R_8$ is selected from the group consisting of H and a straight or branched $C_1$-$C_6$ alkyl;
$R_9$ and $R_{10}$ are independently selected from the group consisting of —NH—, —O— or a single bond;
z is 1 or 2;
X is S or S(=O);
n is 3 to 100;
m is 1, 2, 3 or 4;
each g is independently 10, 11, 12, 13, 14, 15, 16, 17 or 18;
p is 2, 3 or 4;
q is null or 1;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

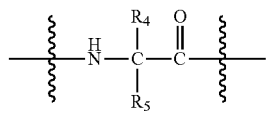

wherein $R_4$ is H; and
$R_5$ is the side chain, or second hydrogen of the amino acid, or a pharmaceutically acceptable salt or prodrug thereof.
In one embodiment, the present invention provides a compound of formula (VII):

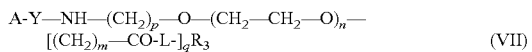 (VII)

wherein
A has the structure:

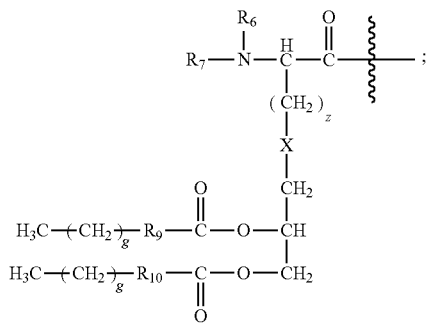

Y is

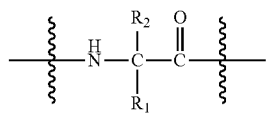

wherein $R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;
$R_6$ and $R_7$ are independently selected from the group consisting of H, a straight or branched $C_1$-$C_4$ alkyl, and —$C(=O)CH_3$;

$R_9$ and $R_{10}$ are independently selected from the group consisting of —NH—, —O— or a single bond;
z is 1 or 2;
X is S or S(=O);
n is 3 to 100;
m is 1, 2, 3 or 4;
each g is independently 10, 11, 12, 13, 14, 15, 16, 17 or 18;
p is 2, 3 or 4;
q is null or 1;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

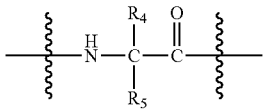

wherein $R_4$ is H; and
$R_5$ is the side chain, or second hydrogen of the amino acid, or a pharmaceutically acceptable salt or prodrug thereof.
In one embodiment, the present invention provides a compound of formula (VII):

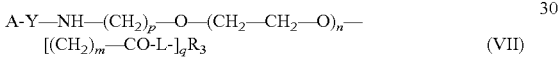 (VII)

wherein
A has the structure:

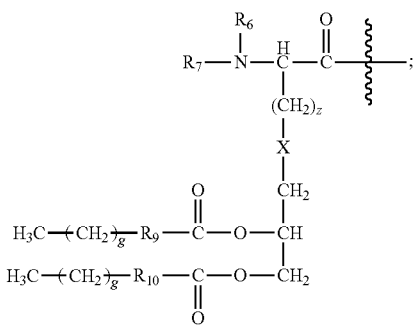

Y is

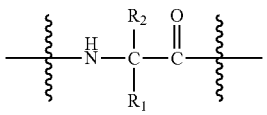

wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;
$R_6$ and $R_7$ are H;
$R_8$ is selected from the group consisting of H and a straight or branched $C_1$-$C_6$ alkyl;

$R_9$ and $R_{10}$ are both a single bond;
z is 1;
X is S;
n is 3 to 100;
m is 1, 2, 3 or 4;
each g is independently 10, 11, 12, 13, 14, 15, 16, 17 or 18;
p is 2, 3 or 4;
q is null or 1;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

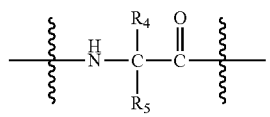

wherein $R_4$ is H; and
$R_5$ is the side chain, or second hydrogen of the amino acid, or a pharmaceutically acceptable salt or prodrug thereof.
In one embodiment, the present invention provides a compound of formula (VII):

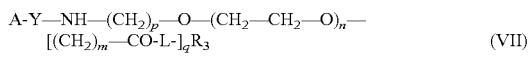 (VII)

wherein
A has the structure:

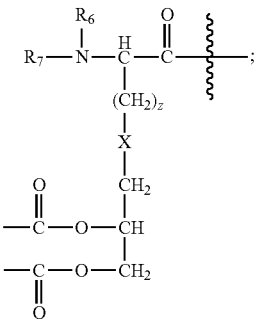

Y is

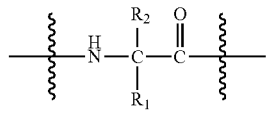

wherein $R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;
$R_6$ and $R_7$ are H;
$R_9$ and $R_{10}$ are both a single bond;
z is 1;
X is S;
n is 3 to 100;
m is 1, 2, 3 or 4;

each g is independently 10, 11, 12, 13, 14, 15, 16, 17 or 18;
p is 2, 3 or 4;
q is null or 1;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

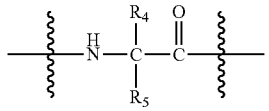

wherein $R_4$ is H; and
$R_5$ is the side chain, or second hydrogen of the amino acid, or a pharmaceutically acceptable salt or prodrug thereof.
In one embodiment, the present invention provides a compound of formula (II):

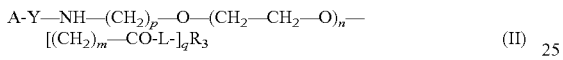

(II)

wherein
A has the structure:

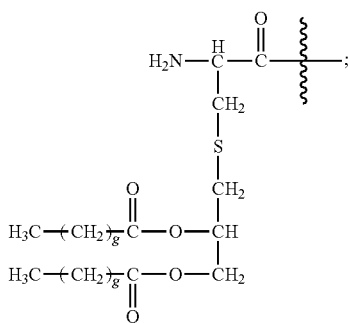

Y is

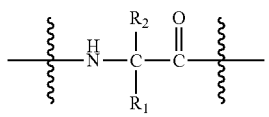

wherein $R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;
n is 3 to 100;
m is 1, 2, 3 or 4;
each g is independently 10, 11, 12, 13, 14, 15, 16, 17 or 18;
p is 2, 3 or 4;
q is null or 1;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

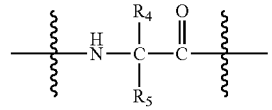

wherein $R_4$ is H; and
$R_5$ is the side chain, or second hydrogen of the amino acid, or a pharmaceutically acceptable salt or prodrug thereof.
In one embodiment, the compound has the formula (VIII):

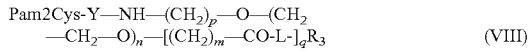

(VIII)

wherein
Pam2Cys has the structure:

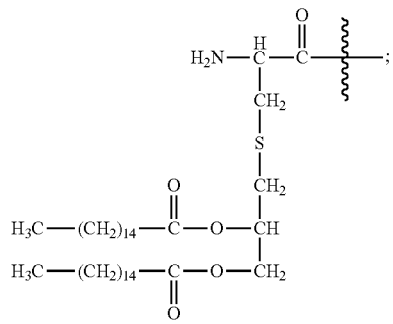

Y is:

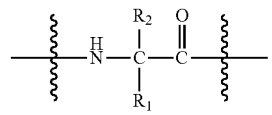

wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;
$R_8$ is selected from the group consisting of H and a straight or branched $C_1$-$C_6$ alkyl;
n is 3 to 100;
m is 1, 2, 3 or 4;
p is 2, 3 or 4;
q is null or 1;
wherein when q=1, $R_3$ is H, —$NH_2$ or —OH;
wherein when q=0, $R_3$ is H;
L is null or consists of 1 to 10 units, wherein each unit is a natural alpha amino acid or derived from a natural alpha amino acid, and has the formula:

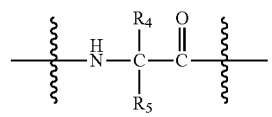

wherein $R_4$ is H; and
$R_5$ is the side chain, or second hydrogen of the amino acid, or a pharmaceutically acceptable salt or prodrug thereof.

In one embodiment, the compound has the formula (VIII):

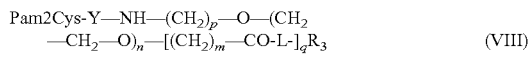
(VIII)

wherein
Pam2Cys has the structure:

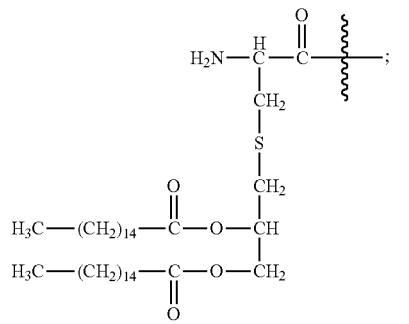

Y is:

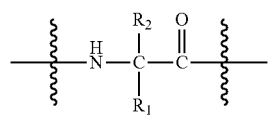

wherein $R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen and wherein $R_1$ and $R_2$ are not both H;

n is 3 to 100;
m is 1, 2, 3 or 4;
p is 2, 3 or 4;
q is null or 1;
wherein when q=1, $R_3$ is H, —$NH_2$ or —OH;
wherein when q=0, $R_3$ is H;
L is null or consists of 1 to 10 units, wherein each unit is a natural alpha amino acid or derived from a natural alpha amino acid, and has the formula:

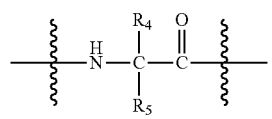

wherein $R_4$ is H; and
$R_5$ is the side chain, or second hydrogen of the amino acid, or a pharmaceutically acceptable salt or prodrug thereof.
In one embodiment, the compound has the formula (III):

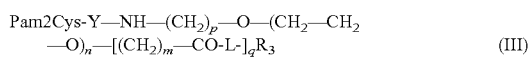
(III)

wherein
Pam2Cys has the structure:

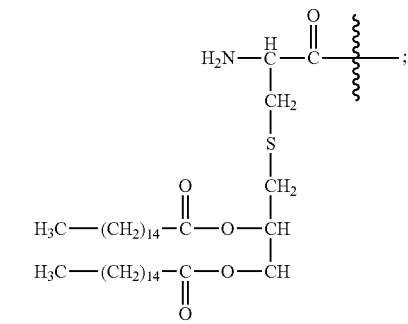

Y is:

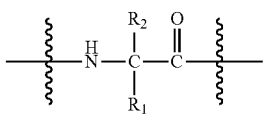

wherein $R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;

n is 3 to 100;
m is 1, 2, 3 or 4;
p is 2, 3 or 4;
q is null or 1;
wherein when q=1, $R_3$ is H, —$NH_2$ or —OH;
wherein when q=0, $R_3$ is H;
L is null or consists of 1 to 10 units, wherein each unit is a natural alpha amino acid or derived from a natural alpha amino acid, and has the formula:

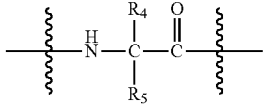

wherein $R_4$ is H; and
$R_5$ is the side chain, or second hydrogen of the amino acid, or a pharmaceutically acceptable salt or prodrug thereof.
In one embodiment, the compound has the formula (IV):

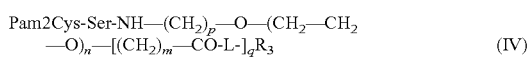
(IV)

wherein
Pam2Cys-Ser has the structure:

$$H_2N-\overset{H}{\underset{CH_2}{C}}-\overset{O}{\underset{}{C}}-\overset{H}{\underset{}{N}}-\overset{H}{\underset{CH_2}{C}}-\overset{O}{\underset{}{C}}-$$
$$\underset{S}{|}\qquad\qquad\underset{OH}{|}$$
$$H_3C-(CH_2)_{14}-\overset{O}{\underset{}{C}}-O-\overset{CH_2}{\underset{}{CH}}$$
$$H_3C-(CH_2)_{14}-\overset{}{\underset{O}{C}}-O-CH$$

n is 3 to 100;
m is 1, 2, 3 or 4;
p is 2, 3 or 4;
q is null or 1;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

$$-\overset{H}{\underset{}{N}}-\overset{R_4}{\underset{R_5}{C}}-\overset{O}{\underset{}{C}}-$$

wherein $R_4$ is H; and
$R_5$ is the side chain, or second hydrogen of the amino acid, or a pharmaceutically acceptable salt or prodrug thereof.
In one embodiment, the compound has the formula (X):

wherein
n is 3 to 100;
k is 3 to 100;
m is 1, 2, 3 or 4;
each g is independently 10, 11, 12, 13, 14, 15, 16, 17 or 18;
p is 2, 3 or 4;
t is 2, 3 or 4;
h is 1, 2, 3 or 4;
q is null or 1;
wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;
$R_6$ and $R_7$ are independently selected from the group consisting of H, a straight or branched $C_1$-$C_4$ alkyl, and —$C(=O)CH_3$;
$R_8$ is selected from the group consisting of H and a straight or branched $C_1$-$C_6$ alkyl;
$R_9$ and $R_{10}$ are independently selected from the group consisting of —NH—, —O— or a single bond;
z is 1 or 2;
X is S or S(=O);
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

$$-\overset{H}{\underset{}{N}}-\overset{R_4}{\underset{R_5}{C}}-\overset{O}{\underset{}{C}}-$$

wherein $R_4$ is H; and
$R_5$ is the side chain, or second hydrogen of the amino acid, or a pharmaceutically acceptable salt or prodrug thereof.

formula (X)

$$R_7-\overset{R_6}{\underset{(CH_2)_z}{N}}-\overset{}{\underset{}{C}}-\overset{O}{\underset{}{C}}-\overset{}{\underset{H}{N}}-\overset{R_2}{\underset{R_1}{C}}-\overset{O}{\underset{}{C}}-\overset{}{\underset{H}{N}}(CH_2)_p-O-(CH_2-CH_2-O)_n-(CH_2)_h-\overset{O}{\underset{}{C}}-\overset{}{\underset{H}{N}}-(CH_2)_t-O-(CH_2-CH_2-O)_k-[(CH_2)_m-\overset{O}{\underset{}{C}}-L]_q-R_3$$
$$\underset{X}{|}$$
$$\underset{CH_2}{|}$$
$$H_3C-(CH_2)_g-R_9-\overset{O}{\underset{}{C}}-O-\overset{}{\underset{}{CH}}$$
$$H_3C-(CH_2)_g-R_{10}-\overset{}{\underset{O}{C}}-O-CH_2$$

In one embodiment, the compound has the formula (X):

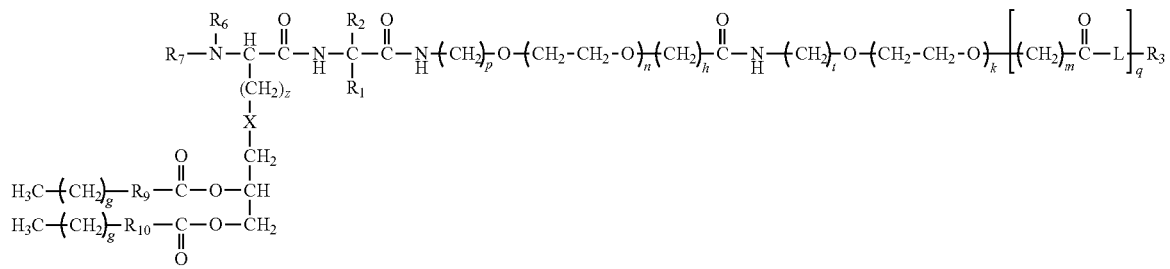

formula (X)

wherein
n is 3 to 100;
k is 3 to 100;
m is 1, 2, 3 or 4;
each g is independently 10, 11, 12, 13, 14, 15, 16, 17 or 18;
p is 2, 3 or 4;
t is 2, 3 or 4;
h is 1, 2, 3 or 4;
q is null or 1;
wherein $R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;
$R_6$ and $R_7$ are independently selected from the group consisting of H, a straight or branched $C_1$-$C_4$ alkyl, and —C(=O)$CH_3$;
$R_9$ and $R_{10}$ are independently selected from the group consisting of —NH—, —O— or a single bond;
z is 1 or 2;
X is S or S(=O);
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

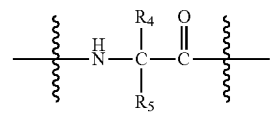

wherein $R_4$ is H; and
$R_5$ is the side chain, or second hydrogen of the amino acid, or a pharmaceutically acceptable salt or prodrug thereof.
In one embodiment, the compound has the formula (X):

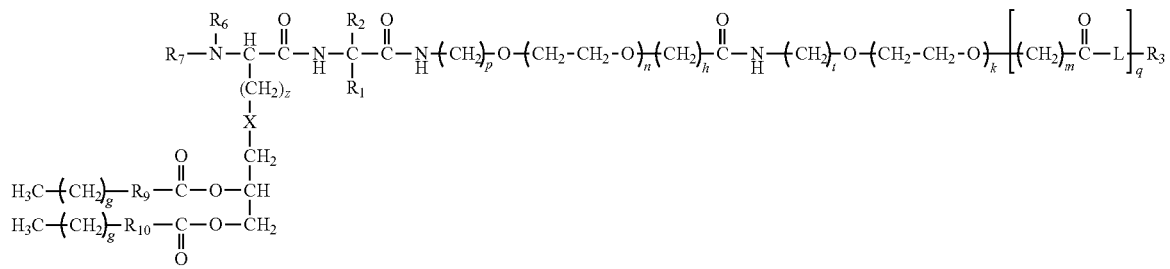

formula (X)

wherein n is 3 to 100;
k is 3 to 100;
m is 1, 2, 3 or 4;
each g is independently 10, 11, 12, 13, 14, 15, 16, 17 or 18;
p is 2, 3 or 4;
t is 2, 3 or 4;
h is 1, 2, 3 or 4;
q is null or 1;
wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;
$R_6$ and $R_7$ are H;
$R_8$ is selected from the group consisting of H and a straight or branched $C_1$-$C_6$ alkyl;
$R_9$ and $R_{10}$ are both a single bond;
z is 1;
X is S;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

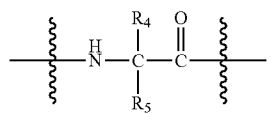

wherein $R_4$ is H; and
$R_5$ is the side chain, or second hydrogen of the amino acid, or a pharmaceutically acceptable salt or prodrug thereof.
In one embodiment, the compound has the formula (X):

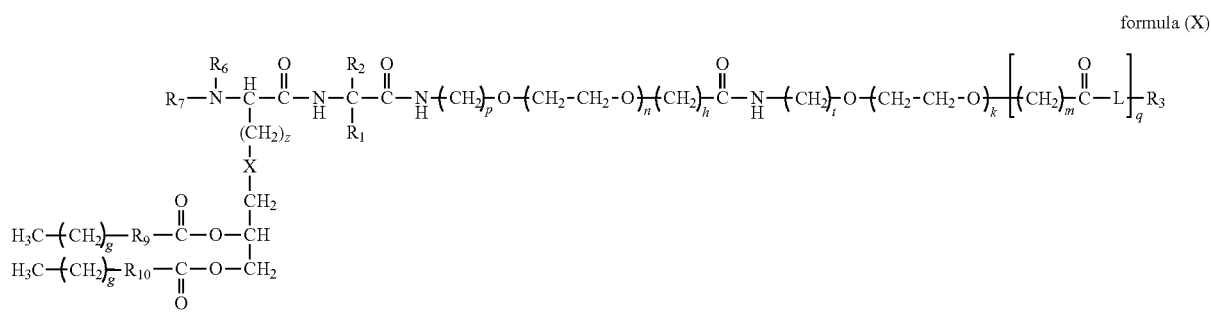

formula (X)

wherein n is 3 to 100;
k is 3 to 100;
m is 1, 2, 3 or 4;
each g is independently 10, 11, 12, 13, 14, 15, 16, 17 or 18;
p is 2, 3 or 4;
t is 2, 3 or 4;
h is 1, 2, 3 or 4;
q is null or 1;
wherein $R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;
$R_6$ and $R_7$ are H;
$R_9$ and $R_{10}$ are both a single bond;
z is 1;
X is S;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

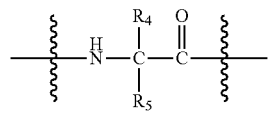

wherein $R_4$ is H; and
$R_5$ is the side chain, or second hydrogen of the amino acid, or a pharmaceutically acceptable salt or prodrug thereof.
In one embodiment, the compound has the formula (V):

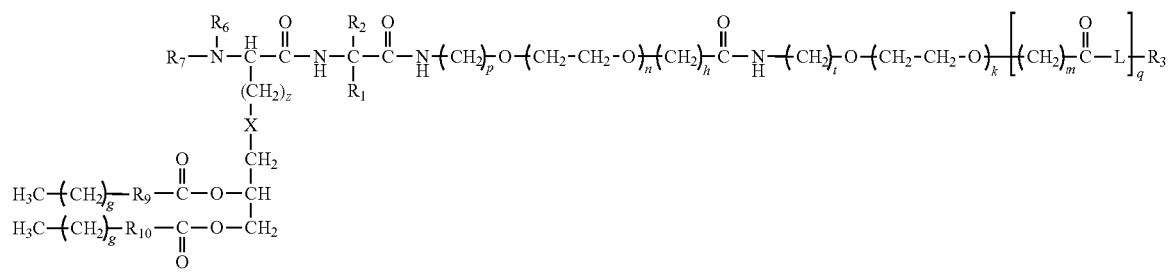

formula (X)

wherein n is 3 to 100;

k is 3 to 100;

m is 1, 2, 3 or 4;

each g is independently 10, 11, 12, 13, 14, 15, 16, 17 or 18;

p is 2, 3 or 4;

t is 2, 3 or 4;

h is 1, 2, 3 or 4;

q is null or 1;

$R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;

wherein when q=1, $R_3$ is —$NH_2$ or —OH;

wherein when q=0, $R_3$ is H;

L is null or consists of 1 to 10 units, wherein each unit is a natural alpha amino acid or derived from a natural alpha amino acid, and has the formula:

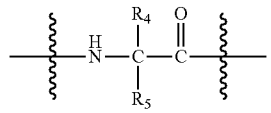

wherein $R_4$ is H; and $R_5$ is the side chain, or second hydrogen of the amino acid, or a pharmaceutically acceptable salt or prodrug thereof.

In any aspect or embodiment of the invention, a compound of the present invention comprised a chiral centre around the following chiral centre (shown at *):

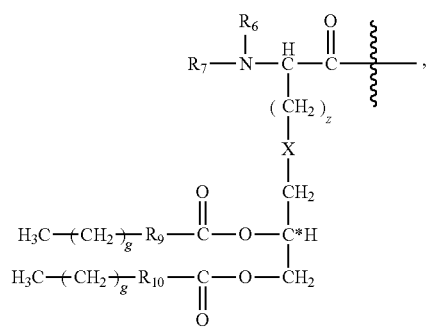

wherein the chiral centre is in the R configuration. A compound in this form may also be referred to as an R-Pam2 analogue diastereomer of a compound of the invention. This may be depicted as:

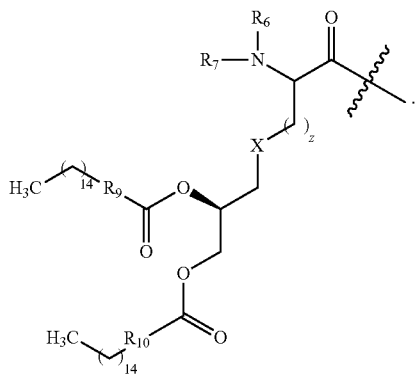

In any aspect or embodiment of the invention, a compound of the present invention comprises a chiral centre in the 2,3-bis(palmitoyloxy)propyl moiety of Pam2Cys (shown at *):

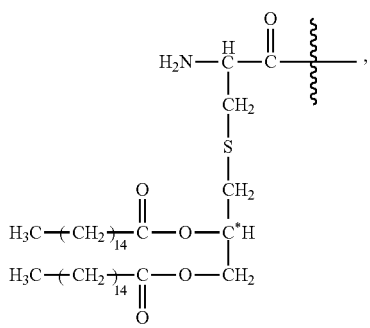

wherein the chiral centre is in the R configuration. A compound in this form may also be referred to as an R-Pam2 diastereomer of a compound of the invention. This may be depicted as:

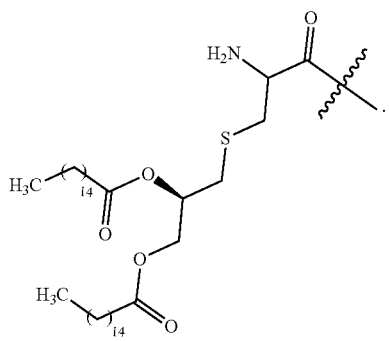

In any aspect or embodiment of the invention, a compound of the present invention comprises a chiral centre around the following chiral centre (shown at *):

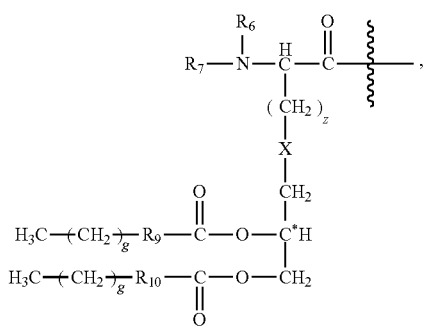

wherein the chiral centre is in the S configuration. A compound in this form may also be referred to as an S-Pam2 analogue diastereomer of a compound of the invention. This may be depicted as:

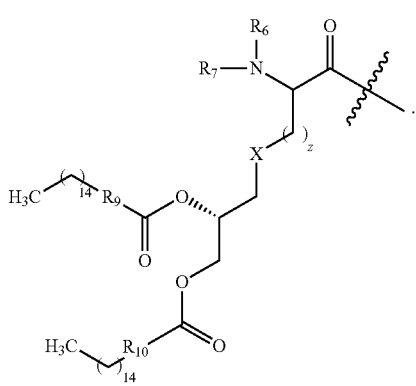

In any aspect or embodiment of the invention, a compound of the present invention comprises a chiral centre in the 2,3-bis(palmitoyloxy)propyl moiety of Pam2Cys (shown at *):

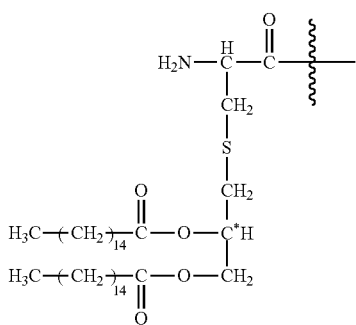

wherein the chiral centre is in the S configuration. A compound in this form may also be referred to as an S-Pam2 diastereomer of a compound of the invention. This may be depicted as:

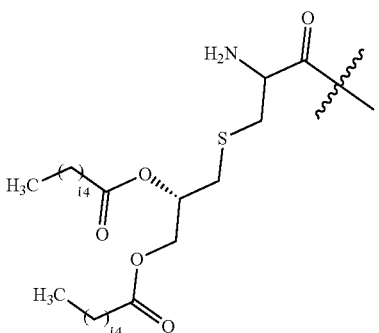

In any aspect or embodiment of the invention, a compound of the present invention comprises a chiral centre around the following chiral centre (shown at *):

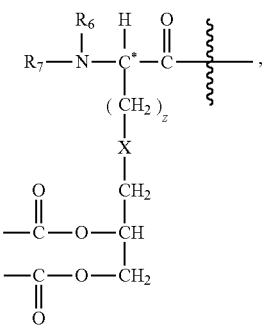

wherein the chiral centre is in the L configuration. A compound in this form may also be referred to as an L-Cys analogue diastereomer of Pam2Cys of a compound of the invention. This may be depicted as:

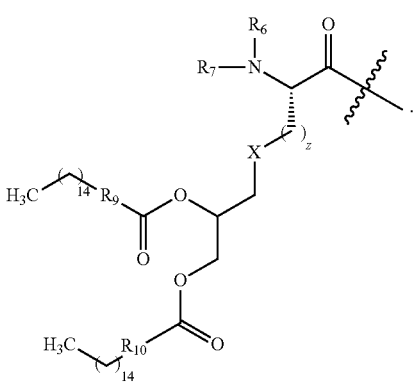

In any aspect or embodiment of the invention, a compound of the present invention comprises a chiral centre in the cysteine residue of Pam2Cys (shown at *):

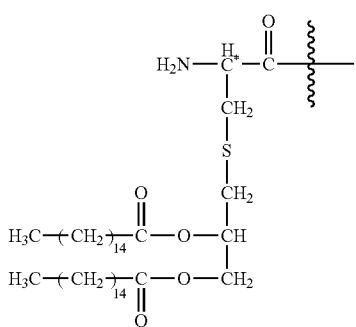

wherein the chiral centre is in the L configuration. A compound in this form may also be referred to as an L-Cys diastereomer of Pam2Cys of a compound of the invention. This may be depicted as:

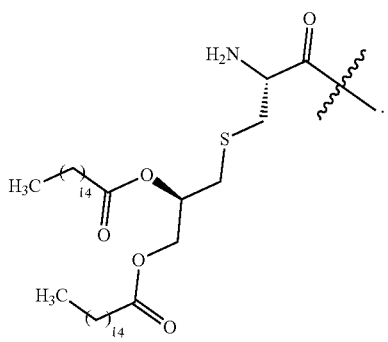

In any aspect or embodiment of the invention, a compound of the present invention comprises a chiral centre around the following chiral centre (shown at *):

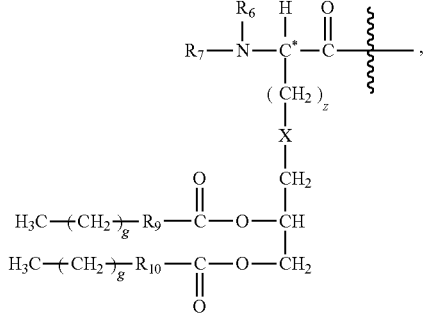

wherein the chiral centre is in the D configuration. A compound in this form may also be referred to as an D-Cys analogue diastereomer of Pam2Cys of a compound of the invention. This may be depicted as:

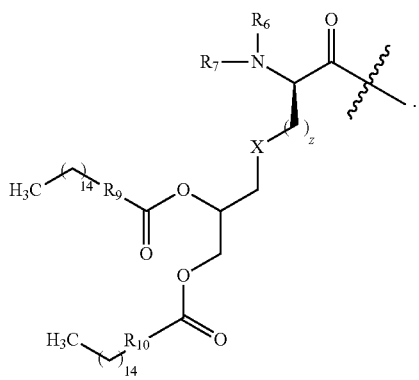

In any aspect or embodiment of the invention, a compound of the present invention comprises a chiral centre in the cysteine residue of Pam2Cys (shown at *):

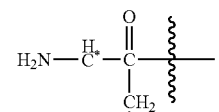

wherein the chiral centre is in the D configuration. A compound in this form may also be referred to as an D-Cys diastereomer of Pam2Cys of a compound of the invention. This may be depicted as:

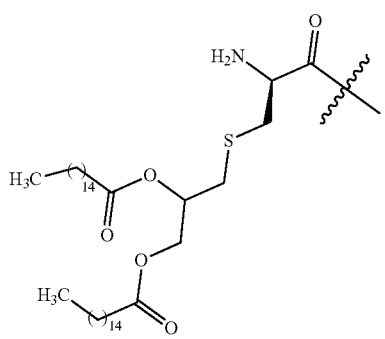 [SMILES: *C(=O)[C@H](N)CSCC(COC(=O)CC)OC(=O)CC]

In any aspect or embodiment of the invention, a compound of the present invention comprises a chiral centre in the Y moiety of the compound (shown at *):

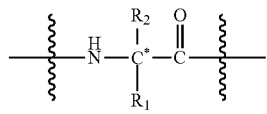

wherein the chiral centre is in the L-configuration. A compound in this form may also be referred to as an L-Y diastereomer of a compound of the invention.

In any aspect or embodiment of the invention, a compound of the present invention comprises a chiral centre in the Y moiety of the compound (shown at *):

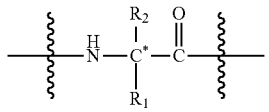

wherein the chiral centre is in the D-configuration. A compound in this form may also be referred to as an D-Y diastereomer of a compound of the invention.

In one preferred embodiment, the compound has the structure of compound (1):

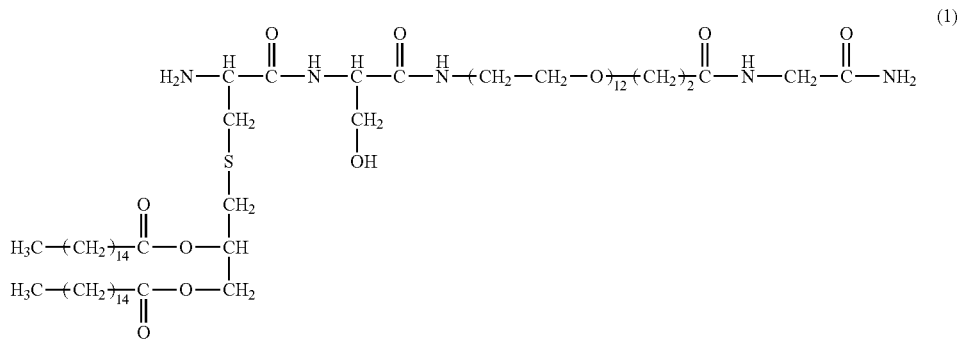

or a pharmaceutically acceptable salt or prodrug thereof.

This compound may also be referred to herein as 'Pam2Cys-Ser-PEG', or 'INNA-006'.

In other preferred embodiments, the compound is selected from the group consisting of:

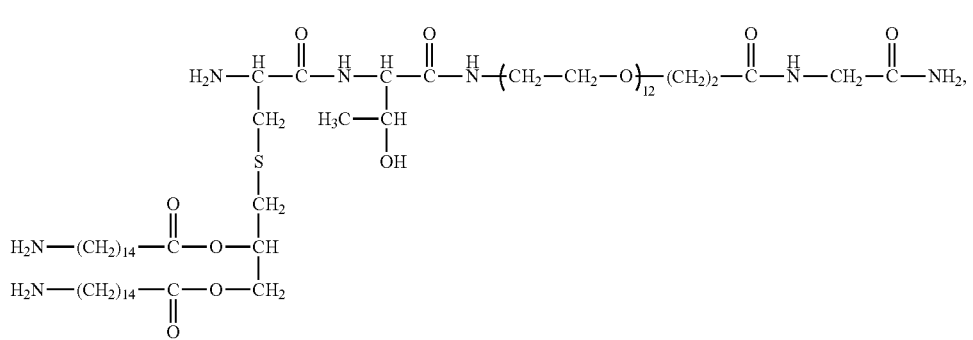

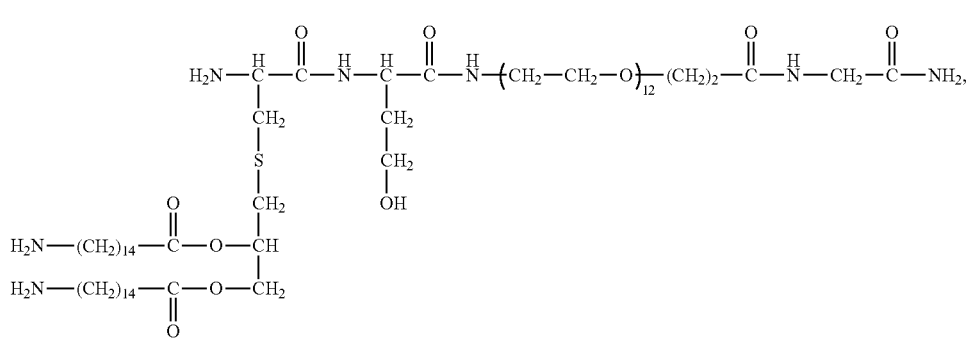

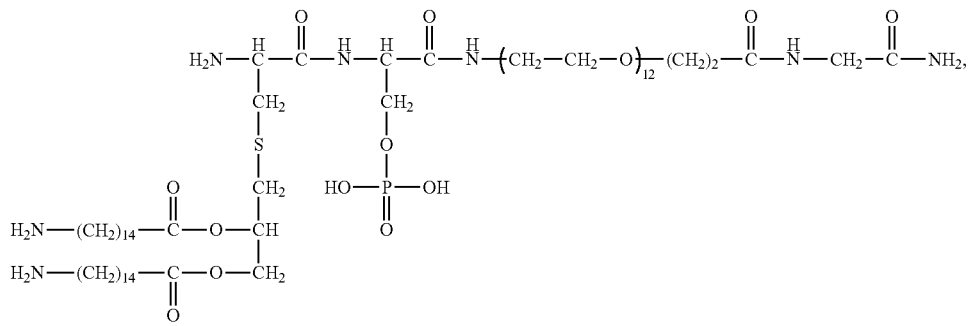
(4)
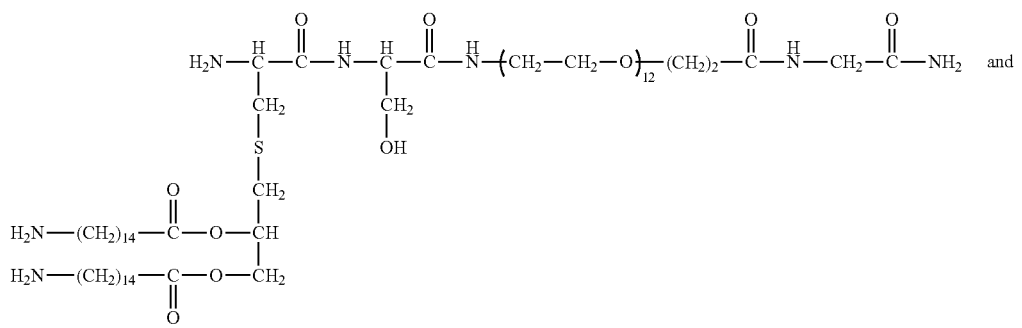
(5) and
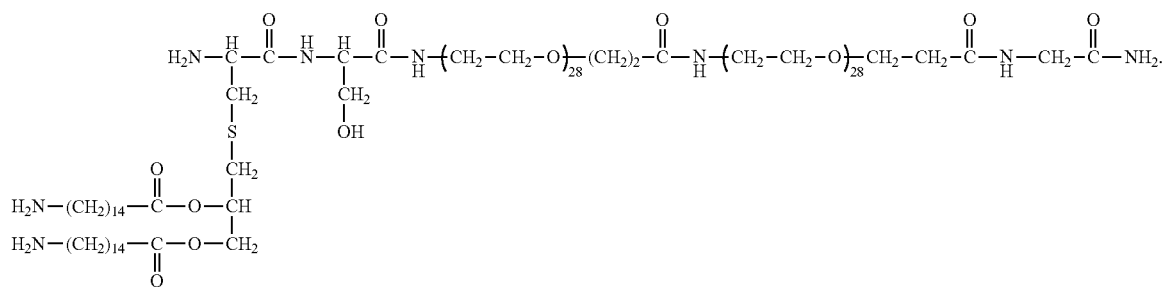
(6)
In one particularly preferred embodiment, the compound is:
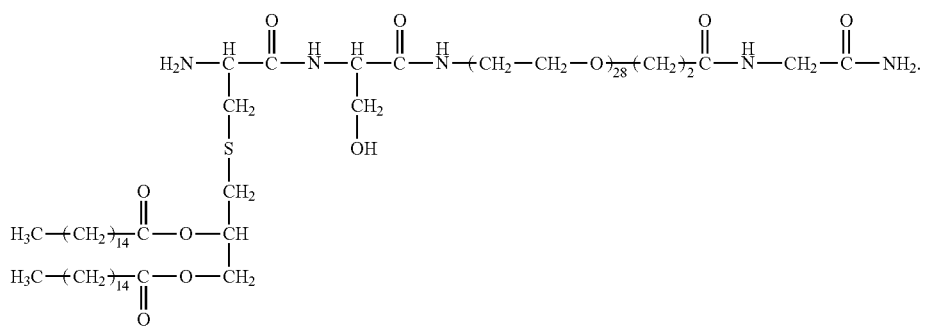
(5)

In other preferred embodiments, the compound is selected from the group consisting of:

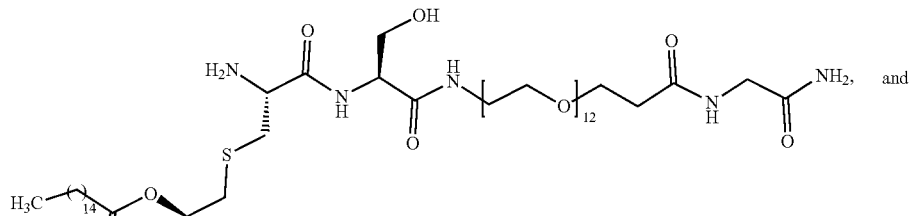

(7)

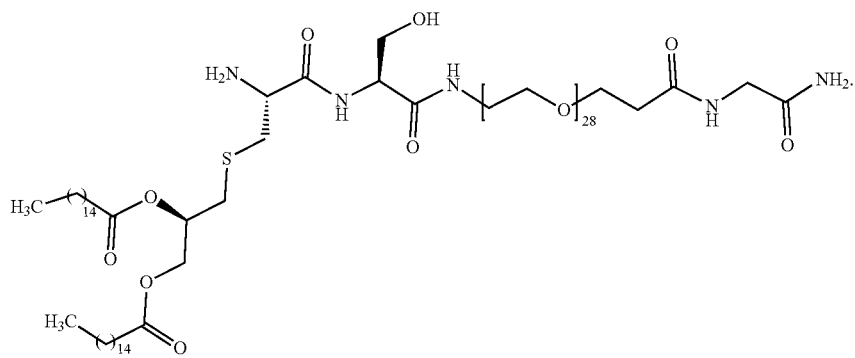

(8)

The present invention also provides for compositions comprising, consisting essentially of, or consisting of, a compound of the invention as described herein or a pharmaceutically acceptable salt or prodrug thereof, and a pharmaceutically acceptable carrier, diluent or excipient.

In one aspect, the present invention provides a method of treating and/or preventing a disease, comprising raising an innate immune response in a subject by administering an effective amount of a compound of the invention as described herein or a pharmaceutically acceptable salt or prodrug thereof to the subject in need thereof.

In another aspect, the present invention provides a method of treating and/or preventing a disease associated with, or caused by, an infectious agent, comprising administering to a subject in need thereof an effective amount of a compound of the invention as described herein or a pharmaceutically acceptable salt or prodrug thereof.

In another aspect, the present invention provides a method of treating and/or preventing a respiratory disease or condition associated with a viral or bacterial infection, comprising administering to a subject in need thereof a compound of the invention as described herein or a pharmaceutically acceptable salt or prodrug thereof.

In another aspect, the present invention provides a method of treating and/or preventing a respiratory infection, comprising administering to a subject in need thereof a compound of the invention as described herein or a pharmaceutically acceptable salt or prodrug thereof.

In another aspect, the present invention provides a method for reducing airway inflammation, comprising administering to a subject in need thereof a compound of the invention as described herein or a pharmaceutically acceptable salt or prodrug thereof.

The present invention also provides a method of improving the ability of a subject to control a respiratory disease or condition during a respiratory viral infection, the method comprising administering to a subject in need thereof a compound of the invention as described herein or a pharmaceutically acceptable salt or prodrug thereof.

The present invention also provides a method of treating and/or preventing a disease or condition associated with the TLR2 receptor, the method comprising administering to a subject in need thereof a compound of the invention as described herein or a pharmaceutically acceptable salt or prodrug thereof.

In another aspect, the present invention provides for use of a compound of the invention as described herein or a pharmaceutically acceptable salt or prodrug thereof in the preparation of a medicament for raising an innate immune response in a subject.

In another aspect, the present invention provides for use of a compound of the invention as described herein or a pharmaceutically acceptable salt or prodrug thereof in the preparation of a medicament for treating and/or preventing a disease caused by an infectious agent.

In another aspect, the present invention further provides for use of a compound of the invention as described herein or a pharmaceutically acceptable salt or prodrug thereof in the preparation of a medicament for treating and/or preventing a respiratory disease or condition associated with a viral or bacterial infection in a subject.

In another aspect, the present invention further provides for use of a compound of the invention as described herein or a pharmaceutically acceptable salt or prodrug thereof in the preparation of a medicament for treating and/or preventing a respiratory infection in a subject.

In another aspect, the present invention further provides use of a compound of the invention as described herein or a pharmaceutically acceptable salt or prodrug thereof in the preparation of a medicament for reducing airway inflammation.

In another aspect, the present invention further provides use of a compound of the invention as described herein or a pharmaceutically acceptable salt or prodrug thereof in the preparation of a medicament for improving the ability of a subject to control a respiratory disease or condition during a respiratory viral infection.

In another aspect, the present invention further provides use of a compound of the invention as described herein or a pharmaceutically acceptable salt or prodrug thereof in the preparation of a medicament for treating and/or preventing a disease or condition associated with the TLR2 receptor.

In one aspect, the present invention provides for use of a compound of the invention as described herein or a pharmaceutically acceptable salt or prodrug thereof, for raising an innate immune response in a subject.

In another aspect, the present invention provides for use of a compound of the invention as described herein or a pharmaceutically acceptable salt or prodrug thereof, for preventing a disease caused by an infectious agent, in a subject.

In another aspect, the present invention provides for use of a compound of the invention as described herein or a pharmaceutically acceptable salt or prodrug thereof, for treating and/or preventing a respiratory disease or condition associated with a viral or bacterial infection in a subject.

In another aspect, the invention provides use of a compound of the invention as described herein or a pharmaceutically acceptable salt or prodrug thereof for reducing airway inflammation in a subject.

In another aspect, the invention provides use of a compound of the invention as described herein or a pharmaceutically acceptable salt or prodrug thereof for controlling a respiratory disease or condition during a respiratory viral infection in a subject.

In another aspect, the invention provides use of a compound of the invention as described herein or a pharmaceutically acceptable salt or prodrug thereof for treating and/or preventing a disease or condition associated with the TLR2 receptor.

The present invention also provides a kit for use, or when used, in a method of the invention, the kit comprising, consisting essentially of or consisting of:

a compound of the invention as described herein; and optionally written instructions describing the use of the compound in a method of the invention.

In any aspect of the invention, preferably the compound of the invention as described herein is compound (1), (2), (3), (4), (5), (6), (7), (8), (9), (10), (11), (12), (13) or (14). Preferably, the compound is compound (1), (5), (7) or (8). Even more preferably, the compound is (7) or (8).

In yet another aspect, the present invention provides a process for preparing a compound of formula (I):

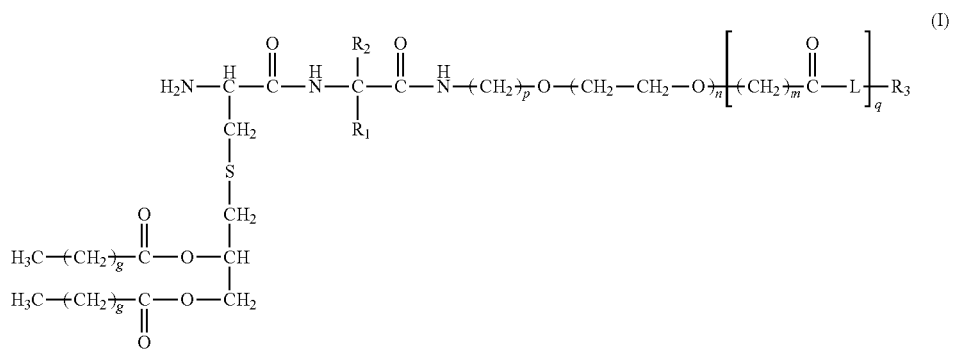

wherein n is 3 to 100;

m is 1, 2, 3 or 4;

each g is independently 10, 11, 12, 13, 14, 15, 16, 17 or 18;

p is 2, 3 or 4;

q is null or 1;

$R_1$ and $R_2$ are independently selected from the group consisting of H, —$CH_2OH$, —$CH_2CH_2OH$, —CH($CH_3$)OH and —$CH_2OPO(OH)_2$, wherein any one of the alkyl hydrogens can be replaced with a halogen, and wherein $R_1$ and $R_2$ are not both H;

wherein when q=1, $R_3$ is —$NH_2$ or —OH;

wherein when q=0, $R_3$ is H;

L is null or consists of 1 to 10 units, wherein each unit is a natural alpha amino acid or derived from a natural alpha amino acid, and has the formula:

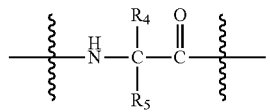

wherein $R_4$ is H; and $R_5$ is the side chain, or second hydrogen of the amino acid, the process comprising a) coupling PG-NH—$(PEG)_n$-COOH to a solid phase support;

b) removing PG;

c) coupling PG1-NH—$CR_1R_2$—COOH to the PEG;

d) removing PG1;

e) coupling PG2-Dhc-OH;

f) palmitoylation of the Dhc
g) removing PG2; and
h) removing the compound from the solid phase support,
wherein PG is a protecting group.

In one embodiment, the present invention provides a process for preparing a compound with the structure:

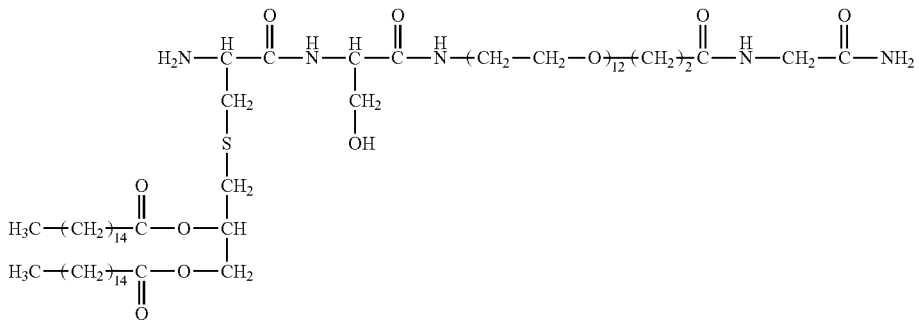 [SMILES: CCC(=O)OCC(CSCC(N)C(=O)NC(CO)C(=O)NCCOCC(=O)NCC(N)=O)OC(=O)CC]

the process comprising
a) coupling Fmoc-Gly-OH to a TentaGel S RAM solid phase support;
b) removing the Fmoc group from the Gly;
c) coupling Fmoc-NH—(PEG)$_{11}$-COOH of the structure

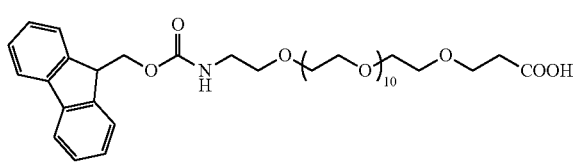

to the Gly;
d) removing the Fmoc group from the PEG;
e) coupling Fmoc-Ser-OH to the PEG;
f) removing the Fmoc group from the Ser;
g) coupling Fmoc-Dhc-OH to the Ser;
h) palmitoylation of the Dhc
i) removing the Fmoc group from the Dhc; and
j) removal of the compound from the solid phase support.

In another aspect, the present invention provides a compound with the structure:

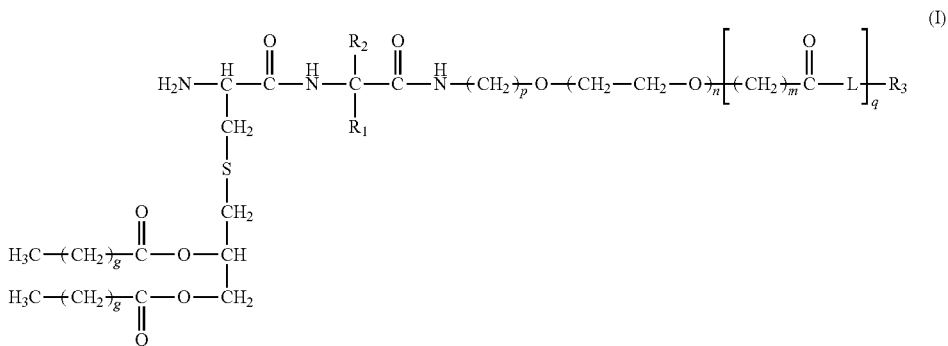

wherein n is 3 to 100;

m is 1, 2, 3 or 4;

each g is independently 10, 11, 12, 13, 14, 15, 16, 17 or 18;

p is 2, 3 or 4;

q is null or 1;

$R_1$ and $R_2$ are independently selected from the group consisting of H, —$CH_2OH$, —$CH_2CH_2OH$, —CH($CH_3$)OH and —$CH_2OPO(OH)_2$, wherein any one of the alkyl hydrogens can be replaced with a halogen, and wherein $R_1$ and $R_2$ are not both H;

wherein when q=1, $R_3$ is —$NH_2$ or —OH;

wherein when q=0, $R_3$ is H;

L is null or consists of 1 to 10 units, wherein each unit is a natural alpha amino acid or derived from a natural alpha amino acid, and has the formula:

$$\begin{array}{c} R_4 \quad O \\ | \quad \| \\ -N-C-C- \\ H \quad | \\ \quad R_5 \end{array}$$

wherein $R_4$ is H; and $R_5$ is the side chain, or second hydrogen of the amino acid, prepared by a process described herein.

In yet another aspect, the present invention provides a process for preparing a compound of formula (V):

$$H_2N-\overset{H}{\underset{CH_2}{\overset{|}{C}}}-\overset{O}{\overset{\|}{C}}-\overset{H}{\underset{R_1}{\overset{|}{N}}}-\overset{R_2}{\underset{}{\overset{|}{C}}}-\overset{O}{\overset{\|}{C}}-\overset{H}{N}-(CH_2)_p-O-(CH_2-CH_2-O)_n-(CH_2)_h-\overset{O}{\overset{\|}{C}}-\overset{H}{N}-(CH_2)_h-O-(CH_2-CH_2-O)_k-[(CH_2)_m-\overset{O}{\overset{\|}{C}}-L]_q-R_3$$

$$H_3C-(CH_2)_g-\overset{O}{\overset{\|}{C}}-O-\overset{}{\underset{}{CH}}$$
$$H_3C-(CH_2)_g-\overset{}{\underset{O}{\overset{\|}{C}}}-O-CH_2$$

wherein n is 3 to 100;

k is 3 to 100;

m is 1, 2, 3 or 4;

each g is independently 10, 11, 12, 13, 14, 15, 16, 17 or 18;

p is 2, 3 or 4;

t is 2, 3 or 4;

h is 1, 2, 3 or 4;

q is null or 1;

$R_1$ and $R_2$ are independently selected from the group consisting of H, —$CH_2OH$, —$CH_2CH_2OH$, —CH($CH_3$)OH and —$CH_2OPO(OH)_2$, wherein any one of the alkyl hydrogens can be replaced with a halogen, and wherein $R_1$ and $R_2$ are not both H;

wherein when q=1, $R_3$ is —$NH_2$ or —OH;

wherein when q=0, $R_3$ is H;

L is null or consists of 1 to 10 units, wherein each unit is a natural alpha amino acid or derived from a natural alpha amino acid, and has the formula:

$$\begin{array}{c} R_4 \quad O \\ | \quad \| \\ -N-C-C- \\ H \quad | \\ \quad R_5 \end{array}$$

wherein $R_4$ is H; and $R_5$ is the side chain, or second hydrogen of the amino acid, the process comprising a) coupling PG-NH—$(PEG)_n$-COOH to a solid phase support;

b) removing PG;

c) coupling PG1-NH—$(PEG)_n$-COOH;

d) removing PG1;

e) coupling PG2-NH—$CR_1R_2$—COOH to the PEG;

f) removing PG2;

g) coupling PG3-Dhc-OH;

h) palmitoylation of the Dhc i) removing PG3; and j) removing the compound from the solid phase support, wherein PG is a protecting group. Preferably, in $(PEG)_n$, n is 27.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

Figure 3:
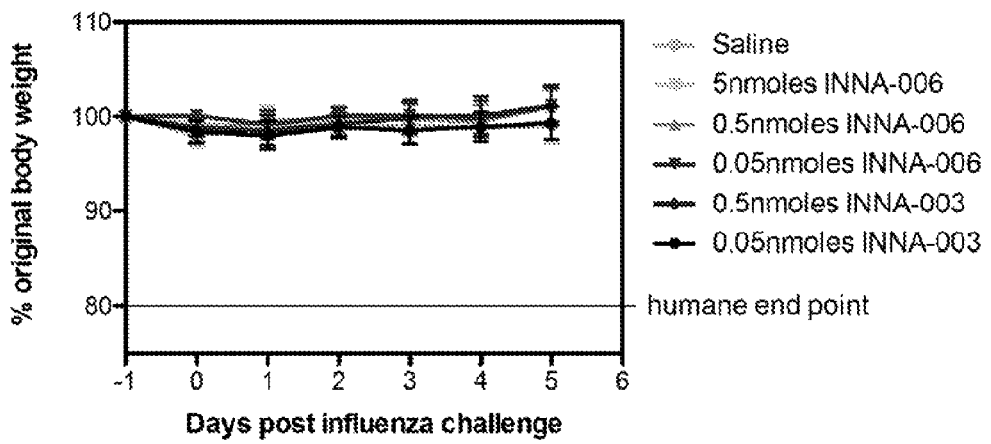

FIG. 3: Percentage change in body weight of C57BL/6 mice receiving URT treatment with INNA-003 or INNA-006. Groups of C57BL/6 mice (n=10) were inoculated intranasally with varying doses of INNA-003 or INNA-006 in 10 µl of saline while anaesthetised. After 24 hours, mice were challenged intranasally with 500 pfu of Udorn influenza virus in 10 µl of PBS while anaesthetised. Error bars depict s.d. and the horizontal line at 80% represents the limit of weight loss i.e. 20% maxmum according to the AEC.

Figure 4:
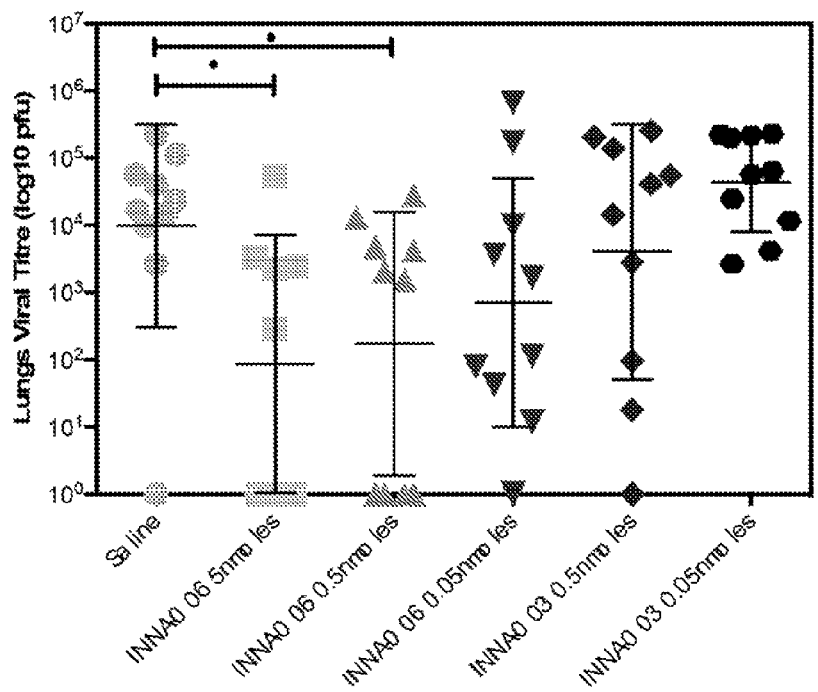

FIG. 4: Prophylactic, URT treatment with INNA-003 or INNA-006 prior to URT challenge with Udorn virus. Groups of 10 C57BL/6 mice were inoculated intranasally with varying doses of INNA-003 or INNA-006 in 10 µl of saline while anaesthetised. After 24 hours, mice were challenged intranasally with 500 pfu of Udorn influenza virus in 10 µl of PBS while anaesthetised. Viral titers in lungs were determined by plaque formation in MDCK cell monolayers 5 days after viral challenge. Error bars depict s.d. and statistical significance was also assessed using a unpaired t test and is denoted by circles (\* P<0.0332).The INNA-006 group represents 9 animals only that showed detectable levels of virus in the nasal turbinates.

Figure 5:
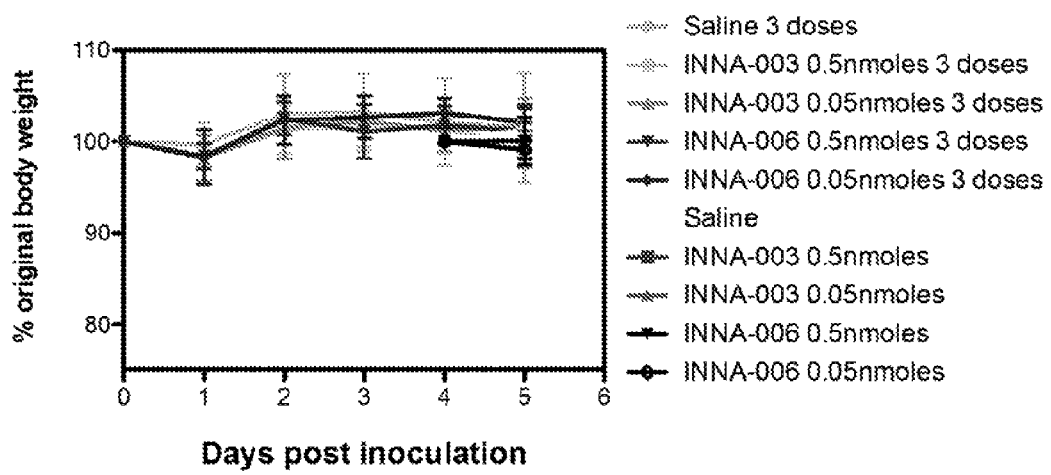

FIG. 5: Percentage change in body weight of mice receiving URT treatment with multiple doses of INNA-003 or INNA-006. Groups of 5 C57BL/6 mice were treated intranasally with either 3 doses of agonists on day 0, 2 and 4 or a single dose on day 4. Each dose was administered to anaesthetized mice and contained either with 0.5 nmoles or 0.05 nmoles doses of INNA-003 or INNA-006 in 10 µl of saline. All mice were weighed daily. Error bars depict s.d.

Figure 6:
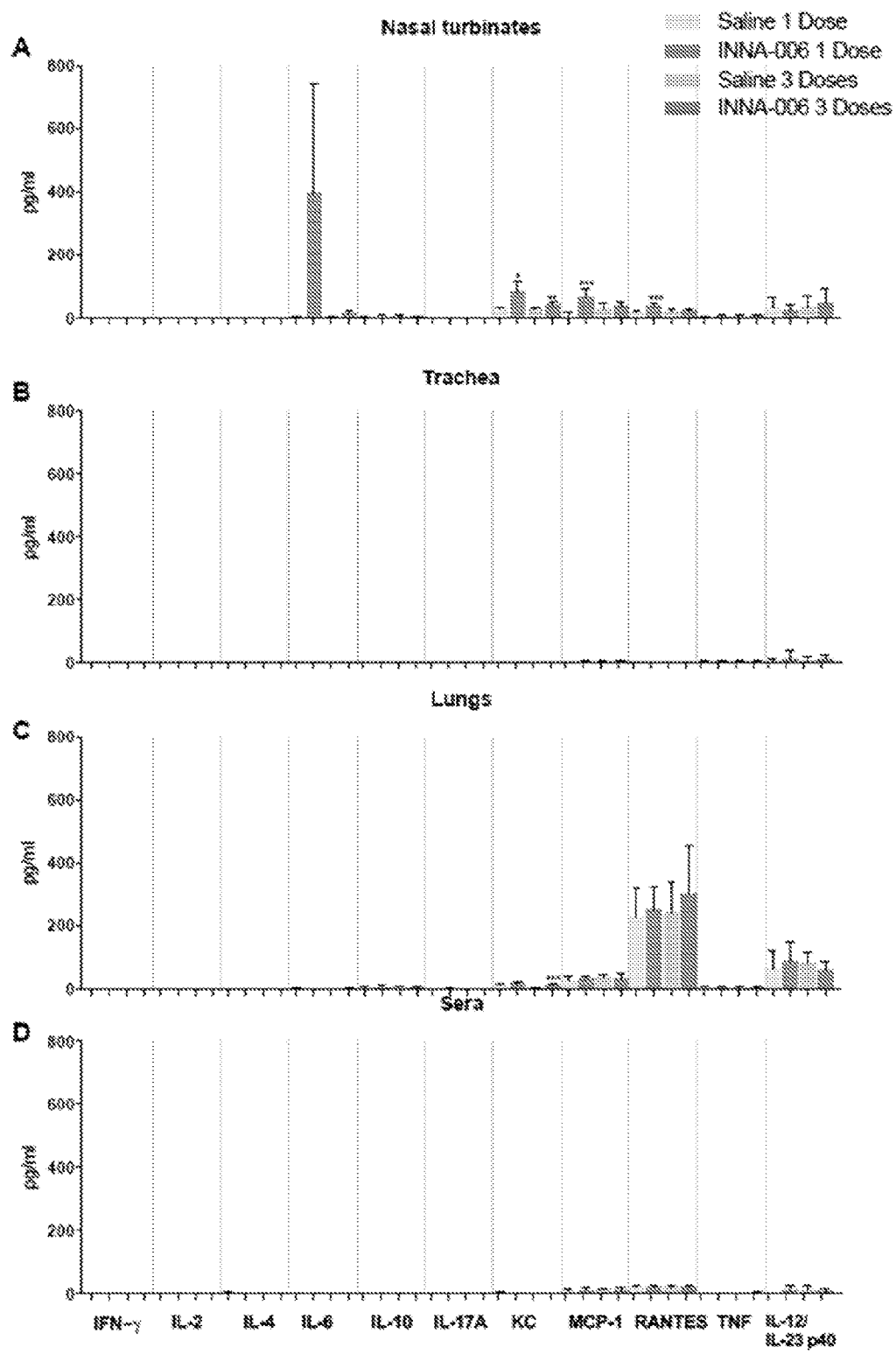

FIG. 6. Cytokine/Chemokine profiles in nasal turbinates, trachea, lungs and sera of mice receiving INNA-006 (0.5 nmole) by the URT route. Groups of 5 C57BL/6 mice were inoculated intranasally with either 1 dose or 3 doses of agonists over a 5-days period with 0.5 nmoles doses of INNA-006 in 10 ul of saline under isoflurane anesthesia. Mice were killed 24 hours after the last dose administered and cytokine/chemokine profiles in the (A) nasal turbinates, (B) trachea, (C) lungs, and (D) sera were determined by cytometric bead array. Error bars depict s.d. Statistical significance (\*\*\*P=0.0002, \*\*P=0.0021 & \*P=0.0322) is denoted by asterisks and was obtained using a one-way ANOVA with Tukey's test comparing to saline control groups. The results of the four treatments listed in the legend from top to bottom are shown left to right on the horizontal axis.

Figure 7:
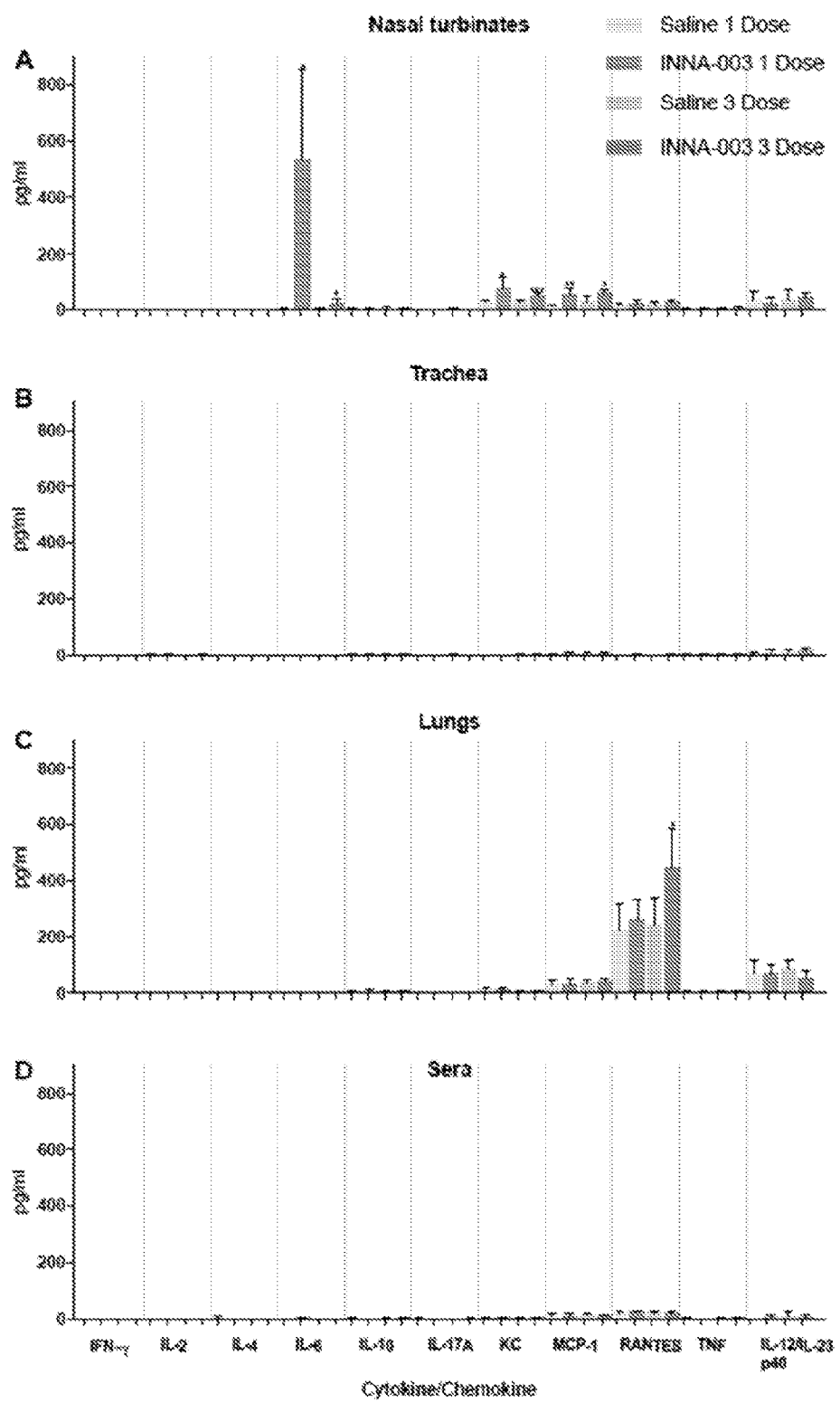

FIG. 7. Cytokine/Chemokine profiles in nasal turbinates, trachea, lungs and sera of mice receiving of INNA-003 (0.5 nmole) by the URT route. Groups of 5 C57BL/6 mice were inoculated intranasally with either 1 dose or 3 doses of agonists over a 5-days period with 0.5 nmoles doses of INNA-003 in 10 ul of saline under isoflurane anesthesia. Mice were killed 24 hours after the last dose administered and cytokine/chemokine profiles in the (A) nasal turbinates, (B) trachea, (C) lungs, and (D) sera were determined by cytometric bead array. Error bars depict s.d. Statistical significance (\*\*\*P=0.0002, \*\*P=0.0021 & \*P=0.0322) is denoted by asterisks and was obtained using a one-way ANOVA with Tukey's test comparing to saline control groups. The results of the four treatments listed in the legend from top to bottom are shown left to right on the horizontal axis.

Figure 8:
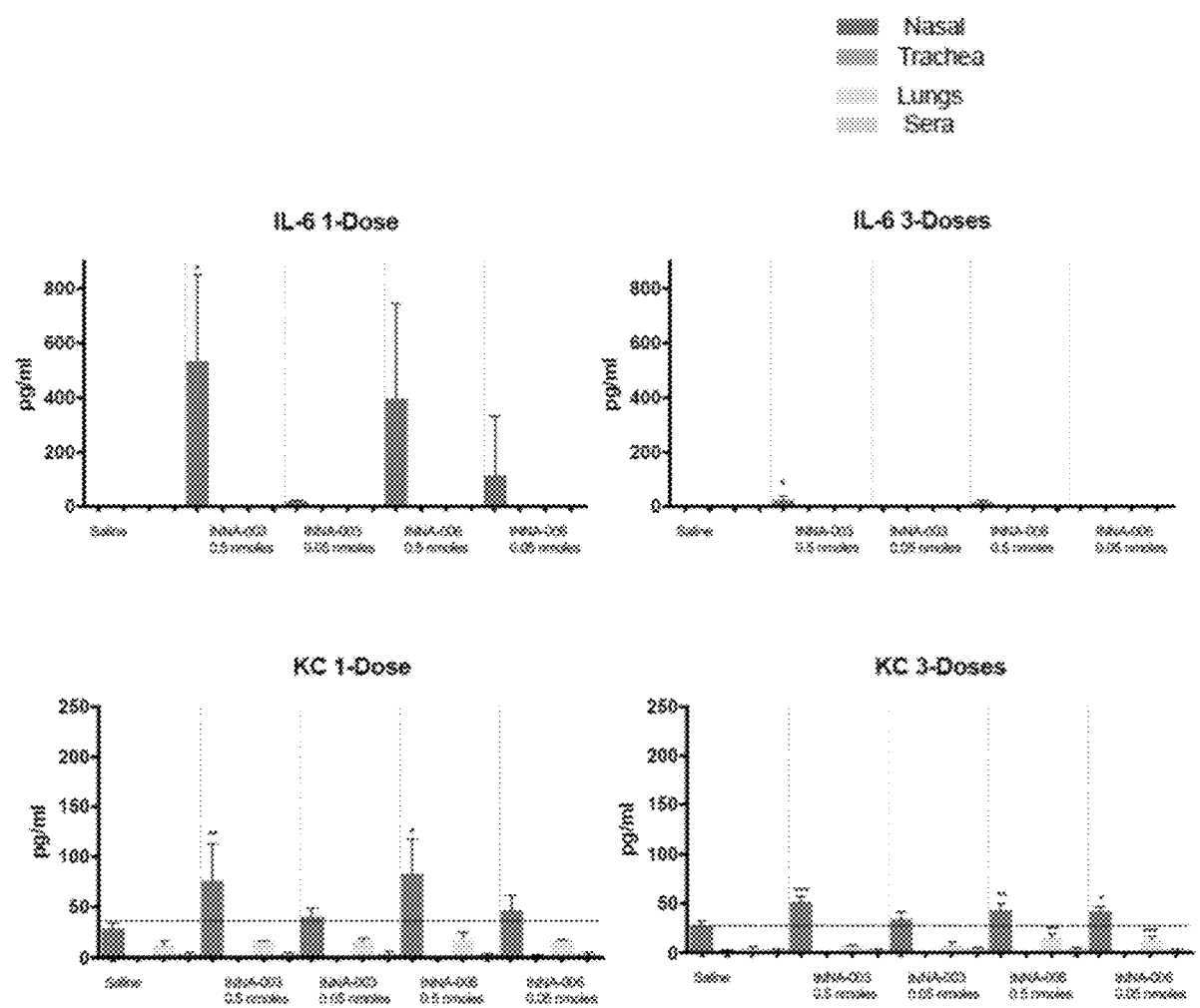

FIG. 8. Comparison of single and triple dose regimes of INNA-003 and INNA-006 on cytokine/chemokine profiles in nasal turbinate, trachea, lungs and sera. Groups of 5 C57BL/6 mice were inoculated intranasally with either 1 dose or 3 doses of INNA-003 (0.5 nmoles or 0.05 nmoles) or INNA-006 (0.5 nmoles or 0.05 nmoles) in 10 µl of saline while anaesthetised with isoflurane. Mice were killed 24 hours after the last dose of TLR2 agonist and the level of cytokines in the nasal turbinate, trachea, lungs, and sera determined by cytometric bead array. Error bars indicate the s.d. and statistical significance (\*\*\*P=0.0002, \*\*P=0.0021 & \*P=0.0322) is denoted by asterisks obtained using a oneway ANOVA with Tukey's test which was obtained by comparison with saline control groups. The results of the four treatments listed in the legend from top to bottom are shown left to right on the horizontal axis.

Figure 9:
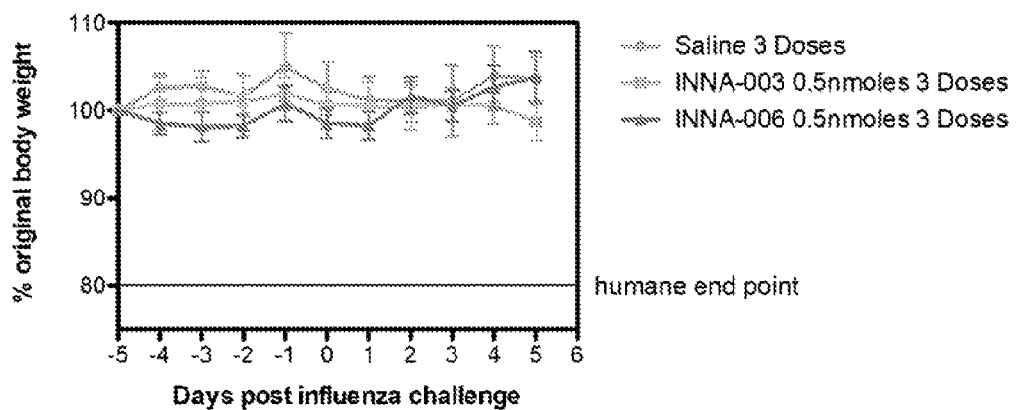

FIG. 9: Percentage change in body weight of mice following multiple treatments with INNA-003 or INNA-006 followed by challenge with Udorn influenza virus. Groups of 5 C57BL/6 mice were inoculated intranasally with 3 doses of agonist over a 5-day period with 0.5 nmole doses of INNA-003 or INNA-006 in 10 µl of saline while anaesthetised. 24 hours after the last dose, mice were challenged intranasally with 500 pfu of Udorn influenza virus in 10 µl of saline while anaesthetized. Error bars depict s.d. and the horizontal line at 80% represents the limit of weight loss i.e. 20% acceptable according to the AEC.

Figure 10:
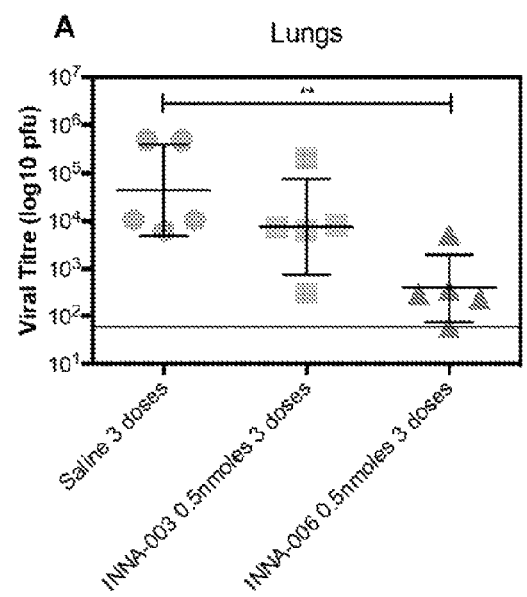

FIG. 10: Effects on viral titre in the lungs of mice treated prophylactively with multiple doses of INNA-003 or INNA-006. Groups of 5 C57BL/6 mice were inoculated intranasally with 3 doses of agonist over a 5-day period with 0.5 nmoles doses of INNA-003 or INNA-006 in 10 µl of saline while anaesthetized. 24 hours after the last dose, mice were challenged intranasally with 500 pfu of Udorn influenza virus in 10 µl of saline while anaesthetized. Viral titers in the lungs were determined by plaque formation in MDCK cells at day 5 post-challenge. Error bars depict s.d. and statistical significance (\*\*P=0.0021) is denoted by asterisks and was obtained using a one-way ANOVA with Tukey comparing all column test.

Figure 11:
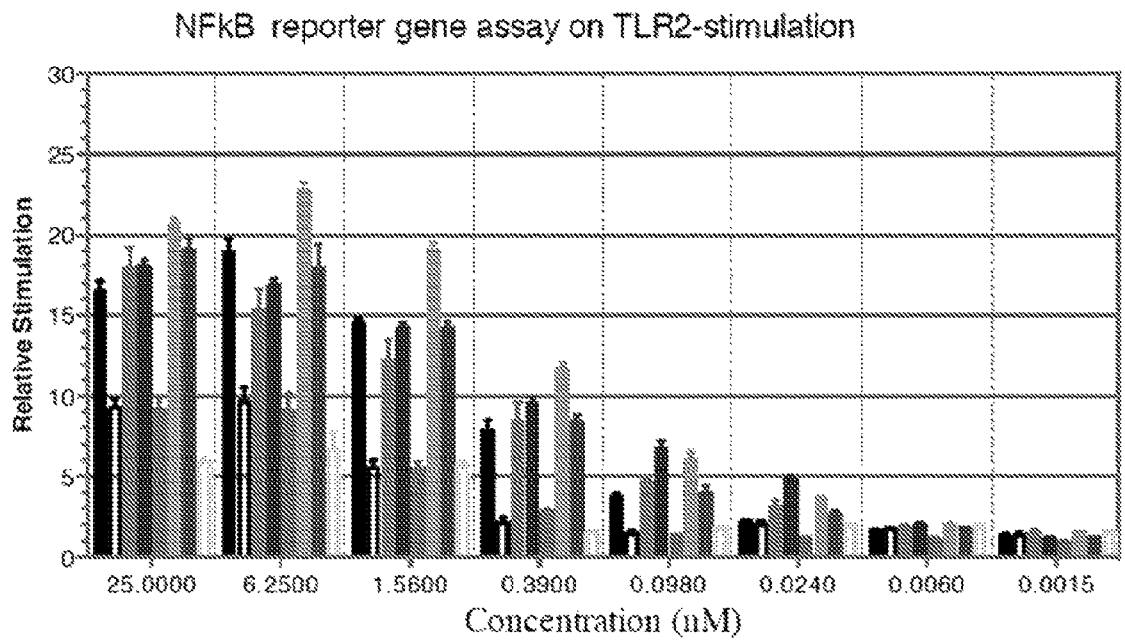

FIG. 11. Comparison of the abilities of various compounds to stimulate luciferase activity in an NF-κB cell-based reporter system. Columns left to right are: INNA-006 (or compound (1)); INNA-013 (or compound (4)); INNA-014 (or compound (3)); INNA-015 (or compound (2)); INNA-010; INNA-011 (or compound (5)); INNA-012 (or compound (6)); and INNA-009.

Figure 12:
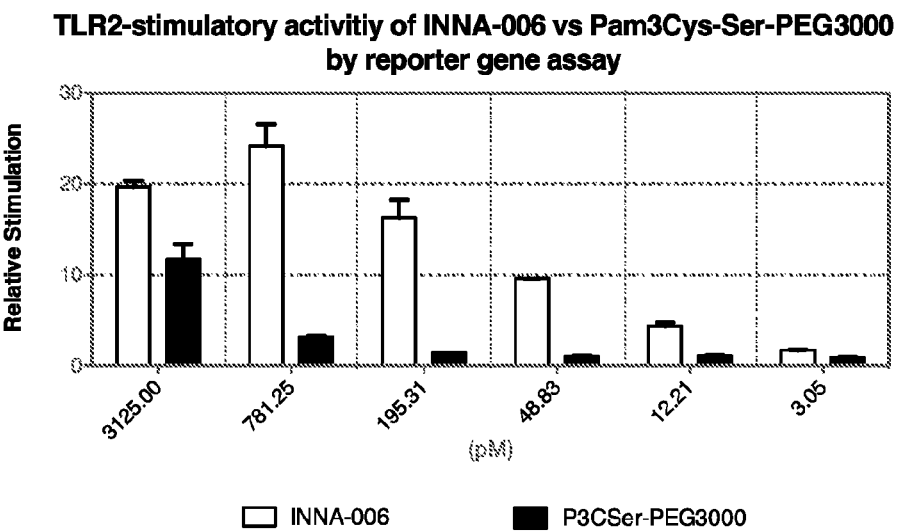

FIG. 12: Comparison of the abilities of INNA-006 or Pam3Cys-Ser-PEG3000 to stimulate luciferase activity in an NF-κB cell-based reporter system.

Figure 13:
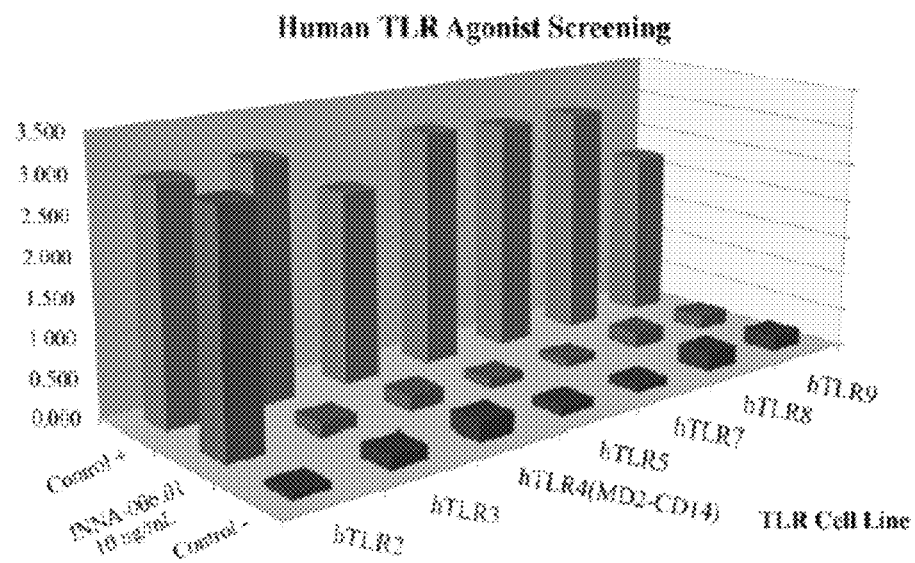

FIG. 13: Representative data indicating specific TLR-2 activation by INNA-006.

Figure 14:
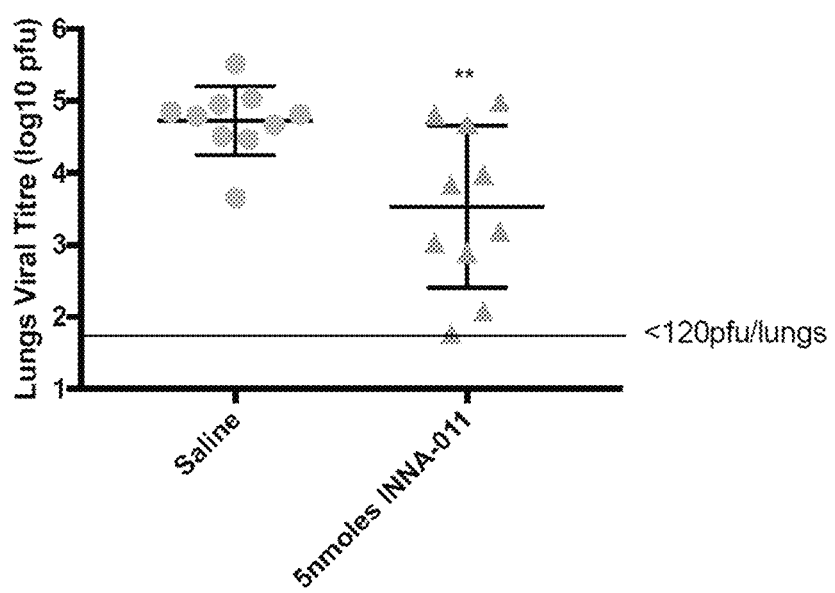

FIG. 14: Viral titres in lungs of mice following prophylactic treatment with INNA-011 prior to challenge with Udorn virus. Groups of 10 C57BL/6 mice were treated intranasally with 5 nmoles of INNA-011 in 10 µl of saline or with saline alone 7 days before challenge with Udorn virus. Mice were challenged intranasally with 500 pfu of Udorn influenza virus in 10 µl of PBS under isoflurane anaesthesia. Viral titres in the lungs were determined by plaque formation in MDCK cell monolayers 5 days after viral challenge. Error bars depict s.d. Statistical significance (**P=0.0021) is denoted by asterisks and was obtained using a one-way ANOVA with Tukey's test comparing all groups.

Figure 15A:
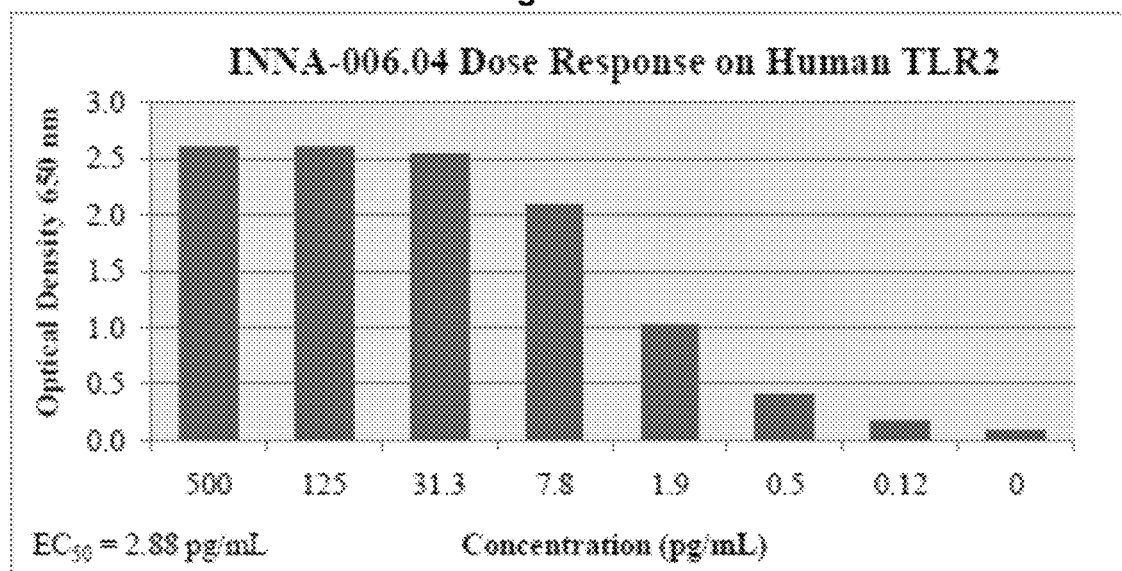

FIG. 15A: Human TLR2 Dose Response for INNA-006.04.

Figure 15B:
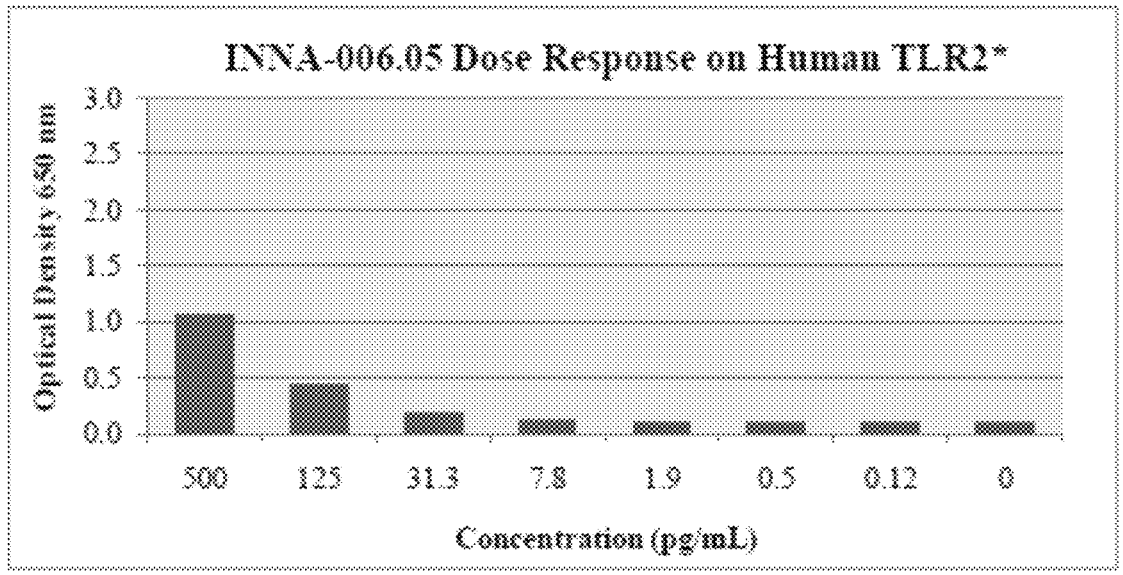

FIG. 15B: Human TLR2 Dose Response for INNA-006.05.

Figure 15C:
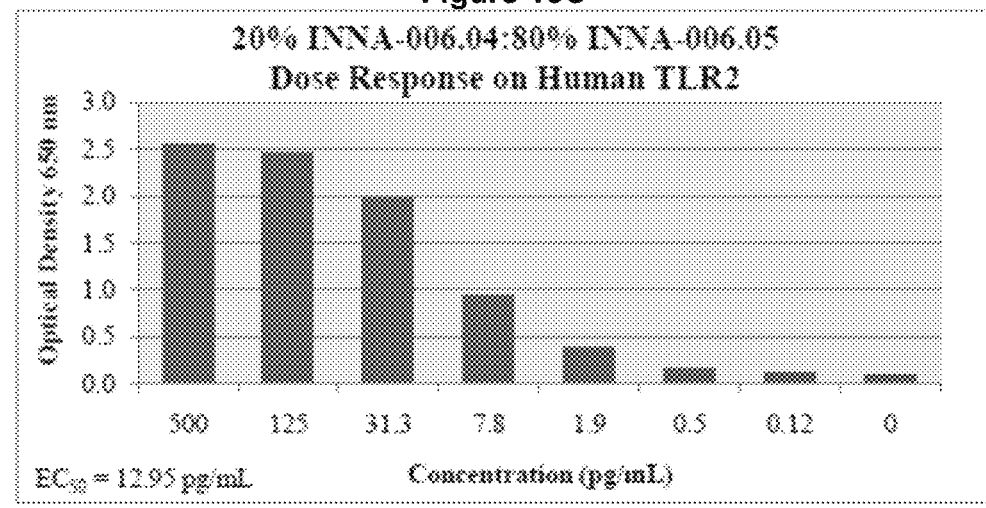

FIG. 15C: Human TLR2 Dose Response for 20% INNA-006.04 and 80% INNA-006.05.

Figure 15D:
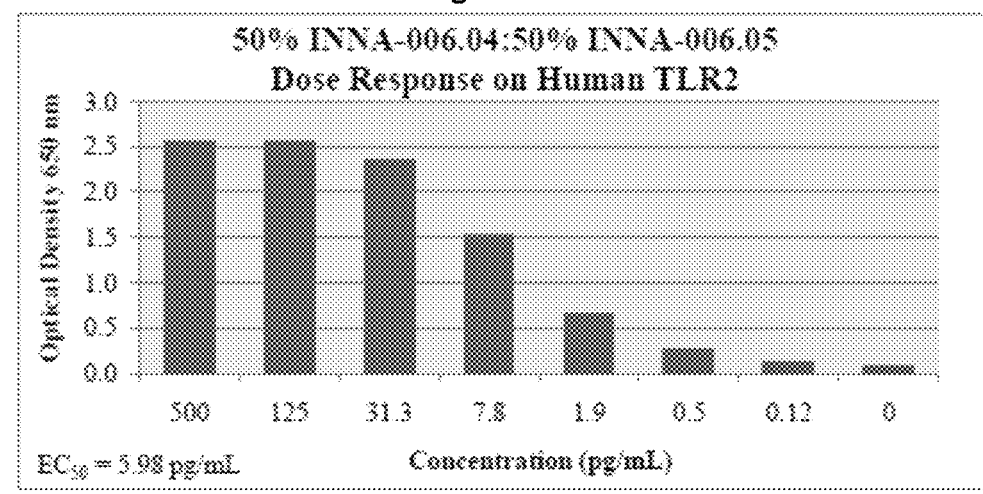

FIG. 15D: Human TLR2 Dose Response for 50% INNA-006.04 and 50% INNA-006.05.

Figure 15E:
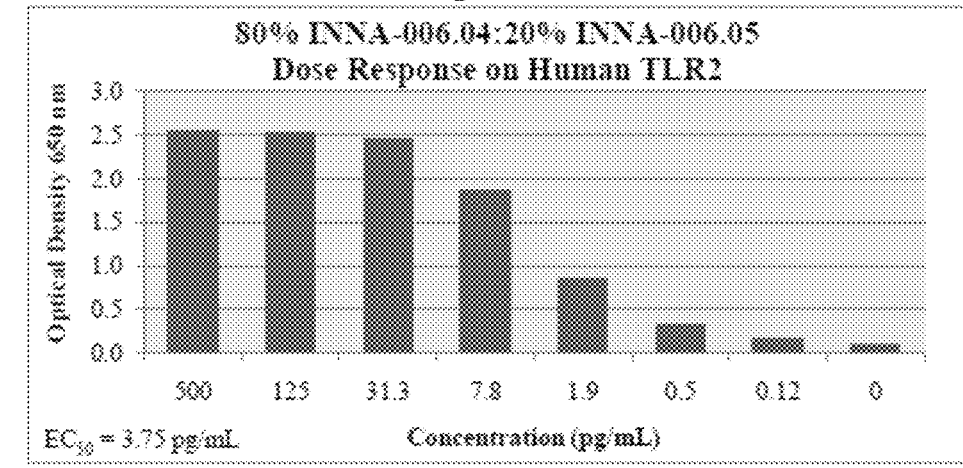

FIG. 15E: Human TLR2 Dose Response for 80% INNA-006.04 and 20% INNA-006.05.

Figure 16A:
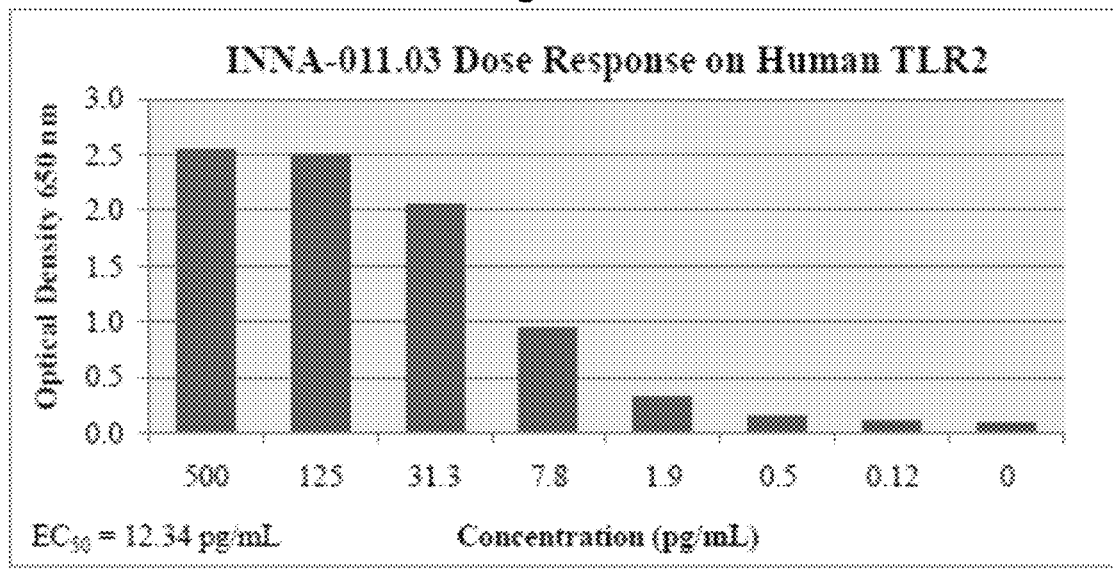

FIG. 16A: Human TLR2 Dose Response for INNA-011.03.

Figure 16B:
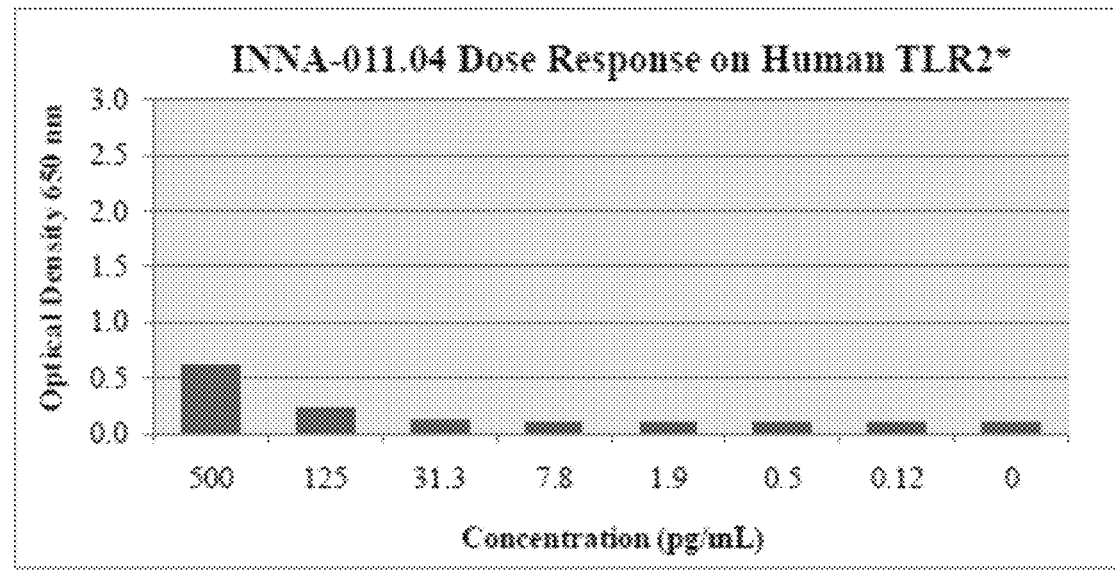

FIG. 16B: Human TLR2 Dose Response for INNA-011.04.

Figure 16C:
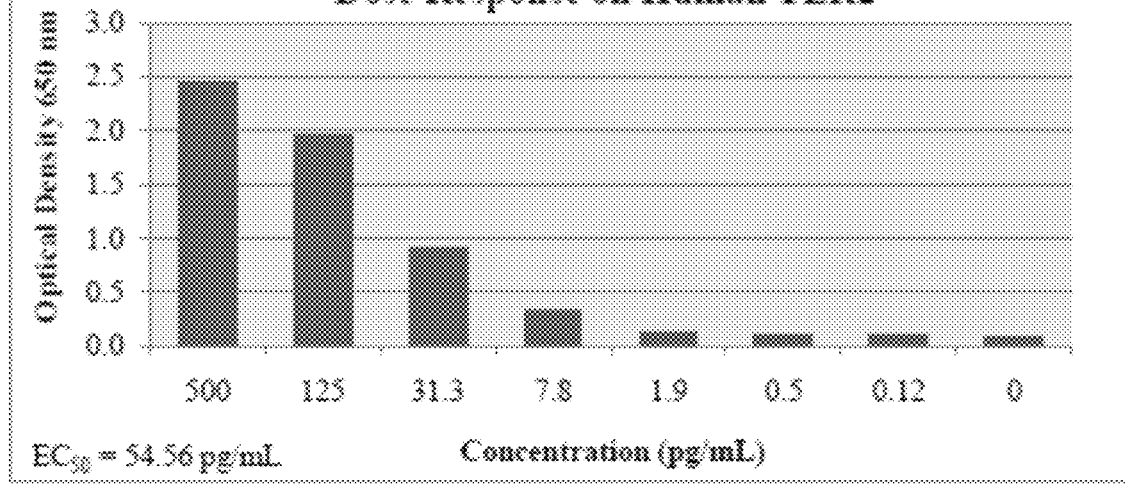

FIG. 16C: Human TLR2 Dose Response for 20% INNA-011.03 and 80% INNA-011.04.

Figure 16D:
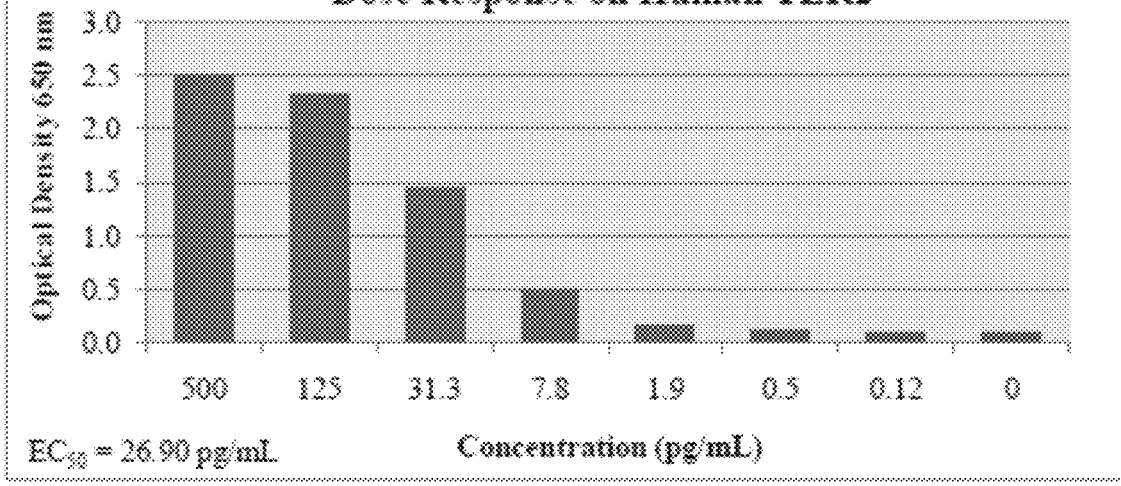

FIG. 16D: Human TLR2 Dose Response for 50% INNA-011.03 and 50% INNA-011.04.

Figure 16E:
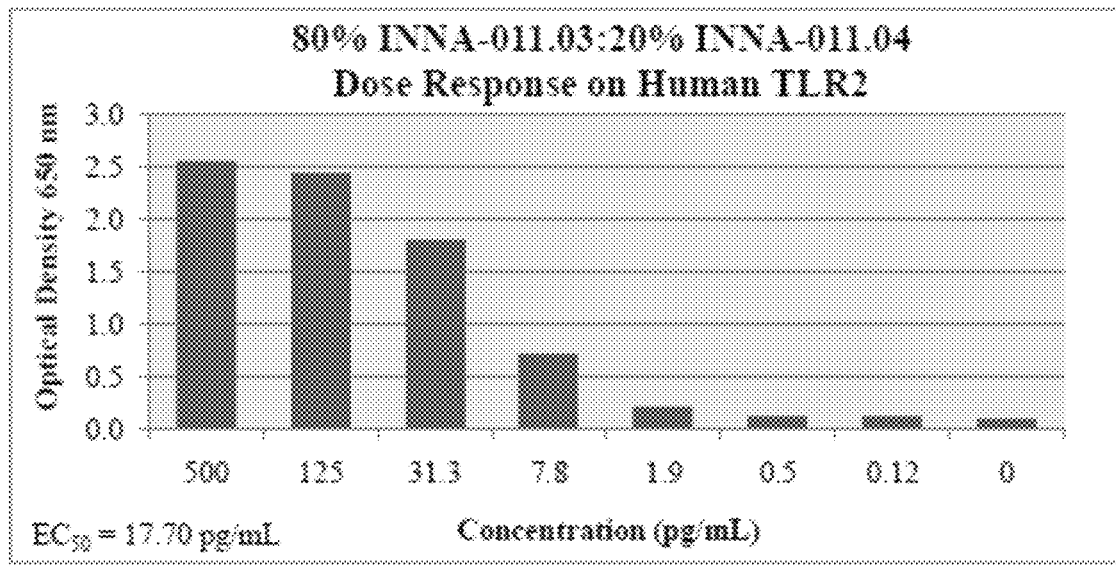

FIG. 16E: Human TLR2 Dose Response for 80% INNA-011.03 and 20% INNA-011.04.

Figure 17:
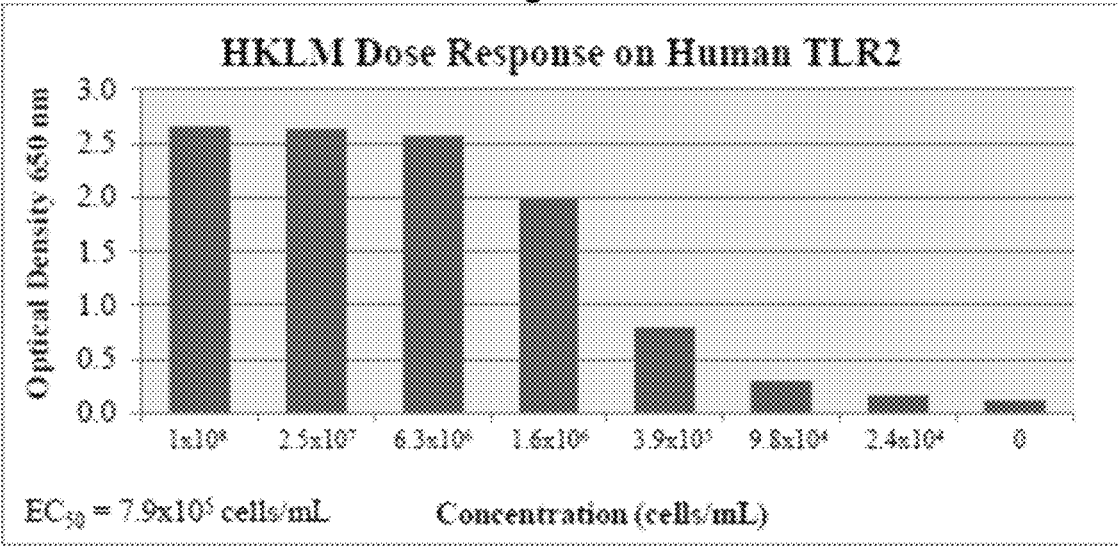

FIG. 17: Human TLR2 Dose Response for control ligand HKLM.

Figure 18:
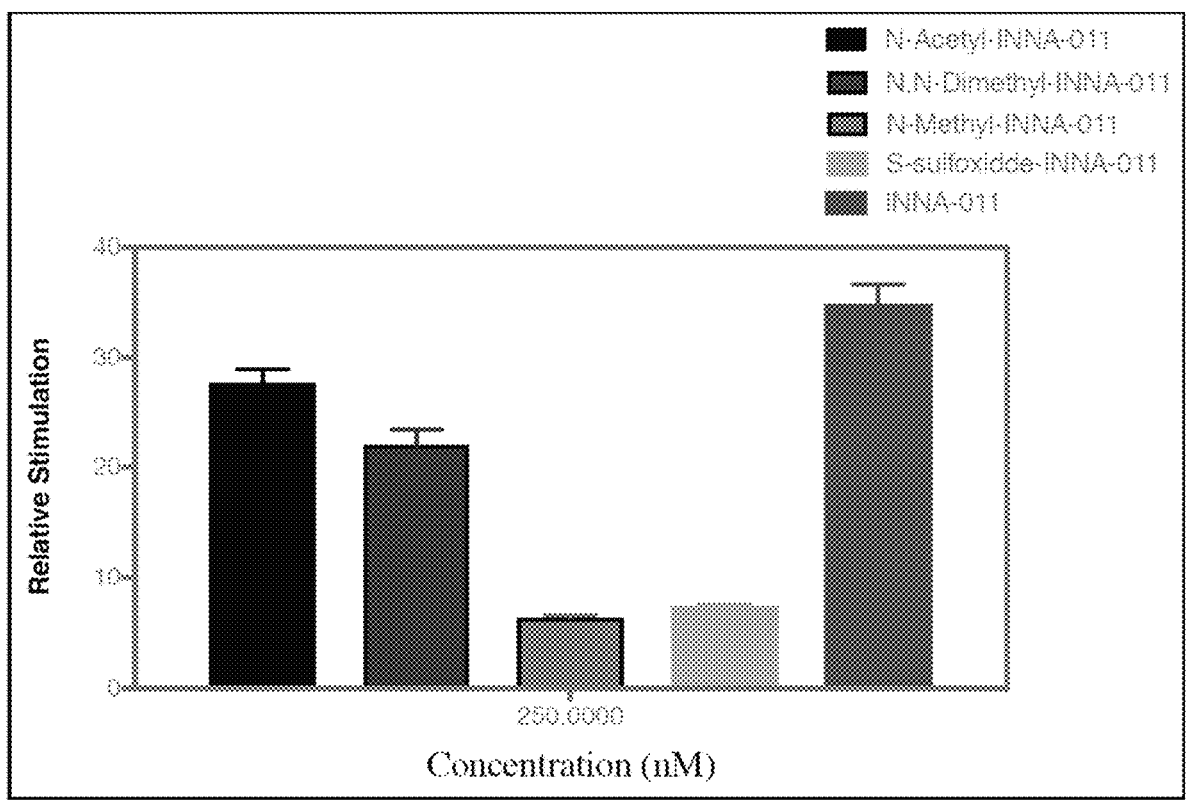

FIG. 18: Comparison of the abilities of N-acetyl-, N-methyl-, N,N-dimethyl and sulfoxide-INNA-011, and INNA-011 to stimulate luciferase activity in an NF-κB cell-based reporter system. The results from the five compounds listed in the legend from top to bottom are shown left to right on the horizontal axis.

Figure 19:
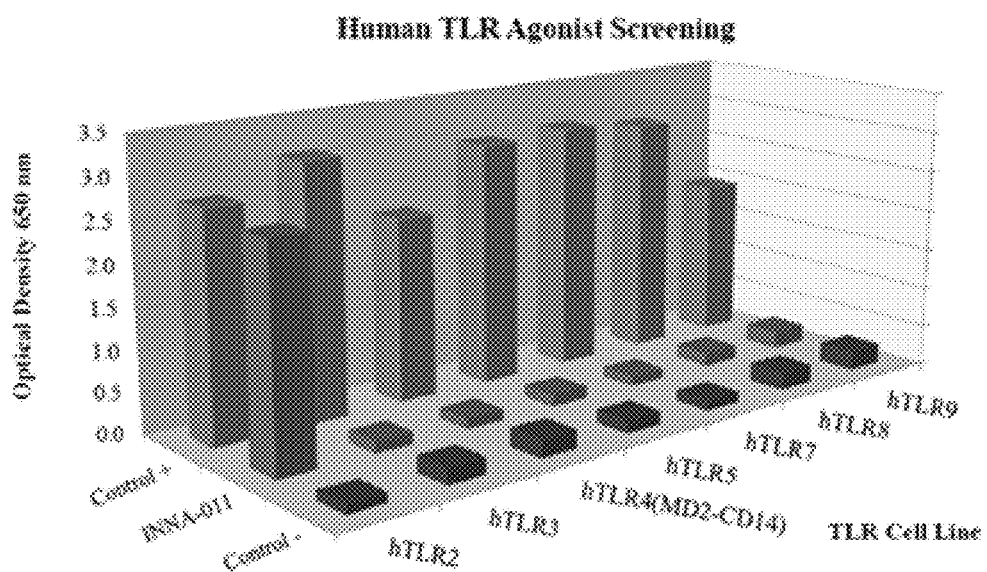

FIG. 19. Representative data indicating specific TLR-2 activation by INNA-011.

Figure 20:
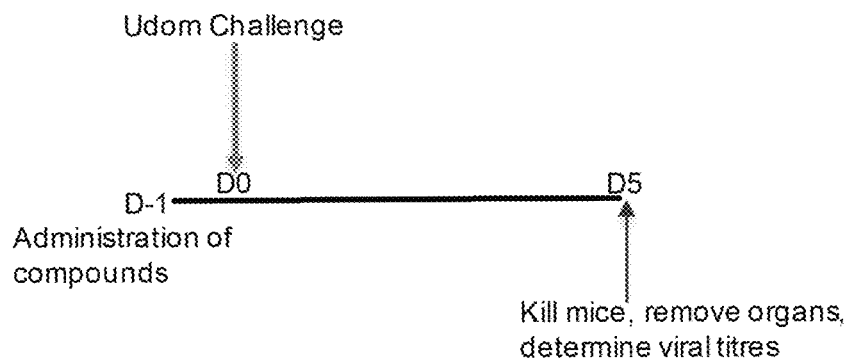

FIG. 20. Experimental design summary for URT challenge with Udorn virus.

Figure 21:
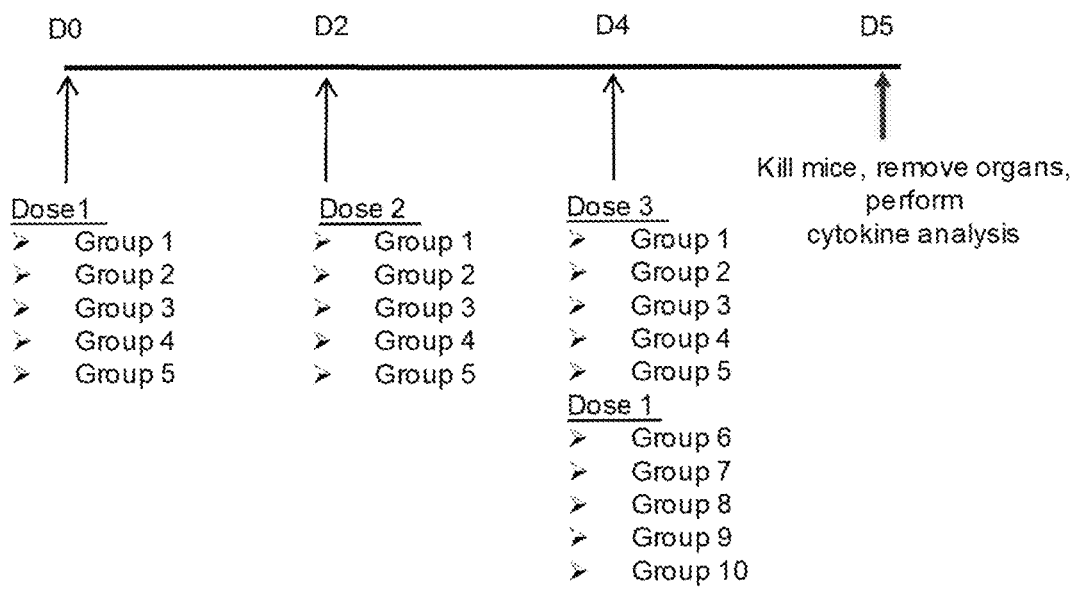

FIG. 21. Experimental design summary for assessing the effect of multiple doses of TLR2 agonists when administered to the URT.

Figure 22:
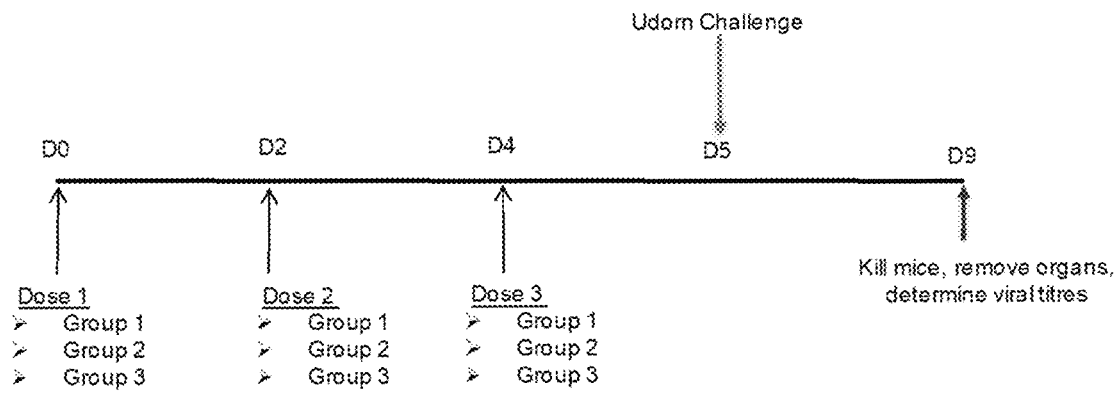

FIG. 22. Experimental design summary for assessing the effect of multiple doses of INNA-003 or INNA-006 followed by challenge with influenza virus on body weight and lung virus titres.

DETAILED DESCRIPTION OF THE EMBODIMENTS

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims. For instance, one skilled in the art will recognize that the modifications (—$NR_6R_7$, z, X, $R_9$ and $R_{10}$) made to the Pam2Cys moiety of the compounds of the present invention as described herein may be made independent of each other.

One skilled in the art will recognize many methods and materials similar or equivalent to those described herein, which could be used in the practice of the present invention.

The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

As discussed above, the inventors have developed and optimised novel compounds for the treatment and/or prevention of respiratory diseases or conditions, particularly those associated with an infectious agent, such as bacteria or virus. Specifically, the inventors have optimised compounds that provide significant protection against viral replication in the lung when those compounds are administered to the upper respiratory tract. These optimised compounds have significantly greater efficacy than other known TLR2 agonists. The surprising and unexpected efficacy also occurs without significantly compromising TLR specificity and/or causing significant weight loss in the animal models described herein.

In one aspect, the present invention provides a compound comprising the structure:

A-Y—B wherein A comprises or consists of:

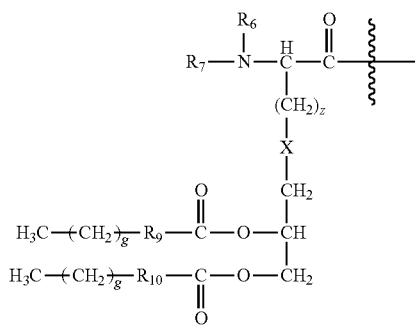

wherein each g is independently 10, 11, 12, 13, 14, 15, 16, 17 or 18;
z is 1 or 2;
X is S or S(=O);
$R_6$ and $R_7$ are independently selected from the group consisting of H, a straight or branched $C_1$-$C_4$ alkyl, and —C(=O)$CH_3$;
$R_9$ and $R_{10}$ are independently selected from the group consisting of —NH—, —O— or a single bond;
Y is

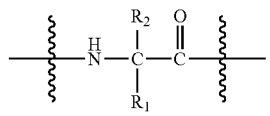

wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)$ $NH_2$, $-CH_2CH_2C(=O)OH$ and $-CH_2CH_2C(=O)OR_8$, wherein any one of the alkyl hydrogens can be replaced with a halogen;

$R_8$ is selected from the group consisting of H and a straight or branched $C_1$-$C_6$ alkyl;

and

B comprises or consists of Polyethylene Glycol (PEG), or a pharmaceutically acceptable salt or prodrug thereof.

The term "alkyl" refers to a saturated, straight-chain (i.e. linear) or branched hydrocarbon group. Specific examples of alkyl groups are methyl, ethyl, propyl, iso-propyl, n-butyl, iso-butyl, sec-butyl, tert-butyl, n-pentyl, iso-pentyl, n-hexyl and 2,2-dimethylbutyl. The alkyl group may be a $C_1$-$C_4$ or $C_1$-$C_6$ alkyl group. As used herein a wording defining the limits of a range of length such as, for example, "from 1 to 5" means any integer from 1 to 5, i.e. 1, 2, 3, 4 and 5. In other words, any range defined by two integers explicitly mentioned is meant to comprise and disclose any integer defining said limits and any integer comprised in said range. The alkyl group may be a branched alkyl group.

In one aspect, the present invention provides a compound comprising the structure:

A-Y—B wherein A comprises or consists of:

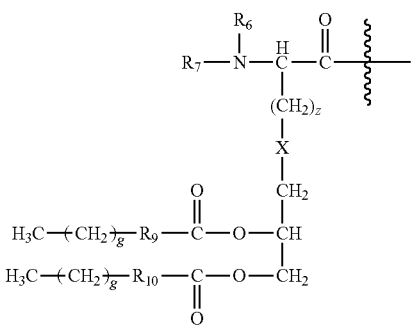

wherein each g is independently 10, 11, 12, 13, 14, 15, 16, 17 or 18;

z is 1 or 2;

X is S or S(=O);

$R_6$ and $R_7$ are independently selected from the group consisting of H, a straight or branched $C_1$-$C_4$ alkyl, and $-C(=O)CH_3$;

$R_9$ and $R_{10}$ are independently selected from the group consisting of $-NH-$, $-O-$ or a single bond;

Y is

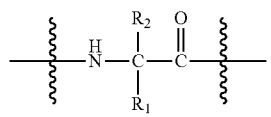

wherein $R_1$ and $R_2$ are independently selected from the group consisting of H, $-CH_2OH$, $-CH_2CH_2OH$, $-CH(CH_3)OH$ and $-CH_2OPO(OH)_2$, wherein any one of the alkyl hydrogens can be replaced with a halogen, and wherein $R_1$ and $R_2$ are not both H;

and

B comprises or consists of Polyethylene Glycol (PEG), or a pharmaceutically acceptable salt or prodrug thereof.

In one aspect, the present invention provides a compound comprising the structure:

A-Y—B wherein A comprises or consists of:

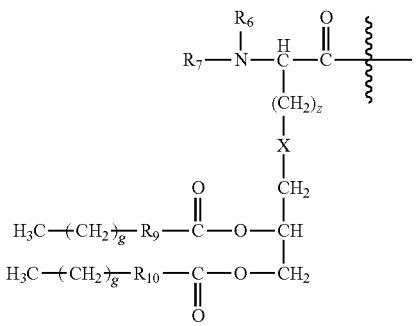

wherein each g is independently 10, 11, 12, 13, 14, 15, 16, 17 or 18;

z is 1;

X is S;

$R_6$ and $R_7$ are H;

$R_9$ and $R_{10}$ are both a single bond;

Y is

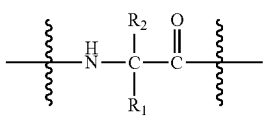

wherein $R_1$ and $R_2$ are independently selected from the group consisting of H, $-CH_2OH$, $-CH_2CH_2OH$, $-CH(CH_3)OH$, $-CH_2OPO(OH)_2$, $-CH_2C(=O)NH_2$, $-CH_2CH_2C(=O)OH$ and $-CH_2CH_2C(=O)OR_8$, wherein any one of the alkyl hydrogens can be replaced with a halogen;

$R_8$ is selected from the group consisting of H and a straight or branched $C_1$-$C_6$ alkyl; and B comprises or consists of Polyethylene Glycol (PEG), or a pharmaceutically acceptable salt or prodrug thereof.

In one aspect, the present invention provides a compound comprising the structure:

A-Y—B wherein A comprises or consists of:

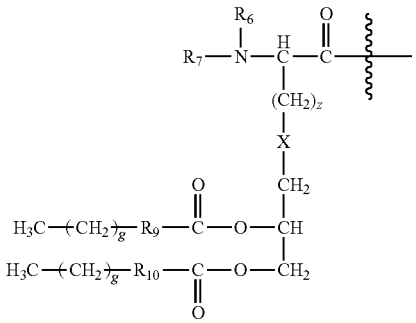

wherein each g is independently 10, 11, 12, 13, 14, 15, 16, 17 or 18;

z is 1;

X is S;

$R_6$ and $R_7$ are H;

$R_9$ and $R_{10}$ are both a single bond;

Y is

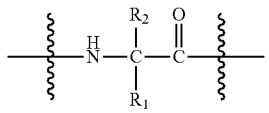

wherein $R_1$ and $R_2$ are independently selected from the group consisting of H, —CH$_2$OH, —CH$_2$CH$_2$OH, —CH(CH$_3$)OH and —CH$_2$OPO(OH)$_2$, wherein any one of the alkyl hydrogens can be replaced with a halogen, and wherein $R_1$ and $R_2$ are not both H;

and

B comprises or consists of Polyethylene Glycol (PEG), or a pharmaceutically acceptable salt or prodrug thereof.

In one aspect, the present invention provides a compound comprising the structure:

A-Y—B wherein A is:

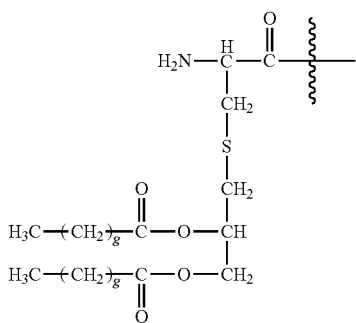

wherein each g is independently 10, 11, 12, 13, 14, 15, 16, 17 or 18;

Y is

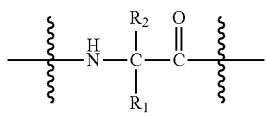

wherein $R_1$ and $R_2$ are independently selected from the group consisting of H, —CH$_2$OH, —CH$_2$CH$_2$OH, —CH(CH$_3$)OH and —CH$_2$OPO(OH)$_2$, wherein any one of the alkyl hydrogens can be replaced with a halogen, and wherein $R_1$ and $R_2$ are not both H;

and

B is Polyethylene Glycol (PEG), or a pharmaceutically acceptable salt or prodrug thereof.

The present invention also provides a compound comprising Pam2Cys and PEG, wherein the Pam2Cys and PEG are linked by a glycine, serine, homoserine, threonine, phosphoserine, asparagine or glutamine residue, or an ester of a glutamine residue, wherein Pam2Cys in the compound has the structure:

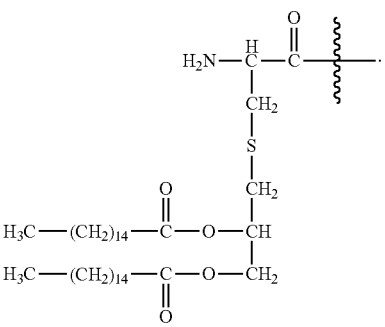

The term "ester" refers to a carboxylic acid group where the hydrogen of the hydroxyl group has been replaced by a saturated, straight-chain (i.e. linear) or branched hydrocarbon group. Specific examples of alkyl groups are methyl, ethyl, propyl, iso-propyl, n-butyl, iso-butyl, sec-butyl, tert-butyl, n-pentyl, iso-pentyl, n-hexyl and 2,2-dimethylbutyl. The alkyl group may be a $C_1$-$C_6$ alkyl group. As used herein a wording defining the limits of a range of length such as, for example, "from 1 to 5" means any integer from 1 to 5, i.e. 1, 2, 3, 4 and 5. In other words, any range defined by two integers explicitly mentioned is meant to comprise and disclose any integer defining said limits and any integer comprised in said range. The alkyl group may be a branched alkyl group.

The present invention also provides a compound comprising Pam2Cys and PEG, wherein the Pam2Cys and PEG are linked by a serine, homoserine, threonine or phosphoserine residue, wherein Pam2Cys in the compound has the structure:

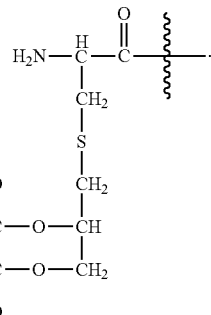

The present invention also provides a compound comprising Pam2Cys and PEG, wherein the Pam2Cys and PEG are linked by a serine residue, wherein
Pam2Cys-Ser has the structure:

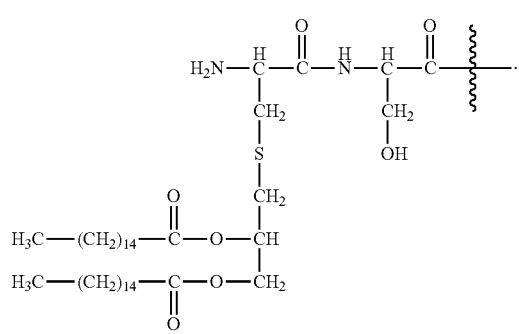

In one aspect, the present invention provides a compound comprising:

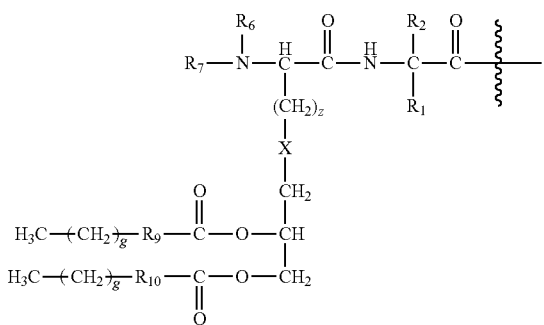

wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;

$R_6$ and $R_7$ are independently selected from the group consisting of H, a straight or branched $C_1$-$C_4$ alkyl, and —$C(=O)CH_3$;

$R_8$ is selected from the group consisting of H and a straight or branched $C_1$-$C_6$ alkyl;

$R_9$ and $R_{10}$ are independently selected from the group consisting of —NH—, —O— or a single bond;

z is 1 or 2; and

X is S or S(=O);

covalently linked to polyethylene glycol (PEG), or a pharmaceutically acceptable salt or prodrug thereof.

In one aspect, the present invention provides a compound comprising:

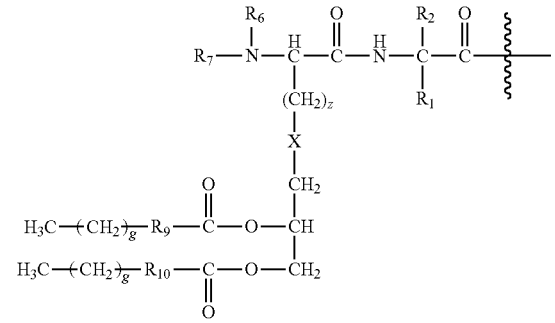

wherein $R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;

$R_6$ and $R_7$ are independently selected from the group consisting of H, a straight or branched $C_1$-$C_4$ alkyl, and —$C(=O)CH_3$;

$R_9$ and $R_{10}$ are independently selected from the group consisting of —NH—, —O— or a single bond;

z is 1 or 2; and

X is S or S(=O);

covalently linked to polyethylene glycol (PEG), or a pharmaceutically acceptable salt or prodrug thereof.

In one aspect, the present invention provides a compound comprising:

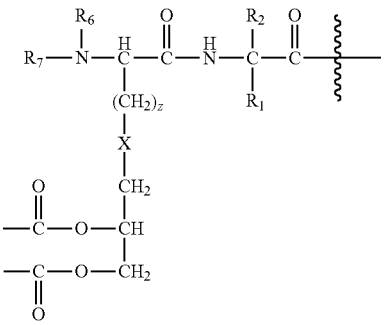

wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;

$R_6$ and $R_7$ are H;

$R_9$ and $R_{10}$ are both a single bond;

$R_8$ is selected from the group consisting of H and a straight or branched $C_1$-$C_6$ alkyl;

z is 1; and

X is S;

covalently linked to polyethylene glycol (PEG), or a pharmaceutically acceptable salt or prodrug thereof.

In one aspect, the present invention provides a compound comprising:

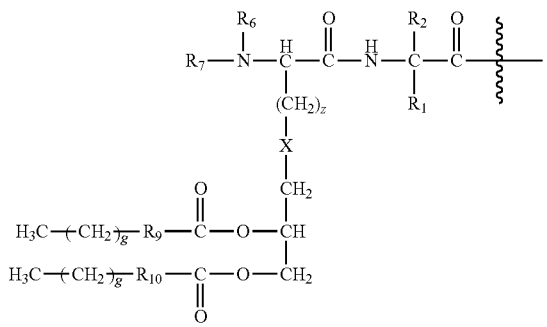

wherein $R_1$ and $R_2$ are independently selected from the group consisting of H, —CH$_2$OH, —CH$_2$CH$_2$OH, —CH(CH$_3$)OH and —CH$_2$OPO(OH)$_2$, wherein any one of the alkyl hydrogens can be replaced with a halogen, and wherein $R_1$ and $R_2$ are not both H;
$R_6$ and $R_7$ are H;
$R_9$ and $R_{10}$ are both a single bond;
z is 1; and
X is S;
covalently linked to polyethylene glycol (PEG), or a pharmaceutically acceptable salt or prodrug thereof.

In one aspect, the present invention provides a compound comprising:

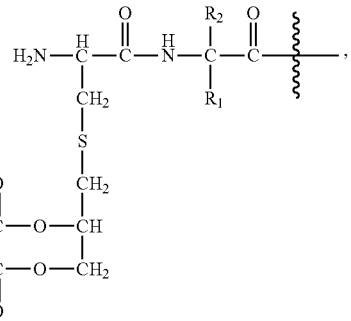

wherein $R_1$ and $R_2$ are independently selected from the group consisting of H, —CH$_2$OH, —CH$_2$CH$_2$OH, —CH(CH$_3$)OH and —CH$_2$OPO(OH)$_2$, wherein any one of the alkyl hydrogens can be replaced with a halogen, and wherein $R_1$ and $R_2$ are not both H;
covalently linked to polyethylene glycol (PEG), or a pharmaceutically acceptable salt or prodrug thereof.

In one aspect, the present invention provides a compound of formula (VI):

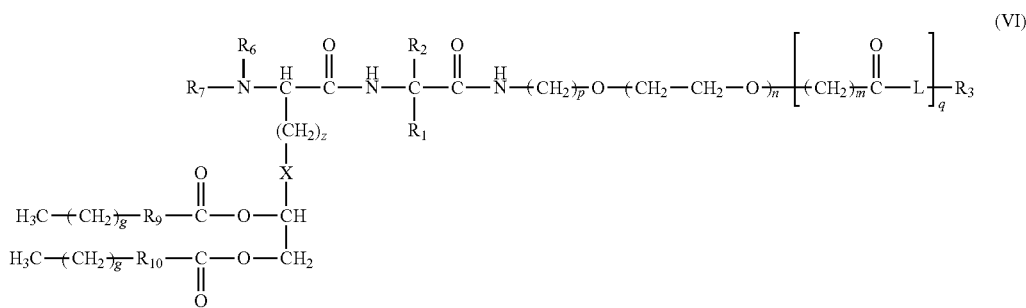

wherein n is 3 to 100;

m is 1, 2, 3 or 4;

each g is independently 10, 11, 12, 13, 14, 15, 16, 17 or 18;

p is 2, 3 or 4;

q is null or 1;

$R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;

$R_6$ and $R_7$ are independently selected from the group consisting of H, a straight or branched $C_1$-$C_4$ alkyl, and —$C(=O)CH_3$;

$R_8$ is selected from the group consisting of H and a straight or branched $C_1$-$C_6$ alkyl;

$R_9$ and $R_{10}$ are independently selected from the group consisting of —NH—, —O— or a single bond;

z is 1 or 2;

X is S or S(=O);

wherein when q=1, $R_3$ is —$NH_2$ or —OH;

wherein when q=0, $R_3$ is H;

L is null or consists of 1 to 10 units, wherein each unit is a natural alpha amino acid or derived from a natural alpha amino acid, and has the formula:

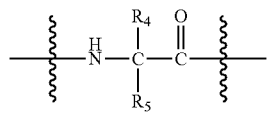

wherein $R_4$ is H; and $R_5$ is the side chain, or second hydrogen of the amino acid or a pharmaceutically acceptable salt or prodrug thereof.

In one aspect, the present invention provides a compound of formula (VI):

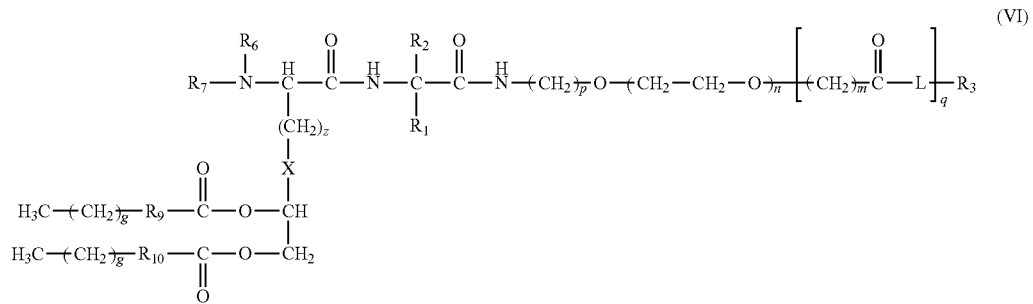

wherein n is 3 to 100;

m is 1, 2, 3 or 4;

each g is independently 10, 11, 12, 13, 14, 15, 16, 17 or 18;

p is 2, 3 or 4;

q is null or 1;

$R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;

$R_6$ and $R_7$ are independently selected from the group consisting of H, a straight or branched $C_1$-$C_4$ alkyl, and —$C(=O)CH_3$;

$R_9$ and $R_{10}$ are independently selected from the group consisting of —NH—, —O— or a single bond;

z is 1 or 2;

X is S or S(=O);

wherein when q=1, $R_3$ is —$NH_2$ or —OH;

wherein when q=0, $R_3$ is H;

L is null or consists of 1 to 10 units, wherein each unit is a natural alpha amino acid or derived from a natural alpha amino acid, and has the formula:

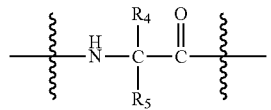

wherein $R_4$ is H; and $R_5$ is the side chain, or second hydrogen of the amino acid or a pharmaceutically acceptable salt or prodrug thereof.

In one aspect, the present invention provides a compound of formula (VI):

wherein n is 3 to 100;

m is 1, 2, 3 or 4;

each g is independently 10, 11, 12, 13, 14, 15, 16, 17 or 18;

p is 2, 3 or 4;

q is null or 1;

$R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;

$R_6$ and $R_7$ are H;

$R_9$ and $R_{10}$ are both a single bond;

$R_8$ is selected from the group consisting of H and a straight or branched $C_1$-$C_6$ alkyl;

z is 1;

X is S;

wherein when q=1, $R_3$ is —$NH_2$ or —OH;

wherein when q=0, $R_3$ is H;

L is null or consists of 1 to 10 units, wherein each unit is a natural alpha amino acid or derived from a natural alpha amino acid, and has the formula:

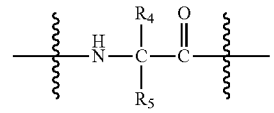

wherein $R_4$ is H; and $R_5$ is the side chain, or second hydrogen of the amino acid or a pharmaceutically acceptable salt or prodrug thereof.

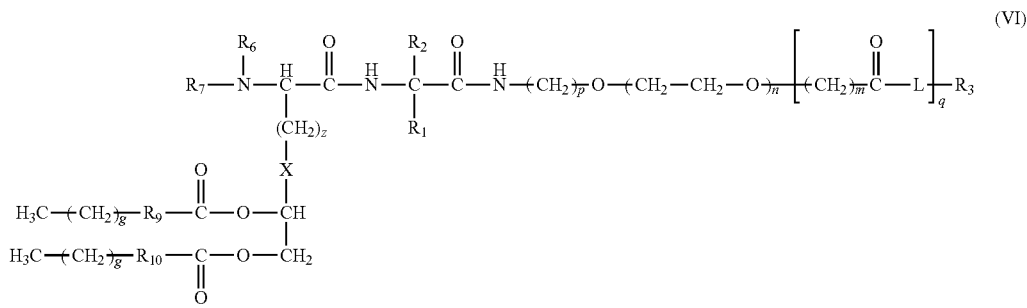

In one aspect, the present invention provides a compound of formula (VI):

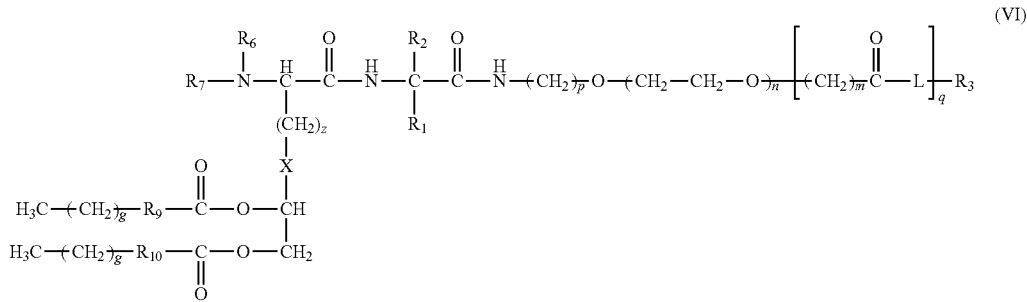

wherein
n is 3 to 100;
m is 1, 2, 3 or 4;
each g is independently 10, 11, 12, 13, 14, 15, 16, 17 or 18;
p is 2, 3 or 4;
q is null or 1;
$R_1$ and $R_2$ are independently selected from the group consisting of H, —$CH_2OH$, —$CH_2CH_2OH$, —CH($CH_3$)OH and —$CH_2OPO(OH)_2$, wherein any one of the alkyl hydrogens can be replaced with a halogen, and wherein $R_1$ and $R_2$ are not both H;
$R_6$ and $R_7$ are H;
$R_9$ and $R_{10}$ are both a single bond;
z is 1;
X is S;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

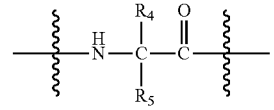

wherein $R_4$ is H; and
$R_5$ is the side chain, or second hydrogen of the amino acid or a pharmaceutically acceptable salt or prodrug thereof.

In one aspect, the present invention provides a compound of formula (I):

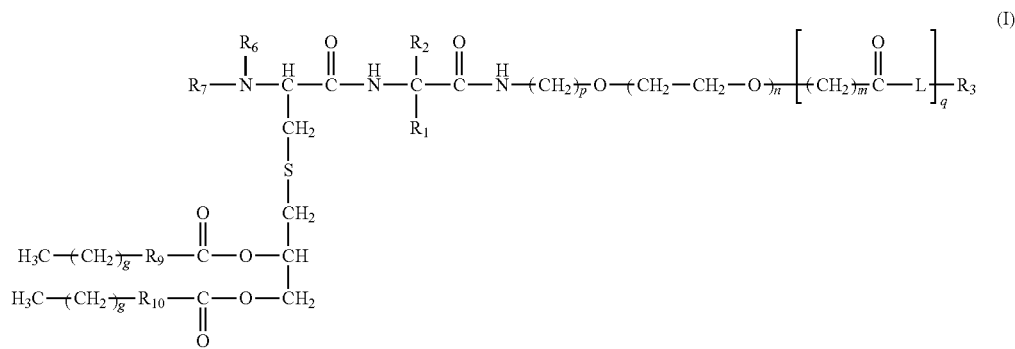

wherein
n is 3 to 100;
m is 1, 2, 3 or 4;
each g is independently 10, 11, 12, 13, 14, 15, 16, 17 or 18;
p is 2, 3 or 4;
q is null or 1;
$R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

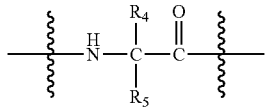

wherein $R_4$ is H; and
$R_5$ is the side chain, or second hydrogen of the amino acid or a pharmaceutically acceptable salt or prodrug thereof.
In one embodiment, the present invention provides a compound of formula (VII):

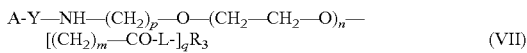  (VII)

wherein
A has the structure:

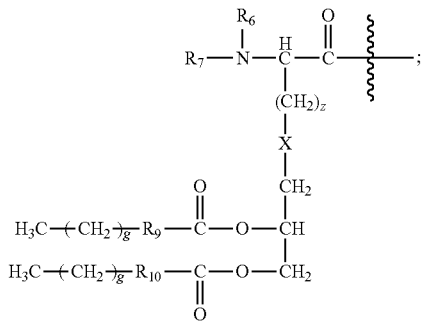

Y is

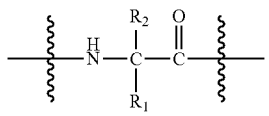

wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;
$R_6$ and $R_7$ are independently selected from the group consisting of H, a straight or branched $C_1$-$C_4$ alkyl, and —$C(=O)CH_3$;

$R_8$ is selected from the group consisting of H and a straight or branched $C_1$-$C_6$ alkyl;
$R_9$ and $R_{10}$ are independently selected from the group consisting of —NH—, —O— or a single bond;
z is 1 or 2;
X is S or S(=O);
n is 3 to 100;
m is 1, 2, 3 or 4;
each g is independently 10, 11, 12, 13, 14, 15, 16, 17 or 18;
p is 2, 3 or 4;
q is null or 1;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

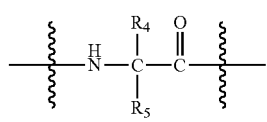

wherein $R_4$ is H; and
$R_5$ is the side chain, or second hydrogen of the amino acid, or a pharmaceutically acceptable salt or prodrug thereof.
In one embodiment, the present invention provides a compound of formula (VII):

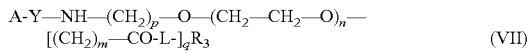  (VII)

wherein
A has the structure:

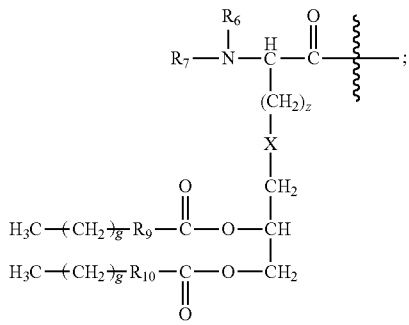

Y is

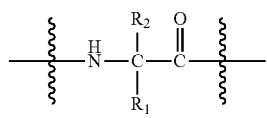

wherein $R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;
$R_6$ and $R_7$ are independently selected from the group consisting of H, a straight or branched $C_1$-$C_4$ alkyl, and —$C(=O)CH_3$;

$R_9$ and $R_{10}$ are independently selected from the group consisting of —NH—, —O— or a single bond;
z is 1 or 2;
X is S or S(=O);
n is 3 to 100;
m is 1, 2, 3 or 4;
each g is independently 10, 11, 12, 13, 14, 15, 16, 17 or 18;
p is 2, 3 or 4;
q is null or 1;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

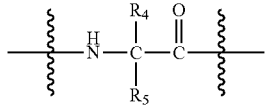

wherein $R_4$ is H; and
$R_5$ is the side chain, or second hydrogen of the amino acid, or a pharmaceutically acceptable salt or prodrug thereof.

In one embodiment, the present invention provides a compound of formula (VII):

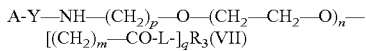

wherein
A has the structure:

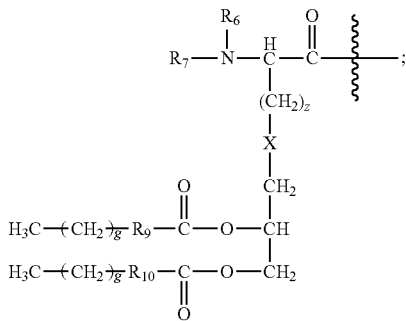

Y is

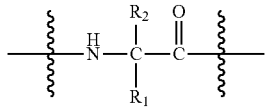

wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;
$R_6$ and $R_7$ are H;
$R_9$ and $R_{10}$ are both a single bond;
$R_8$ is selected from the group consisting of H and a straight or branched $C_1$-$C_6$ alkyl;

z is 1;
X is S;
n is 3 to 100;
m is 1, 2, 3 or 4;
each g is independently 10, 11, 12, 13, 14, 15, 16, 17 or 18;
p is 2, 3 or 4;
q is null or 1;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

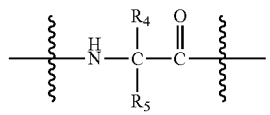

wherein $R_4$ is H; and
$R_5$ is the side chain, or second hydrogen of the amino acid, or a pharmaceutically acceptable salt or prodrug thereof.

In one embodiment, the present invention provides a compound of formula (VII):

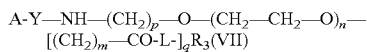

wherein
A has the structure:

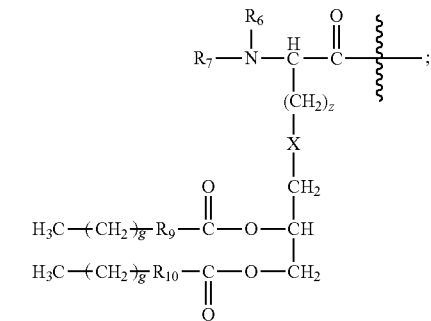

Y is

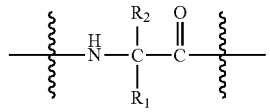

wherein $R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;
$R_6$ and $R_7$ are H;
$R_9$ and $R_{10}$ are both a single bond;
z is 1;
X is S;
n is 3 to 100;
m is 1, 2, 3 or 4;
each g is independently 10, 11, 12, 13, 14, 15, 16, 17 or 18;

p is 2, 3 or 4;

q is null or 1;

wherein when q=1, $R_3$ is —$NH_2$ or —OH;

wherein when q=0, $R_3$ is H;

L is null or consists of 1 to 10 units, wherein each unit is a natural alpha amino acid or derived from a natural alpha amino acid, and has the formula:

$$\text{—NH—C(R}_4\text{)(R}_5\text{)—C(=O)—}$$

wherein $R_4$ is H; and $R_5$ is the side chain, or second hydrogen of the amino acid, or a pharmaceutically acceptable salt or prodrug thereof.

In one embodiment, the compound has the formula (II):

$$\text{A-Y—NH—(CH}_2\text{)}_p\text{—O—(CH}_2\text{—CH}_2\text{—O)}_n\text{—[(CH}_2\text{)}_m\text{—CO-L-]}_q R_3 \quad \text{(II)}$$

wherein

A has the structure:

$$H_2N-\underset{\underset{\underset{\underset{O}{\overset{\|}{C}}}{\overset{|}{CH_2}}}{\overset{|}{S}}}{\overset{H}{C}}-\overset{O}{\overset{\|}{C}}-$$

with $H_3C$—$(CH_2)_g$—$C(=O)$—$O$—$CH$ and $H_3C$—$(CH_2)_g$—$C(=O)$—$O$—$CH_2$ Y is $$\text{—NH—C(R}_1\text{)(R}_2\text{)—C(=O)—}$$

wherein $R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;

n is 3 to 100;

m is 1, 2, 3 or 4;

each g is independently 10, 11, 12, 13, 14, 15, 16, 17 or 18;

p is 2, 3 or 4;

q is null or 1;

wherein when q=1, $R_3$ is —$NH_2$ or —OH;

wherein when q=0, $R_3$ is H;

L is null or consists of 1 to 10 units, wherein each unit is a natural alpha amino acid or derived from a natural alpha amino acid, and has the formula:

$$\text{—NH—C(R}_4\text{)(R}_5\text{)—C(=O)—}$$

wherein $R_4$ is H; and $R_5$ is the side chain, or second hydrogen of the amino acid or a pharmaceutically acceptable salt or prodrug thereof.

In one embodiment, the compound has the formula (VIII):

$$\text{Pam2Cys-Y—NH—(CH}_2\text{)}_p\text{—O—(CH}_2\text{—CH}_2\text{—O)}_n\text{—[(CH}_2\text{)}_m\text{—CO-L-]}_q R_3 \quad \text{(VIII)}$$

wherein

Pam2Cys has the structure:

$$H_2N-\overset{H}{\underset{\underset{\underset{\underset{O}{\overset{\|}{C}}}{\overset{|}{CH_2}}}{\overset{|}{S}}}{C}}-\overset{O}{\overset{\|}{C}}-$$

with $H_3C$—$(CH_2)_{14}$—$C(=O)$—$O$—$CH$ and $H_3C$—$(CH_2)_{14}$—$C(=O)$—$O$—$CH_2$ Y is:

$$\text{—NH—C(R}_1\text{)(R}_2\text{)—C(=O)—}$$

wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;

$R_8$ is selected from the group consisting of H and a straight or branched $C_1$-$C_6$ alkyl;

n is 3 to 100;

m is 1, 2, 3 or 4;

p is 2, 3 or 4;

q is null or 1;

wherein when q=1, $R_3$ is H, —$NH_2$ or —OH;

wherein when q=0, $R_3$ is H;

L is null or consists of 1 to 10 units, wherein each unit is a natural alpha amino acid or derived from a natural alpha amino acid, and has the formula:

$$\text{—NH—C(R}_4\text{)(R}_5\text{)—C(=O)—}$$

wherein $R_4$ is H; and $R_5$ is the side chain, or second hydrogen of the amino acid, or a pharmaceutically acceptable salt or prodrug thereof.

In one embodiment, the compound has the formula (VIII):

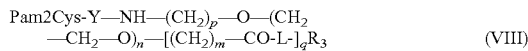
(VIII)

wherein

Pam2Cys has the structure:

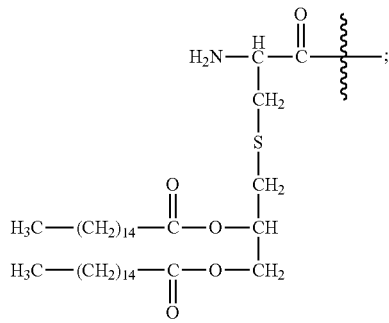

Y is:

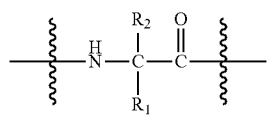

wherein $R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;

n is 3 to 100;

m is 1, 2, 3 or 4;

p is 2, 3 or 4;

q is null or 1;

wherein when q=1, $R_3$ is H, —$NH_2$ or —OH;

wherein when q=0, $R_3$ is H;

L is null or consists of 1 to 10 units, wherein each unit is a natural alpha amino acid or derived from a natural alpha amino acid, and has the formula:

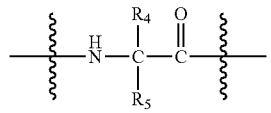

wherein $R_4$ is H; and $R_5$ is the side chain, or second hydrogen of the amino acid, or a pharmaceutically acceptable salt or prodrug thereof.

In one embodiment, the present invention provides a compound of formula (III):

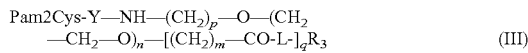
(III)

wherein

Pam2Cys has the structure:

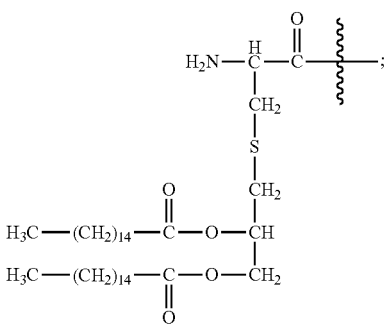

Y is

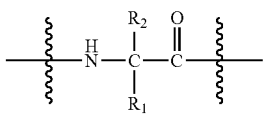

wherein $R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;

n is 3 to 100;

m is 1, 2, 3 or 4;

p is 2, 3 or 4;

q is null or 1;

wherein when q=1, $R_3$ is —$NH_2$ or —OH;

wherein when q=0, $R_3$ is H;

L is null or consists of 1 to 10 units, wherein each unit is a natural alpha amino acid or derived from a natural alpha amino acid, and has the formula:

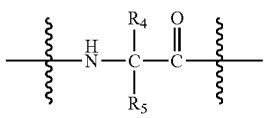

wherein $R_4$ is H; and $R_5$ is the side chain, or second hydrogen of the amino acid, or a pharmaceutically acceptable salt or prodrug thereof.

In one embodiment, the present invention provides a compound of formula (IV):

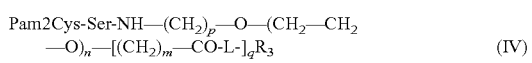
(IV)

wherein
Pam2Cys-Ser has the structure:

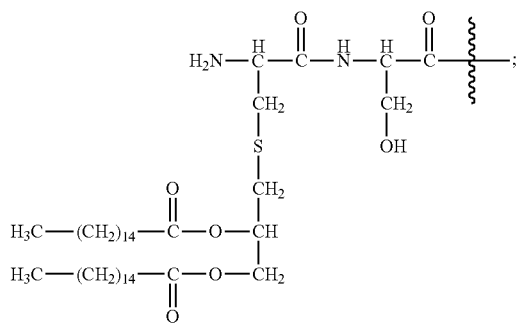

n is 3 to 100;
m is 1, 2, 3 or 4;
p is 2, 3 or 4;
q is null or 1;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

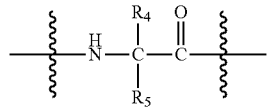

wherein $R_4$ is H; and
$R_5$ is the side chain, or second hydrogen of the amino acid or a pharmaceutically acceptable salt or prodrug thereof.
In one embodiment, the compound has the formula (X):

wherein
n is 3 to 100;
k is 3 to 100;
m is 1, 2, 3 or 4;
each g is independently 10, 11, 12, 13, 14, 15, 16, 17 or 18;
p is 2, 3 or 4;
t is 2, 3 or 4;
h is 1, 2, 3 or 4;
q is null or 1;
wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;
$R_6$ and $R_7$ are independently selected from the group consisting of H, a straight or branched $C_1$-$C_4$ alkyl, and —$C(=O)CH_3$;
$R_8$ is selected from the group consisting of H and a straight or branched $C_1$-$C_6$ alkyl;
$R_9$ and $R_{10}$ are independently selected from the group consisting of —NH—, —O— or a single bond;
z is 1 or 2;
X is S or S(=O);
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

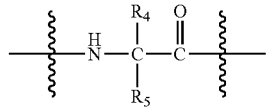

wherein $R_4$ is H; and
$R_5$ is the side chain, or second hydrogen of the amino acid, or a pharmaceutically acceptable salt or prodrug thereof.

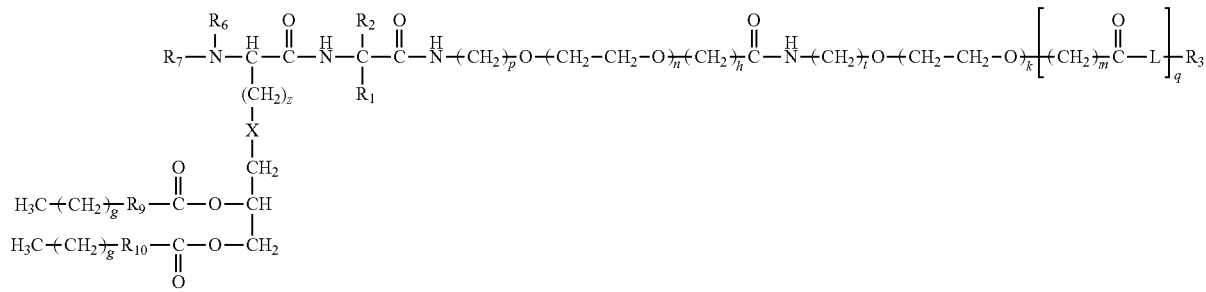

In one embodiment, the compound has the formula (X):

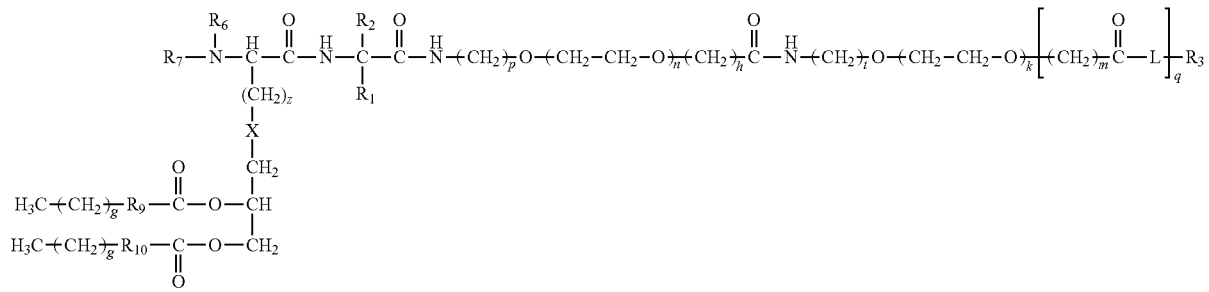

wherein
n is 3 to 100;
k is 3 to 100;
m is 1, 2, 3 or 4;
each g is independently 10, 11, 12, 13, 14, 15, 16, 17 or 18;
p is 2, 3 or 4;
t is 2, 3 or 4;
h is 1, 2, 3 or 4;
q is null or 1;
wherein $R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;
$R_6$ and $R_7$ are independently selected from the group consisting of H, a straight or branched $C_1$-$C_4$ alkyl, and —C(=O)$CH_3$;
$R_9$ and $R_{10}$ are independently selected from the group consisting of —NH—, —O— or a single bond;
z is 1 or 2;
X is S or S(=O);
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

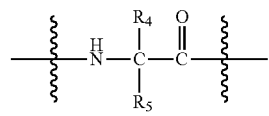

wherein $R_4$ is H; and
$R_5$ is the side chain, or second hydrogen of the amino acid, or a pharmaceutically acceptable salt or prodrug thereof.
In one embodiment, the compound has the formula (X):

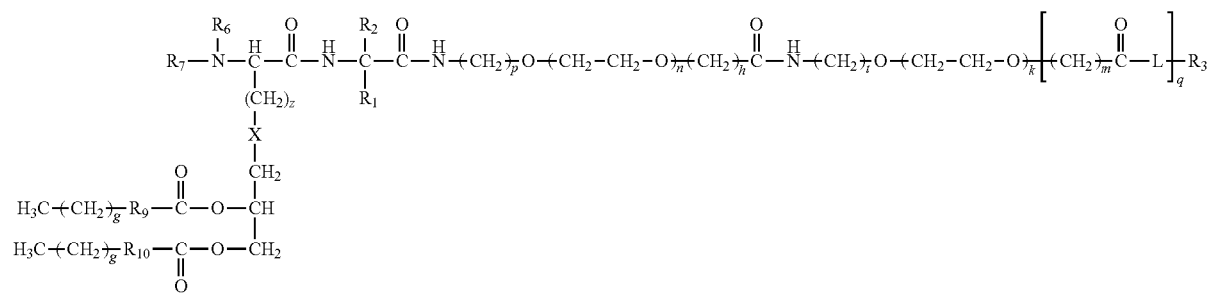

wherein
n is 3 to 100;
k is 3 to 100;
m is 1, 2, 3 or 4;
each g is independently 10, 11, 12, 13, 14, 15, 16, 17 or 18;
p is 2, 3 or 4;
t is 2, 3 or 4;
his 1, 2, 3 or 4;
q is null or 1;
wherein $R_1$ and $R_2$ are independently selected from the group consisting of H, —$CH_2OH$, —$CH_2CH_2OH$, —$CH(CH_3)OH$, —$CH_2OPO(OH)_2$, —$CH_2C(=O)NH_2$, —$CH_2CH_2C(=O)OH$ and —$CH_2CH_2C(=O)OR_8$, wherein any one of the alkyl hydrogens can be replaced with a halogen;
$R_6$ and $R_7$ are H;
$R_9$ and $R_{10}$ are both a single bond;
$R_8$ is selected from the group consisting of H and a straight or branched $C_1$-$C_6$ alkyl;
z is 1;
X is S;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

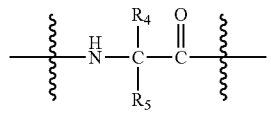

wherein $R_4$ is H; and
$R_5$ is the side chain, or second hydrogen of the amino acid, or a pharmaceutically acceptable salt or prodrug thereof.
In one embodiment, the compound has the formula (X):

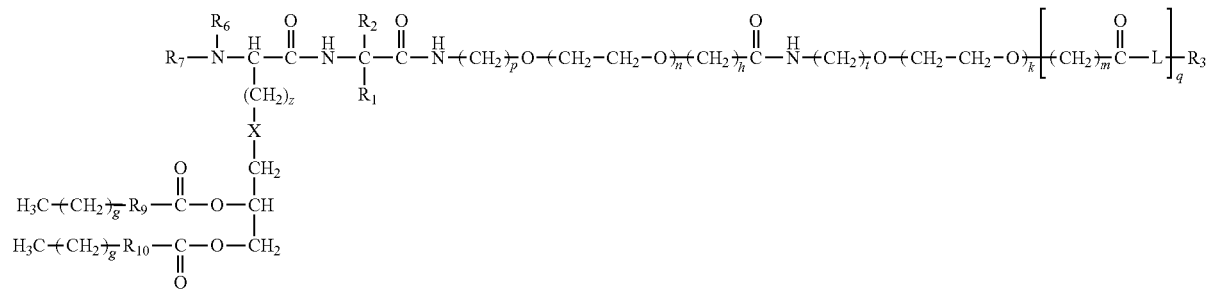

wherein n is 3 to 100;
k is 3 to 100;
m is 1, 2, 3 or 4;
each g is independently 10, 11, 12, 13, 14, 15, 16, 17 or 18;
p is 2, 3 or 4;
t is 2, 3 or 4;
h is 1, 2, 3 or 4;
q is null or 1;
wherein $R_1$ and $R_2$ are independently selected from the group consisting of H, —CH$_2$OH, —CH$_2$CH$_2$OH, —CH(CH$_3$)OH and —CH$_2$OPO(OH)$_2$, wherein any one of the alkyl hydrogens can be replaced with a halogen, and wherein $R_1$ and $R_2$ are not both H;
$R_6$ and $R_7$ are H;
$R_9$ and $R_{10}$ are both a single bond;
z is 1;
X is S;
wherein when q=1, $R_3$ is —NH$_2$ or —OH;
wherein when q=0, $R_3$ is H;
L is null or consists of 1 to 10 units, wherein each unit is a natural alpha amino acid or derived from a natural alpha amino acid, and has the formula:

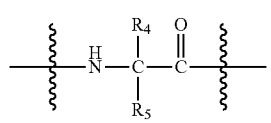

wherein $R_4$ is H; and
$R_5$ is the side chain, or second hydrogen of the amino acid, or a pharmaceutically acceptable salt or prodrug thereof.
In one embodiment, the compound has the formula (V):

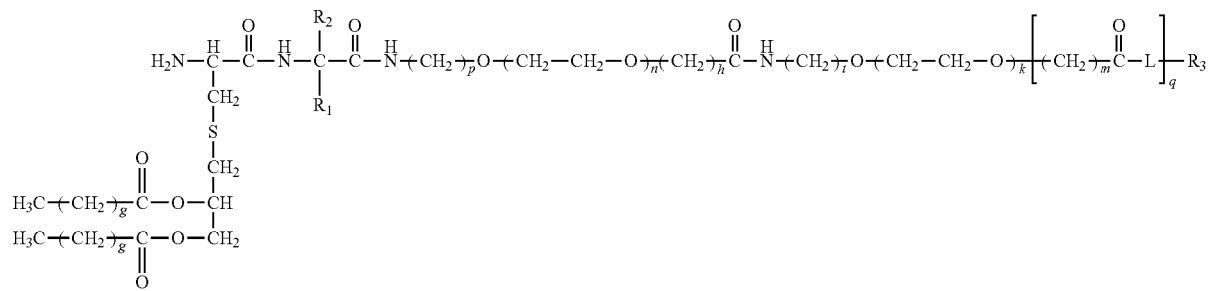

wherein
n is 3 to 100;
k is 3 to 100;
m is 1, 2, 3 or 4;
each g is independently 10, 11, 12, 13, 14, 15, 16, 17 or 18;
p is 2, 3 or 4;
t is 2, 3 or 4;
h is 1, 2, 3 or 4;
q is null or 1;
$R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

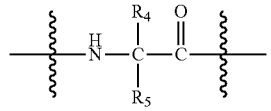

wherein $R_4$ is H; and
$R_5$ is the side chain, or second hydrogen of the amino acid,
or a pharmaceutically acceptable salt or prodrug thereof.

For all the above structures, where present, one or more of the following features are preferable:

n is between 10-14, even more preferably, n is 11.
n is 3 or 5.
n is between 24-30, even more preferably, n is 27.
k is between 24-30, even more preferably, k is 27.
m is 1-3, even more preferably, m is 2.
h is 1-3, even more preferably, h is 2.
g is between 10-16, even more preferably, g is between 12-14, most preferably, g is 14.
one of $R_1$ and $R_2$ is hydrogen.
p is 2.
t is 2.
z is 1.
X is S.
$R_6$ and $R_7$ are H.
$R_9$ and $R_{10}$ are both a single bond.

In one preferred embodiment of the invention, the compound has the structure of compound (1):

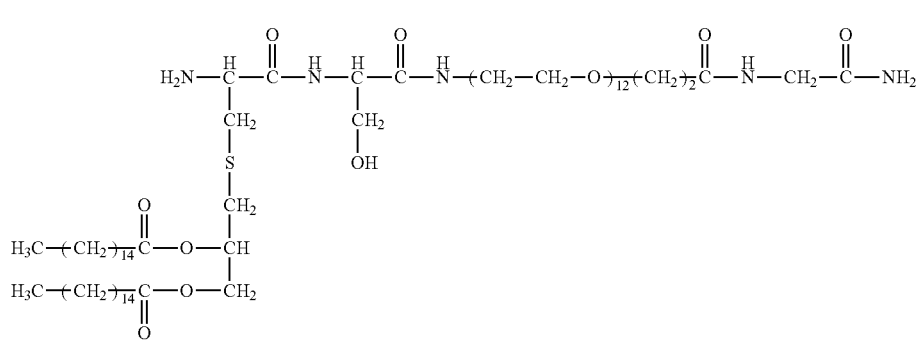

(1)

or a pharmaceutically acceptable salt or prodrug thereof.
This compound may also be referred to as Pam2Cys-Ser-PEG, or INNA-006.

In other preferred embodiments, the compound is selected from the group consisting of:

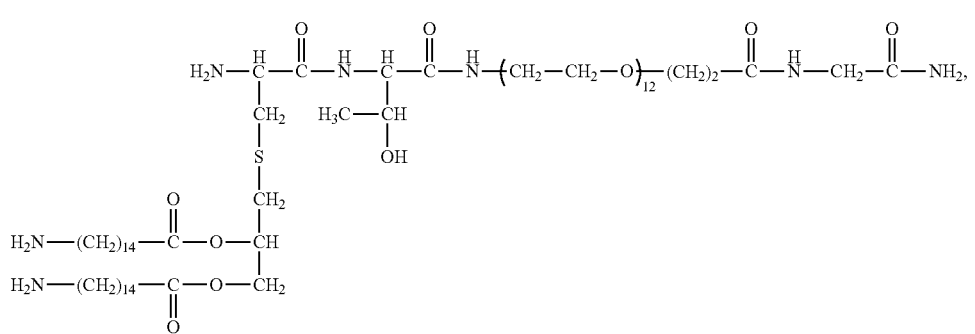

(2)

-continued
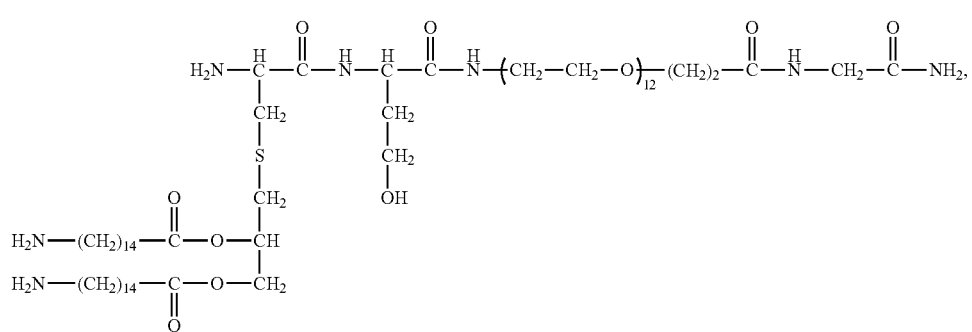
(3)
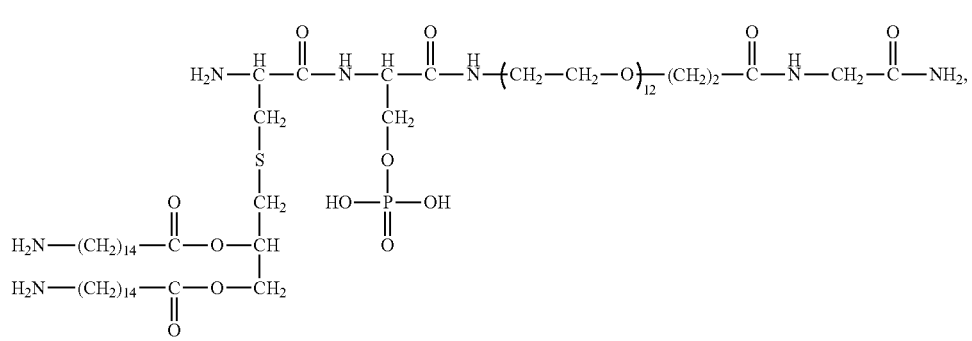
(4)
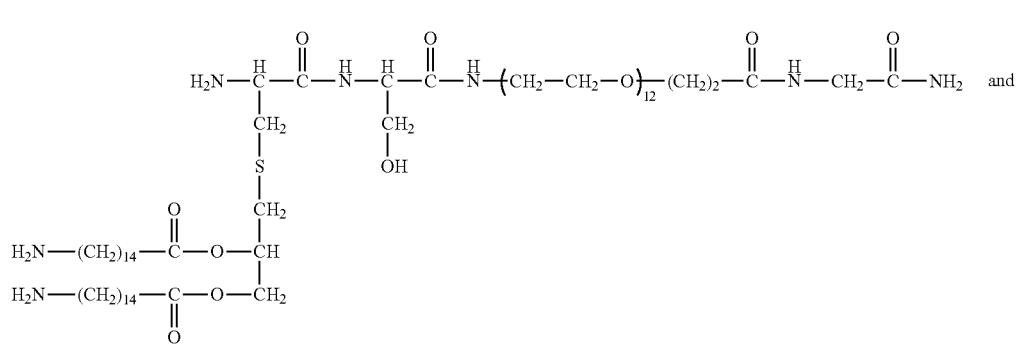
(5) and
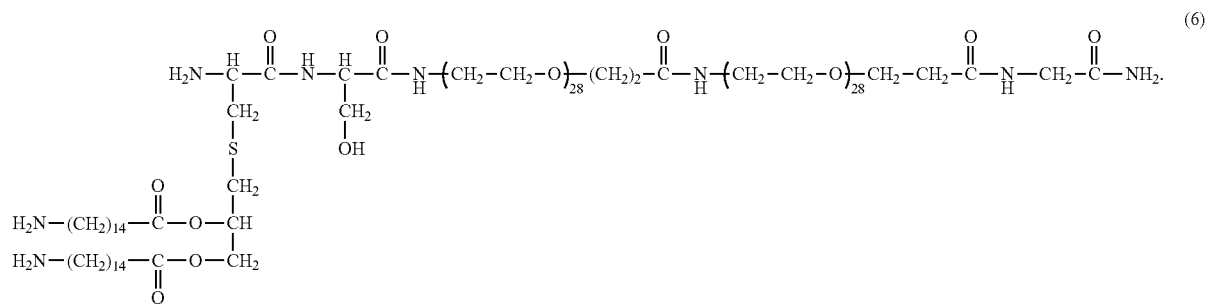
(6)

In one particularly preferred embodiment, the compound is:

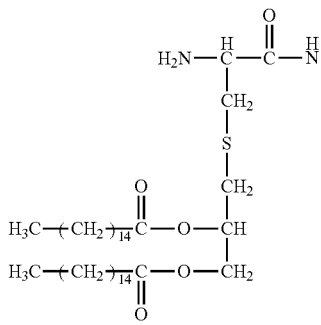

(5)

The present invention also provides for compositions containing a compound of formula (I), formula (II), formula (III), formula (IV), formula (V), formula (VI), formula (VII), formula (VIII) and/or formula (X) or a pharmaceutically acceptable salt or prodrug thereof, and a pharmaceutically acceptable carrier, diluent or excipient.

As discussed above, the present invention provides Toll-Like Receptor 2 protein (TLR2) agonist compounds and their compositions. In humans, TLR2 plays a fundamental role in the recognition of pathogens and activation of the innate immunity response. It is encoded by the TLR2 gene and is expressed on the surface of specific cells.

Without wishing to be bound by any theory or mode of action, it is believed that the compounds of the invention described herein are agonists of TLR2 and show activity by binding at TLR2 and stimulating the innate immune system. The innate immune system forms an immediate defence against pathogens such as pathogens that infect and replicate in cells lining the respiratory tract. Research has shown that agents which stimulate the innate immune system may be useful for limiting respiratory infections, which may provide protection from infections both in isolation and during the period between inoculation and the formation of antibodies and immune cells. Such agents are considered to be useful for the treatment and/or prevention of respiratory infections, or respiratory conditions caused by or associated with infectious agents such as a virus (such as Influenza A) or bacterium (such as pneumonia) in a non-antigen specific manner.

In this regard, compounds of the invention as described herein have shown significantly improved activity, both activation of human TLR2 and inhibition of viral progression, compared to other TLR2 agonists such as Pam2Cys-Ser-K4, Pam2Cys-Ser-Ser-PEG and Pam3Cys-Ser-PEG (see Examples section).

As used herein, 'Ser' refers to the amino acid serine and 'Cys' refers to the amino acid cysteine.

As used herein, 'PEG' refers to the polymer compound polyethylene glycol. Unless otherwise defined, reference to 'PEG' includes any length polymer of ethylene oxide. Reference to PEG also includes substituted PEG.

In one aspect, therefore, the present invention provides a method of treating and/or preventing a disease, comprising raising an innate immune response in a subject by administering an effective amount of a compound of the invention as described herein or a pharmaceutically acceptable salt or prodrug thereof to the subject in need thereof.

In another aspect, the present invention provides a method of treating and/or preventing a disease caused by an infectious agent, comprising administering to a subject in need thereof an effective amount of a compound of the invention as described herein or a pharmaceutically acceptable salt or prodrug thereof.

In another aspect, the present invention provides a method of treating and/or preventing a respiratory disease or condition associated with a viral or bacterial infection, comprising administering to a subject in need thereof a compound of the invention as described herein or a pharmaceutically acceptable salt or prodrug thereof.

In another aspect, the present invention provides a method of treating and/or preventing a respiratory infection, comprising administering to a subject in need thereof a compound of the invention as described herein or a pharmaceutically acceptable salt or prodrug thereof. Preferably the method further comprises a step of identifying a subject having a respiratory infection.

In another aspect, the present invention provides a method for reducing airway inflammation, comprising administering to a subject in need thereof a compound of the invention as described herein or a pharmaceutically acceptable salt or prodrug thereof.

The present invention also provides a method of improving the ability of a subject to control a respiratory disease or condition during a respiratory viral infection, the method comprising administering to a subject in need thereof a compound of the invention as described herein or a pharmaceutically acceptable salt or prodrug thereof. Preferably the infection is not a rhinovirus infection.

The present invention also provides a method of treating and/or preventing a disease or condition associated with the TLR2 receptor, the method comprising administering to a subject in need thereof a compound of the invention as described herein or a pharmaceutically acceptable salt or prodrug thereof.

In another aspect, the present invention provides for use of a compound of the invention as described herein or a pharmaceutically acceptable salt or prodrug thereof in the preparation of a medicament for raising an innate immune response in a subject.

In another aspect, the present invention provides for use of a compound of the invention as described herein or a pharmaceutically acceptable salt or prodrug thereof in the preparation of a medicament for treating and/or preventing a disease caused by an infectious agent.

In another aspect, the present invention further provides for use of a compound of the invention as described herein or a pharmaceutically acceptable salt or prodrug thereof in the preparation of a medicament for treating and/or preventing a respiratory disease or condition associated with a viral or bacterial infection in a subject.

In another aspect, the present invention further provides for use of a compound of the invention as described herein or a pharmaceutically acceptable salt or prodrug thereof in the preparation of a medicament for treating and/or preventing a respiratory infection in a subject.

In yet another aspect, the present invention provides for use of a compound of the invention as described herein or a pharmaceutically acceptable salt or prodrug thereof in the preparation of a medicament for treating and/or preventing a respiratory infection.

In another aspect, the present invention further provides use of a compound of the invention as described herein or a pharmaceutically acceptable salt or prodrug thereof in the preparation of a medicament for reducing airway inflammation.

In another aspect, the present invention further provides use of a compound of the invention as described herein or a pharmaceutically acceptable salt or prodrug thereof in the preparation of a medicament for improving the ability of a subject to control a respiratory disease or condition during a respiratory viral infection. Preferably the infection is not a rhinovirus infection.

In another aspect, the present invention further provides use of a compound of the invention as described herein or a pharmaceutically acceptable salt or prodrug thereof in the preparation of a medicament for treating and/or preventing a disease or condition associated with the TLR2 receptor.

In one aspect, the present invention provides for use of a compound of the invention as described herein or a pharmaceutically acceptable salt or prodrug thereof, for raising an innate immune response in a subject.

In another aspect, the present invention provides for use of a compound of the invention as described herein or a pharmaceutically acceptable salt or prodrug thereof, for preventing a disease caused by an infectious agent, in a subject.

In another aspect, the present invention provides for use of a compound of the invention as described herein or a pharmaceutically acceptable salt or prodrug thereof, for treating and/or preventing a respiratory disease or condition associated with a viral or bacterial infection in a subject.

In a further aspect, the invention provides for use of a compound of the invention as described herein or a pharmaceutically acceptable salt or prodrug thereof, for (a) treating and/or preventing a respiratory infection in a subject; (b) reducing airway inflammation in a subject; (c) controlling a respiratory disease or condition during a respiratory viral infection in a subject; (d) for treating and/or preventing a disease or condition associated with the TLR2 receptor.

In any of these aspects, the compound may be administered in a composition. Typically, the composition further comprises a pharmaceutically acceptable carrier, diluent or excipient. The composition may be formulated for administration to the upper and/or lower respiratory tract, for example by inhalation or intranasally.

In any aspect of the present invention, the compound of the invention as described herein is the R diastereomer around the chiral centre of the 2,3-bis(palmitoyloxy)propyl moiety of the compound.

In any aspect of the present invention, the compound of the invention as described herein is the S diastereomer around the chiral centre of the 2,3-bis(palmitoyloxy)propyl moiety of the compound.

In any aspect of the present invention, a composition of the invention as described herein comprises a compound that is the R diastereomer around the chiral centre of the 2,3-bis(palmitoyloxy)propyl moiety of the compound.

In any aspect of the present invention, a composition of the invention as described herein comprises a compound that is the S diastereomer around the chiral centre of the 2,3-bis(palmitoyloxy)propyl moiety of the compound.

In any aspect of the present invention, 1%, 5%, 10%, 20%, 30%, 40%, 50%, 60%, 70%, 80%, 90%, 95%, 96%, 97%, 98%, 99% or more than 99% of the compound present in a composition is the R diastereomer around the chiral centre of the 2,3-bis(palmitoyloxy)propyl moiety of the compound.

In any aspect of the present invention, 1%, 5%, 10%, 20%, 30%, 40%, 50%, 60%, 70%, 80%, 90%, 95%, 96%, 97%, 98%, 99% or more than 99% of the compound present in a composition is the S diastereomer around the chiral centre of the 2,3-bis(palmitoyloxy)propyl moiety of the compound.

In any aspect of the present invention, the compound of the invention as described herein is the L diastereomer around the chiral centre of the cysteine analogue residue of the Pam2Cys analogue moiety compound.

In any aspect of the present invention, the compound of the invention as described herein is the L diastereomer around the chiral centre of the cysteine residue of the Pam2Cys moiety compound.

In any aspect of the present invention, the compound of the invention as described herein is the D diastereomer around the chiral centre of the cysteine analogue residue of the Pam2Cys analogue moiety compound.

In any aspect of the present invention, the compound of the invention as described herein is the D diastereomer around the chiral centre of the cysteine residue of the Pam2Cys moiety of the compound.

In any aspect of the present invention, a composition of the invention as described herein comprises a compound that is the L diastereomer around the chiral centre of the cysteine analogue residue of the Pam2Cys analogue moiety of the compound.

In any aspect of the present invention, a composition of the invention as described herein comprises a compound that is the L diastereomer around the chiral centre of the cysteine residue of the Pam2Cys moiety of the compound.

In any aspect of the present invention, a composition of the invention as described herein comprises a compound that is the D diastereomer around the chiral centre of the cysteine analogue residue of the Pam2Cys analogue moiety of the compound.

In any aspect of the present invention, a composition of the invention as described herein comprises a compound that is the D diastereomer around the chiral centre of the cysteine residue of the Pam2Cys moiety of the compound.

In any aspect of the present invention, 1%, 5%, 10%, 20%, 30%, 40%, 50%, 60%, 70%, 80%, 90%, 95%, 96%, 97%, 98%, 99% or more than 99% of the compound present in the composition is the L diastereomer around the chiral centre of the cysteine analogue residue of the Pam2Cys analogue moiety of the compound.

In any aspect of the present invention, 1%, 5%, 10%, 20%, 30%, 40%, 50%, 60%, 70%, 80%, 90%, 95%, 96%, 97%, 98%, 99% or more than 99% of the compound present in the composition is the L diastereomer around the chiral centre of the cysteine residue of the Pam2Cys moiety of the compound.

In any aspect of the present invention, 1%, 5%, 10%, 20%, 30%, 40%, 50%, 60%, 70%, 80%, 90%, 95%, 96%, 97%, 98%, 99% or more than 99% of the compound present in the composition is the D diastereomer around the chiral centre of the cysteine analogue residue of the Pam2Cys analogue moiety of the compound.

In any aspect of the present invention, 1%, 5%, 10%, 20%, 30%, 40%, 50%, 60%, 70%, 80%, 90%, 95%, 96%, 97%, 98%, 99% or more than 99% of the compound present in the composition is the D diastereomer around the chiral centre of the cysteine residue of the Pam2Cys moiety of the compound.

In any aspect of the present invention, the compound of the invention as described herein is the L diastereomer around the chiral centre of the Y moiety.

In any aspect of the present invention, the compound of the invention as described herein is the D diastereomer around the chiral centre of the Y moiety.

In any aspect of the present invention, a composition of the invention as described herein comprises a compound that is the L diastereomer around the chiral centre of the Y moiety.

In any aspect of the present invention, a composition of the invention as described herein comprises a compound that is the D diastereomer around the chiral centre of the Y moiety.

In any aspect of the present invention, 1%, 5%, 10%, 20%, 30%, 40%, 50%, 60%, 70%, 80%, 90%, 95%, 96%, 97%, 98%, 99% or more than 99% of the compound present in the composition is the L diastereomer around the chiral centre of the Y moiety.

In any aspect of the present invention, 1%, 5%, 10%, 20%, 30%, 40%, 50%, 60%, 70%, 80%, 90%, 95%, 96%, 97%, 98%, 99% or more than 99% of the compound present in the composition is the D diastereomer around the chiral centre of the Y moiety.

In any aspect of the invention, the compound of the invention as described herein or a pharmaceutically acceptable salt or prodrug thereof may be conjugated with other compounds. Other compounds are any of those described herein.

In any aspect of the invention, the compound of the invention as described herein or a pharmaceutically acceptable salt or prodrug thereof is administered once daily or once weekly.

In any aspect of the invention, where prevention or prophylaxis is intended or required, the compound is administered to the subject before any clinically or biochemically detectable symptoms of viral infection.

In any aspect of the invention, administration of the compound of the invention as described herein or a pharmaceutically acceptable salt or prodrug thereof to a subject reduces viral load in a subject. Preferably, the viral load is reduced in the respiratory tract, for example the upper and/or lower respiratory tract. Preferably, the viral load is reduced in the lungs.

In any aspect herein, the infectious agent may be a virus. Preferably, the virus is one associated with infection of the respiratory tract. Even more preferably, the virus is influenza. In any aspect, the virus is not a rhinovirus.

Influenza (commonly referred to as "the flu") is an infectious disease caused by RNA viruses of the family Orthomyxoviridae (the influenza viruses) that affects birds and mammals. The most common symptoms of the disease are chills, fever, sore throat, muscle pains, severe headache, coughing, weakness/fatigue and general discomfort.

The influenza viruses make up three of the five genera of the family Orthomyxoviridae. Influenza Type A and Type B viruses co-circulate during seasonal epidemics and can cause severe influenza infection. Influenza Type C virus infection is less common but can be severe and cause local epidemics.

Influenza Type A virus can be subdivided into different serotypes or subtypes based on the antibody response to these viruses. Influenza A viruses are divided into subtypes based on two proteins on the surface of the virus: the hemagglutinin (H) and the neuraminidase (N). There are 18 different hemagglutinin subtypes and 11 different neuraminidase subtypes. (H1 through H18 and N1 through N11 respectively.) The sub types that have been confirmed in humans are H1N1, H1N2, H2N2, H3N2, H5N1, H7N2, H7N3, H7N7, H9N2 and H10N7.

Influenza has an enormous impact on public health with severe economic implications in addition to the devastating health problems, including morbidity and even mortality. Accordingly, there is a need for therapeutic agents which can prevent infection, or reduce severity of infection in individuals.

In any aspect or embodiment of the invention, the influenza infection for which treatment or prevention is required is an infection with a virus selected from the group consisting of influenza Types A, B or C.

The term 'respiratory disease' or 'respiratory condition' refers to any one of several ailments that involve inflammation and affect a component of the respiratory system including the upper (including the nasal cavity, pharynx and larynx) and lower respiratory tract (including trachea, bronchi and lungs). The inflammation in the upper and lower respiratory tract may be associated with or caused by viral infection or an allergen. It is expected that the anti-inflammatory activity of the compounds either alone or when co-administered with a glucocorticoid would make them particularly suitable for treatment of these disease or conditions.

A symptom of respiratory disease may include cough, excess sputum production, a sense of breathlessness or chest tightness with audible wheeze. Exercise capacity may be quite limited. In asthma the FEV1.0 (forced expiratory volume in one second) as a percentage of that predicted nomographically based on weight, height and age, may be decreased as may the peak expiratory flow rate in a forced expiration. In COPD the FEV1.0 as a ratio of the FVC is typically reduced to less than 0.7. The impact of each of these conditions may also be measured by days of lost work/school, disturbed sleep, requirement for bronchodilator drugs, requirement for glucocorticoids including oral glucocorticoids.

The existence of, improvement in, treatment of or prevention of a respiratory disease may be determined by any clinically or biochemically relevant method of the subject or a biopsy therefrom. For example, a parameter measured may be the presence or degree of lung function, signs and symptoms of obstruction; exercise tolerance; night time awakenings; days lost to school or work; bronchodilator usage; Inhaled corticosteroid (ICS) dose; oral glucocorticoid (GC) usage; need for other medications; need for medical treatment; hospital admission.

As used herein, the term respiratory infection means an infection by virus or bacteria anywhere in the respiratory tract. Examples of respiratory infection include but are not limited to colds, sinusitis, throat infection, tonsillitis, laryngitis, bronchitis, pneumonia or bronchiolitis. Preferably, in any embodiment of the invention the respiratory infection is a cold.

An individual may be identified as having a respiratory tract infection by viral testing and may exhibit symptoms of itchy watery eyes, nasal discharge, nasal congestion, sneezing, sore throat, cough, headache, fever, malaise, fatigue and weakness. In one aspect, a subject having a respiratory infection may not have any other respiratory condition. Detection of the presence or amount of virus may be by PCR/sequencing of RNA isolated from clinical samples (nasal wash, sputum, BAL) or serology.

The term "pharmaceutically acceptable" may be used to describe any pharmaceutically acceptable salt, hydrate or prodrug, or any other compound which upon administration to a subject, is capable of providing (directly or indirectly) a compound of the invention as described herein, or a pharmaceutically acceptable salt or prodrug thereof, or an active metabolite or residue thereof.

Suitable pharmaceutically acceptable salts may include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Base salts may include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine. General information on types of pharmaceutically acceptable salts and their formation is known to those skilled in the art and is as described in general texts such as "Handbook of Pharmaceutical salts" P. H. Stahl, C. G. Wermuth, 1st edition, 2002, Wiley-VCH.

In the case of compounds that are solids, it will be understood by those skilled in the art that the inventive compounds, agents and salts may exist in different crystalline or polymorphic forms, all of which are intended to be within the scope of the present invention and specified formulae.

The term "polymorph" includes any crystalline form of compounds of the invention as described herein, such as anhydrous forms, hydrous forms, solvate forms and mixed solvate forms.

Formula (I), Formula (II), Formula (III), Formula (IV) and/or Formula (V) are intended to cover, where applicable, solvated as well as unsolvated forms of the compounds. Thus, Formula (I), Formula (II), Formula (III), Formula (IV) and/or Formula (V) include compounds having the indicated structures, including the hydrated or solvated forms, as well as the non-hydrated and non-solvated forms.

As used herein, the term "solvate" refers to a complex of variable stoichiometry formed by a solute (in this invention, a compound of Formula (I), Formula (II), Formula (III), Formula (IV) and/or Formula (V), or a pharmaceutically acceptable salt or prodrug thereof and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

Basic nitrogen-containing groups may be quaternised with such agents as lower alkyl halide, such as methyl, ethyl, propyl, and butyl chlorides, bromides and iodides; dialkyl sulfates like dimethyl and diethyl sulfate; and others.

The compounds as described herein are to also include isotope variations, such as the replacement of hydrogen for deuterium.

Compounds of the present invention may exist in and be isolated in optically active and racemic forms. As would be understood by a person skilled in the art, the present invention is intended to encompass any racemic, optically active or stereoisomeric form, or mixtures thereof, of compounds of Formula (I), (II), (III), (IV) and/or (V) which possess the useful properties described herein. It is well known in the art how to prepare such forms (for example, by resolution of racemic mixtures by recrystallization, by synthesis from optically-active starting materials, by chiral synthesis, or by chiral chromatographic separation). In one preferred embodiment, with regard to the carbon shown with a * below, the compound of the present invention is provided in a racemic mixture. In another preferred aspect, the compound of the present invention contains

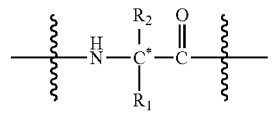

provided with excess of, or only, the L-configuration or naturally occurring amino acid.

A "prodrug" is a compound that may not fully satisfy the structural requirements of the compounds provided herein, but is modified in vivo, following administration to a subject or patient, to produce a compound of the invention as described herein. For example, a prodrug may be an acylated derivative of a compound as provided herein. Prodrugs include compounds wherein hydroxy, carboxy, amine or sulfhydryl groups are bonded to any group that, when administered to a mammalian subject, cleaves to form a free hydroxy, carboxy, amino, or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to generate the parent compounds.

Prodrugs include compounds wherein an amino acid residue, or a polypeptide chain of two or more (eg, two, three or four) amino acid residues which are covalently joined to free amino, and amido groups of compounds of Formula (I). The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of Formula (I), Formula (II), Formula (III), Formula (IV) and/or Formula (V), or other structure as depicted herein.

The compounds of the invention as described herein or a pharmaceutically acceptable salt or prodrug thereof may be covalent irreversible or covalent reversible agonists of the active site of a protein.

Where a protecting group (PG) is referred to, a person skilled in the art would readily understand what type of protecting group would be suitable. Examples of suitable protecting groups for the purposes described herein include (but are not limited to) tert-butyloxycarbonyl (t-Boc) and 9H-fluoren-9-ylmethoxycarbonyl (Fmoc). Most preferably, Fmoc is used herein.

Pharmaceutical compositions may be formulated from compounds of the invention as described herein for any appropriate route of administration including, for example, topical (for example, transdermal or ocular), oral, buccal, respiratory (for example, nasal, inhalation, intrapulmonary), vaginal, rectal or parenteral administration. The term parenteral as used herein includes subcutaneous, intradermal, intravascular (for example, intravenous), intramuscular, spinal, intracranial, intrathecal, intraocular, periocular, intraorbital, intrasynovial and intraperitoneal injection, as well as any similar injection or infusion technique. Suitable oral forms include, for example, tablets, troches, lozenges, aqueous or oily suspensions, dispersible powders or granules, emulsions, hard or soft capsules, or syrups or elixirs. For intravenous, intramuscular, subcutaneous, or intraperitoneal administration, one or more compounds may be combined with a sterile aqueous solution which is preferably isotonic with the blood of the recipient. Such formulations may be prepared by dissolving solid active ingredient in water containing physiologically compatible substances such as sodium chloride or glycine, and having a buffered pH compatible with physiological conditions to produce an aqueous solution, and rendering said solution sterile. The formulations may be present in unit or multi-dose containers such as sealed ampoules or vials. Examples of components are described in Martindale—The Extra Pharmacopoeia (Pharmaceutical Press, London 1993) and Martin (ed.), Remington's Pharmaceutical Sciences. Preferably, the compositions are formulated for administration to the respiratory tract, for example, by intrapulmonary administration (eg. inhalation) or intranasal administration. The compositions may be administered to the upper and/or lower respiratory tract.

Preferably, the pharmaceutical compositions are in a form suitable for administration via the respiratory route, and may be in any form such as a powder, liquid or suspension. Such compositions may target tissue including pulmonary tissue (including alveolus, terminal bronchiole, bronchiole, and bronchus) or the nasal cavity (including paranasal cavity, frontal sinus, ethmoid sinus, maxillary sinus, sphenoidal sinus, superior turbinate, middle turbinate, and inferior turbinate).

In the context of this specification the term "administering" and variations of that term including "administer" and "administration", includes contacting, applying, delivering or providing a compound or composition of the invention to an organism, or a surface by any appropriate means.

The dose of the biologically active compound according to the invention may vary within wide limits and may be adjusted to individual requirements. Active compounds according to the present invention are generally administered in a therapeutically effective amount.

A composition according to the present invention is to be administered in an effective amount. The phrase 'therapeutically effective amount' or 'effective amount' generally refers to an amount of a compound of the invention described herein, a pharmaceutically acceptable salt, polymorph or prodrug thereof of the present invention that (i) treats the particular disease, condition, or disorder, (ii) attenuates, ameliorates, or eliminates one or more symptoms of the particular disease, condition, or disorder, or (iii) delays the onset of one or more symptoms of the particular disease, condition, or disorder described herein. Undesirable effects, e.g. side effects, are sometimes manifested along with the desired therapeutic effect; hence, a practitioner balances the potential benefits against the potential risks in determining what is an appropriate "effective amount".

The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation. In one aspect, the dose administered to a subject is any dose that reduces viral load. Preferably, the dose does not significantly increase inflammation, for example does not significantly increase absolute neutrophil numbers or the proportion of neutrophils of total BAL cells in the lung. The terms "therapeutically effective amount" or "effective amount" may also refer to an amount of the compound of Formula (I), Formula (II), Formula (III), Formula (IV) and/or Formula (V) or a pharmaceutically acceptable salt or prodrug thereof, that results in an improvement or remediation of the symptoms of a respiratory infection, or respiratory disease or condition associated with a viral or bacterial infection.

In some embodiments, an effective amount for a human subject lies in the range of about 250 nmoles/kg body weight/dose to 0.005 nmoles/kg body weight/dose. Preferably, the range is about 250 nmoles/kg body weight/dose to 0.05 nmoles/kg body weight/dose. In some embodiments, the body weight/dose range is about 250 nmoles/kg, to 0.1 nmoles/kg, about 50 nmoles/kg to 0.1 nmoles/kg, about 5 nmoles/kg to 0.1 nmol/kg, about 2.5 nmoles/kg to 0.25 nmoles/kg, or about 0.5 nmoles/kg to 0.1 nmoles/kg body weight/dose. In some embodiments, the amount is at, or about, 250 nmoles, 50 nmoles, 5 nmoles, 2.5 nmoles, 0.5 nmoles, 0.25 nmoles, 0.1 nmoles or 0.05 nmoles/kg body weight/dose of the compound. Dosage regimes are adjusted to suit the exigencies of the situation and may be adjusted to produce the optimum therapeutic dose.

Compounds of the invention described herein may be compositions formulated as inhaled formulations, including dry powder, sprays, mists, or aerosols. This may be particularly preferred for treatment of a respiratory infection. For inhalation formulations, the composition or combination provided herein may be delivered via any inhalation methods known to a person skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent such as isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient. Alternatively, the composition may be a dry powder and administered to the respiratory tract as defined herein.

It will be understood, that the specific dose level for any particular patient will depend upon a variety of factors including the activity of the specific compound employed, the age, body weight, general health, sex, diet, time of administration, route of administration, and rate of excretion, drug combination (i.e. other drugs being used to treat the patient), and the severity of the particular disorder undergoing therapy.

It will be understood, however, that the specific dose level for any particular subject will depend upon a variety of factors including the activity of the specific compound employed, the age, body weight, general health, sex, diet, time of administration, route of administration, and rate of excretion, drug combination (i.e. other drugs being used to treat the subject), and the severity of the particular disorder undergoing therapy. The dosage will generally be lower if the compounds are administered locally rather than systemically, and for prevention rather than for treatment. Such treatments may be administered as often as necessary and for the period of time judged necessary by the treating physician. A person skilled in the art will appreciate that the dosage regime or therapeutically effective amount of the compound of Formula (I), Formula (II), Formula (III), Formula (IV), Formula (V), Formula (VI), Formula (VII), Formula (VIII) and/or Formula (X), or a pharmaceutically acceptable salt or prodrug thereof, to be administered may need to be optimized for each individual. The pharmaceutical compositions may contain active ingredient in the range of about 0.1 to 2000 mg, preferably in the range of about 0.5 to 500 mg and most preferably between about 1 and 200 mg.

A daily dose of about 0.01 to 100 mg/kg body weight, preferably between about 0.1 and about 50 mg/kg body weight, may be appropriate. The daily dose can be administered in a single or multiple doses per day.

It will also be appreciated that different dosages may be required for treating different disorders.

As used herein, the terms "treatment" or "treating" of a subject includes the application or administration of a compound or composition of the invention to a subject (or application or administration of a compound of the invention to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians.

"Subject" includes any human or non-human animal. Thus, in addition to being useful for human treatment, the compounds of the present invention may also be useful for veterinary treatment of mammals, including companion animals and farm animals, such as, but not limited to dogs, cats, horses, cows, sheep, and pigs.

The compounds of the present invention may be administered along with a pharmaceutical carrier, diluent or excipient as described above.

In yet another aspect, the present invention provides a process for preparing a compound of formula (I):

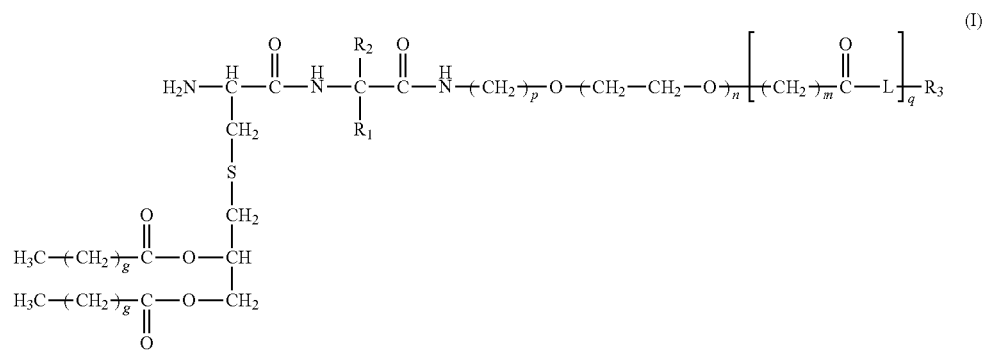

wherein
n is 3 to 100;
m is 1, 2, 3 or 4;
each g is independently 10, 11, 12, 13, 14, 15, 16, 17 or 18;
p is 2, 3 or 4;
q is null or 1;
$R_1$ and $R_2$ are independently selected from the group consisting of H, —$CH_2OH$, —$CH_2CH_2OH$, —$CH(CH_3)OH$ and —$CH_2OPO(OH)_2$, wherein any one of the alkyl hydrogens can be replaced with a halogen, and wherein $R_1$ and $R_2$ are not both H;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

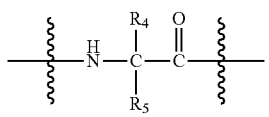

wherein $R_4$ is H; and
$R_5$ is the side chain, or second hydrogen of the amino acid,
the process comprising
a) coupling PG-NH—(PEG)$_n$-COOH to a solid phase support;
b) removing PG;
c) coupling PG1-NH—$CR_1R_2$—COOH to the PEG;
d) removing PG1;
e) coupling PG2-Dhc-OH;
f) palmitoylation of the Dhc
g) removing PG2; and
h) removing the compound from the solid phase support,
wherein PG is a protecting group.

In one embodiment, the present invention provides a process for preparing a compound with the structure:

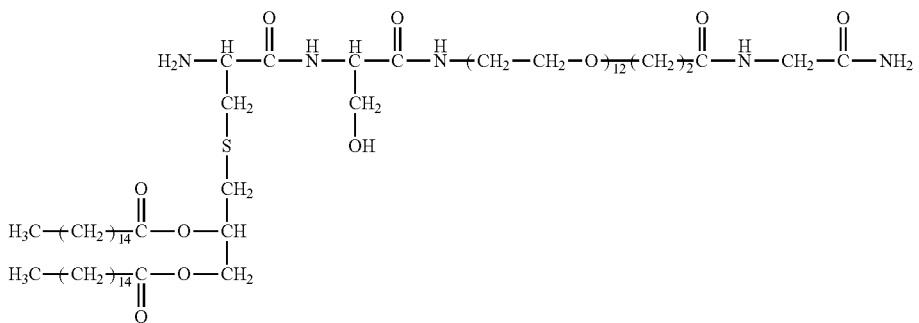

the process comprising
a) coupling Fmoc-Gly-OH to a TentaGel S RAM solid phase support;
b) removing the Fmoc group from the Gly;
c) coupling Fmoc-NH—(PEG)$_{11}$-COOH of the structure

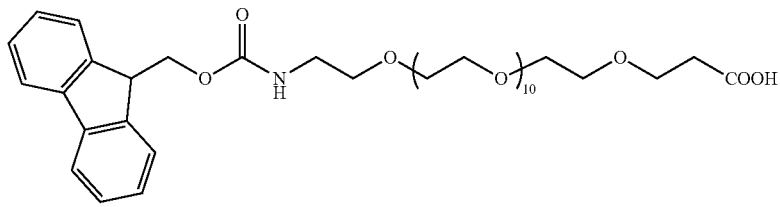

to the Gly;
d) removing the Fmoc group from the PEG;
e) coupling Fmoc-Ser(tBu)—OH to the PEG;
f) removing the Fmoc group from the Ser;
g) coupling Fmoc-Dhc-OH to the Ser;
h) palmitoylation of the Dhc
i) removing the Fmoc group from the Dhc; and
j) removal of the compound from the solid phase support.

In yet another aspect, the present invention provides a process for preparing a compound of formula (X):

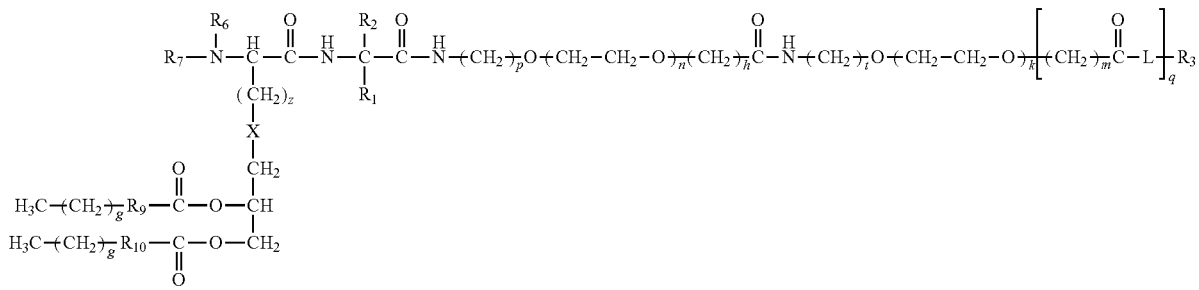

wherein n is 3 to 100;

k is 3 to 100;

m is 1, 2, 3 or 4;

each g is independently 10, 11, 12, 13, 14, 15, 16, 17 or 18;

p is 2, 3 or 4;

t is 2, 3 or 4;

h is 1, 2, 3 or 4;

q is null or 1;

$R_1$ and $R_2$ are independently selected from the group consisting of H, —CH$_2$OH, —CH$_2$CH$_2$OH, —CH(CH$_3$)OH, —CH$_2$OPO(OH)$_2$, —CH$_2$C(=O)NH$_2$, —CH$_2$CH$_2$C(=O)OH and —CH$_2$CH$_2$C(=O)OR$_8$, wherein any one of the alkyl hydrogens can be replaced with a halogen;

$R_6$ and $R_7$ are independently selected from the group consisting of H, a straight or branched C$_1$-C$_4$ alkyl, and —C(=O)CH$_3$;

$R_8$ is selected from the group consisting of H and a straight or branched C$_1$-C$_6$ alkyl;

$R_9$ and $R_{10}$ are independently selected from the group consisting of —NH—, —O— or a single bond;

z is 1 or 2;
X is S or S(=O);
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

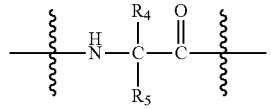

wherein $R_4$ is H; and
$R_5$ is the side chain, or second hydrogen of the amino acid, the process comprising
a) coupling PG-NH—$(PEG)_n$-COOH to a solid phase support;
b) removing PG;
c) coupling PG1-NH—$(PEG)_n$-COOH;
d) removing PG1;
e) coupling PG2-NH—$CR_1R_2$—COOH to the PEG;
f) removing PG2;
g) coupling PG3-(2,3-dihydroxypropyl cysteine analogue)-OH;
h) adding $H_3C(CH_2)_gR_9C$(=O)OH and $H_3C(CH_2)_gR_{10}C$(=O)OH to the 2,3-dihydroxypropyl cysteine analogue;
i) removing PG3; and
j) removing the compound from the solid phase support, wherein PG is a protecting group.

The above process may also include the step of acylation of the amine group of the cysteine moiety before removing the compound from the solid phase support.

In another embodiment of the invention, the above process may include the step of alkylation of the amine group of the cysteine moiety before removing the compound from the solid phase support.

In another embodiment of the invention, the above process may include the step of oxidation of the sulphur atom of the cysteine moiety before removing the compound from the solid phase support.

In another aspect, the present invention provides a compound with the structure:

wherein
n is 3 to 100;
m is 1, 2, 3 or 4;
each g is independently 10, 11, 12, 13, 14, 15, 16, 17 or 18;
p is 2, 3 or 4;
q is null or 1;
$R_1$ and $R_2$ are independently selected from the group consisting of H, —$CH_2OH$, —$CH_2CH_2OH$, —CH($CH_3$)OH and —$CH_2OPO(OH)_2$, wherein any one of the alkyl hydrogens can be replaced with a halogen, and wherein $R_1$ and $R_2$ are not both H;
wherein when q=1, $R_3$ is —$NH_2$ or —OH;
wherein when q=0, $R_3$ is H;
L is null or consists of 1 to 10 units, wherein each unit is a natural alpha amino acid or derived from a natural alpha amino acid, and has the formula:

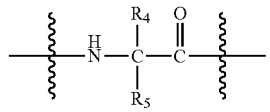

wherein $R_4$ is H; and
$R_5$ is the side chain, or second hydrogen of the amino acid,
prepared by a process described herein.

The present invention also provides a process for preparing any one of INNA-006, INNA-009, INNA-010, INNA-011, INNA-012, INNA-013, INNA-014 and INNA-015 shown below, the process comprising the steps described in Example 1.

The present invention also provides a compound with the structure of any one of INNA-006, INNA-009, INNA-010, INNA-011, INNA-012, INNA-013, INNA-014 and INNA-015 as described below, prepared by a process described herein.

The table below summarises various compounds referred to herein. Compounds shown as INNA-006, INNA-009, INNA-010, INNA-011, INNA-012, INNA-013, INNA-014 and INNA-015 are compounds of the invention.

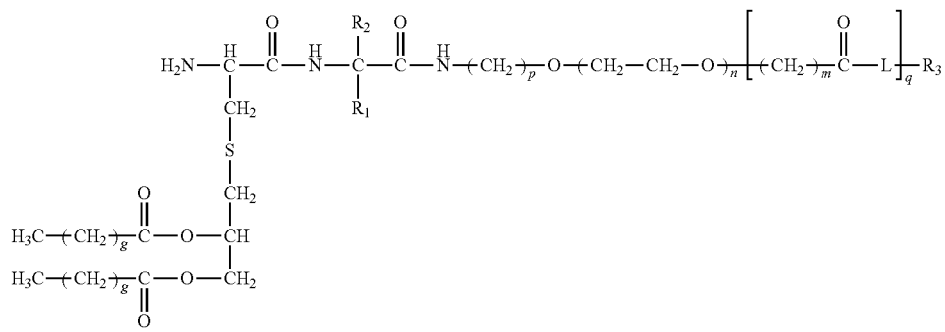

| Compound Structure | Compound name |
|---|---|
| R-K-K-K-K-NH$_2$ branched structure with R-K groups and Pam$_2$Cys—Ser—Ser branch | INNA-001 |
| Branched R-K structure with Pam$_2$Cys—Ser—Ser branch, linked to —NH—(CH$_2$—CH$_2$—O)$_{12}$—CH$_2$—CH$_2$—C(O)—NH—CH$_2$—C(O)—NH$_2$ | INNA-002 |
| Pam$_2$Cys—Ser—Ser—NH—(CH$_2$—CH$_2$—O)$_{12}$—CH$_2$—CH$_2$—C(O)—NH—CH$_2$—C(O)—NH$_2$ | INNA-003 |
| Pam$_2$Cys—Ser—Ser—Lys—Lys—Lys—Lys | INNA-004 |
| Pam$_2$Cys—Ser—Lys—Lys—Lys—Lys | INNA-005 |
| Pam$_2$Cys—Ser—NH—(CH$_2$—CH$_2$—O)$_{12}$—CH$_2$—CH$_2$—C(O)—NH—CH$_2$—C(O)—NH$_2$ | INNA-006 (also shown herein as compound (1)) |
| Branched R-K structure with Pam$_2$Cys—Ser branch, terminating in —NH$_2$ | INNA-007 |
| Branched R-K structure with Pam$_2$Cys—Ser branch, linked to —NH—(CH$_2$—CH$_2$—O)$_{12}$—CH$_2$—CH$_2$—C(O)—NH—CH$_2$—C(O)—NH$_2$ | INNA-008 |
| Pam2Cys-Ser—NH—(CH$_2$—CH$_2$—O)$_4$—CH$_2$—CH$_2$—C(O)—NH—CH$_2$—C(O)—NH$_2$ | INNA-009 |
| Pam2Cys-Ser—NH—(CH$_2$—CH$_2$—O)$_6$—CH$_2$—CH$_2$—C(O)—NH—CH$_2$—C(O)—NH$_2$ | INNA-010 |
| Pam2Cys-Ser—NH—(CH$_2$—CH$_2$—O)$_{28}$—CH$_2$—CH$_2$—C(O)—NH—CH$_2$—C(O)—NH$_2$ | INNA-011 (also shown herein as compound (5)) |
| Pam2Cys-Ser—NH—(CH$_2$—CH$_2$—O)$_{28}$—CH$_2$—CH$_2$—C(O)—NH—(CH$_2$—CH$_2$—O)$_{28}$—CH$_2$—CH$_2$—C(O)—NH—CH$_2$—C(O)—NH$_2$ | INNA-012 (also shown herein as compound (6)) |

-continued

| Compound Structure | Compound name |
|---|---|
| Pam2Cys-Ser(PO)—NH—(CH$_2$—CH$_2$—O)$_{12}$—CH$_2$—CH$_2$—C(=O)—NH—CH$_2$—C(=O)—NH$_2$ | INNA-013 (also shown herein as compound (4)) |
| Pam2Cys-homoSer—NH—(CH$_2$—CH$_2$—O)$_{12}$—CH$_2$—CH$_2$—C(=O)—NH—CH$_2$—C(=O)—NH$_2$ | INNA-014 (also shown herein as compound (3)) |
| Pam2Cys-Thr—NH—(CH$_2$—CH$_2$—O)$_{12}$—CH$_2$—CH$_2$—C(=O)—NH—CH$_2$—C(=O)—NH$_2$ | INNA-015 (also shown herein as compound (2)) |
| CH$_3$—NH—CH(CH$_2$-S-CH$_2$-C*H(O-CO-(CH$_2$)$_{14}$-CH$_3$)-CH$_2$-O-CO-(CH$_2$)$_{14}$-CH$_3$)—C(=O)—NH—C*H(CH$_2$OH)—C(=O)—NH—(CH$_2$—CH$_2$—O)$_{12}$—CH$_2$—CH$_2$—C(=O)—NH—CH$_2$—C(=O)—NH$_2$ | N-Me-cysteine-INNA-006 (also shown herein as compound (9)) |
| NH$_2$—CH(CH$_2$-CH$_2$-S-CH$_2$-C*H(O-CO-(CH$_2$)$_{14}$-CH$_3$)-CH$_2$-O-CO-(CH$_2$)$_{14}$-CH$_3$)—C(=O)—NH—C*H(CH$_2$OH)—C(=O)—NH—(CH$_2$—CH$_2$—O)$_{12}$—CH$_2$—CH$_2$—C(=O)—NH—CH$_2$—C(=O)—NH$_2$ | L-Homo-cysteine-INNA-006 (also shown herein as compound (10)) |
| CH$_3$—C(=O)—NH—CH—C(=O)—NH—CH(CH$_2$-S-CH$_2$-CH(O-CO-(CH$_2$)$_{14}$-CH$_3$)-CH$_2$-O-CO-(CH$_2$)$_{14}$-CH$_3$)—C(=O)—NH—CH(CH$_2$OH)—C(=O)—NH—(CH$_2$—CH$_2$—O)$_{28}$—CH$_2$—CH$_2$—C(=O)—NH—CH$_2$—C(=O)—NH$_2$ | N-acetyl-INNA-011 (also shown herein as compound (11)) |

| Compound Structure | Compound name |
|---|---|
| (structure) | N-methyl-INNA-011 (also shown herein as compound (12)) |
| (structure) | N,N-dimethyl-NH₂INNA-011 (also shown herein as compound (13)) |
| (structure) | Sulfoxide-INNA-011 (also shown herein as compound (14)) |

It will be understood that the invention disclosed and defined in this specification extends to all alternative combinations of two or more of the individual features mentioned or evident from the text or drawings. All of these different combinations constitute various alternative aspects of the invention.

EXAMPLES

Example 1—Synthesis of Compounds

Synthesis of INNA-003 and INNA-006

Reagents: Solid phase support: TentaGel S RAM resin (substitution factor 0.24 mmol/g; Rapp Polymere, Tübingen, Germany). Amino acid derivatives: Fmoc-Gly-OH, Fmoc-Ser(tBu)—OH, Fmoc-homo-Ser(tBu)—OH, Fmoc-Ser(PO(OBzl)OH)—OH, Fmoc-Thr(tBu)—OH, Fmoc-NH—(PEG)$_3$-COOH, Fmoc-NH—(PEG)$_5$-COOH, Fmoc-NH—(PEG)$_{11}$-COOH, Fmoc-NH—(PEG)$_{27}$-COOH from Merck (Darmstadt, Germany).

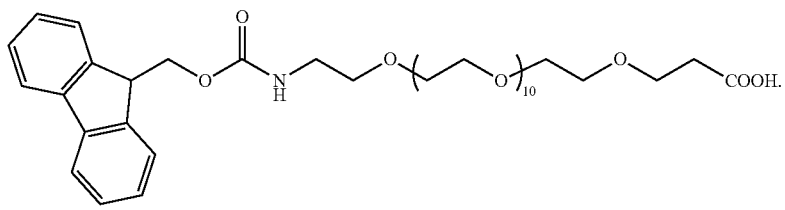
NB use of Merck catalogue number 851024 with its structure shown above gives rise to the structures shown below as "INNA-003" (which may also be referred to herein as Pam2Cys-Ser-Ser-PEG) and "INNA-006" (which may also be referred to herein as Pam2Cys-Ser-PEG).
INNA-003:
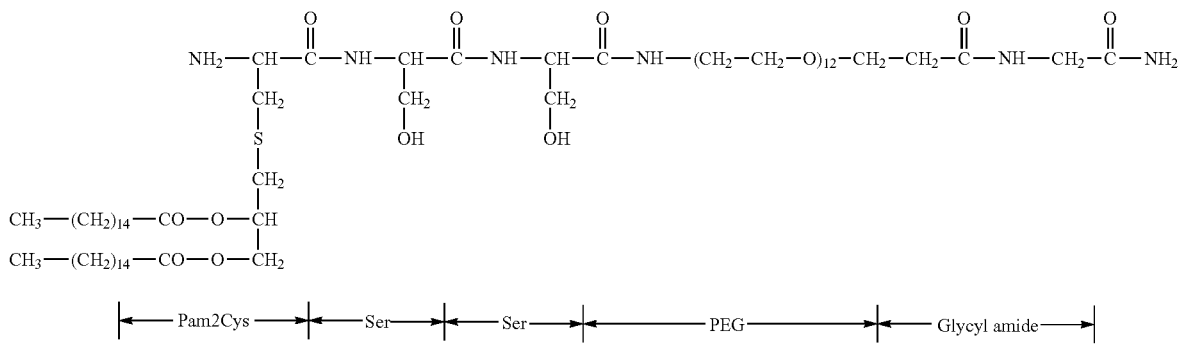
INNA-006, or compound (1):
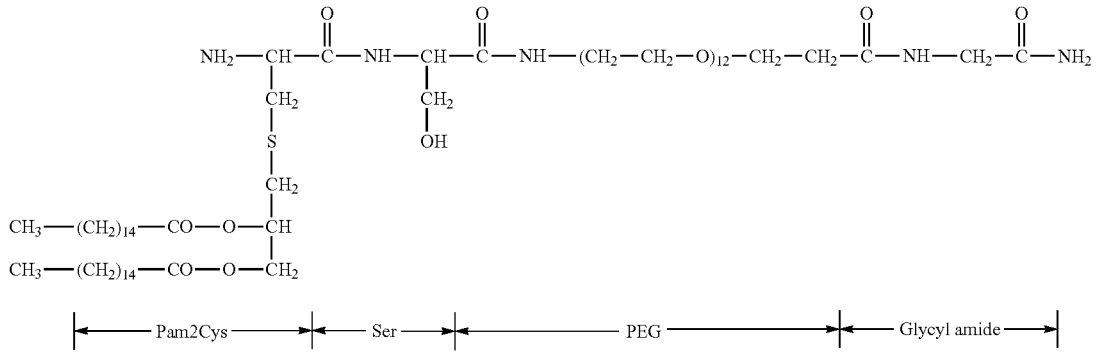

Acylation: A 4-fold molar excess of Fmoc amino acid, O-benzotriazole-N,N,N',N'-tetramethyl-uroniumhexafluorophosphate (HBTU) and a 6-fold molar excess of diisopropylethylamine (DIPEA) are used in all acylation steps. All acylation reactions are carried out for 60 minutes and completion of reaction confirmed by trinitrobenezene sulfonic acid (TNBSA) test. Removal of the Fmoc protective group from α-amino groups is achieved by exposing the solid phase support to 2.5% diazabicyclo[5.4.0]undec-7-ene (DBU; Sigma, Steinheim, Germany) for 2×5 minutes. dimethylformamide (DMF; Auspep, Melbourne, Australia) is used to wash the solid phase support between each acylation and de-protection step. The coupling of Fmoc-NH—(PEG)$_{11}$-COOH or other PEGylated amino acid derivatives (Merck, Darmstadt, Germany) is carried out in the same way as coupling amino acids.

NB. Glycine is first coupled to the TentaGel S RAM solid phase support followed by Fmoc-NH—(PEG)$_{11}$-COOH and other PEGylated amino acid derivatives.

Peptide Quantitation

Quantitation of peptide-based materials was determined by amino acid analysis performed in vacuo by hydrolysis of samples at 110° C. in sealed glass vials in the presence of 6N HCl containing 0.1% phenol. Derivatisation of amino acids was then carried out using Waters AccQTag reagents according to the manufacturer's instructions followed by analysis on a Waters Acquity UPLC System (Waters Millipore) using an AccQTag ultra column (2.1 mm×100 mm; Waters Millipore).

Preparation of INNA-003 and INNA-006

In the case of INNA-003 two serine residues are coupled seriatim following addition of the PEG moiety and in the case of INNA-006 a single serine is incorporated following addition of the PEG moiety.

Lipidation (Addition of Pam2Cys).

Synthesis of S-(2,3-dihydroxypropyl)cysteine: Triethylamine (6 g, 8.2 ml, 58 mmoles) is added to L-cysteine hydrochloride (3 g, 19 mmoles) and 3-bromo-propan-1,2-diol (4.2 g, 2.36 ml, 27 mmole) in water and the homogeneous solution kept at room temperature for 3 days. The solution is reduced in vacuo at 40° C. to a white residue which is then precipitated with acetone (300 ml) and the precipitate isolated by centrifugation. The precipitate is washed with acetone twice more and dried to yield S-(2,3-dihydroxypropyl)cysteine as a white amorphous powder.

Synthesis of N-Fluorenylmethoxycarbonyl-S-(23-dihydroxypropyl)-cysteine (Fmoc-Dhc-OH): S-(2,3-dihydroxypropyl) cysteine (2.45 g, 12.6 mmole) is dissolved in 9% sodium carbonate (20 ml). A solution of fluorenylmethoxycarbonyl-N-hydroxysuccinimide (3.45 g, 10.5 mmole) in acetonitrile (20 ml) is then added and the mixture stirred for 2 h, diluted with water (240 ml) and extracted with diethyl ether (25 ml×3). The aqueous phase is acidified to pH 2 with concentrated hydrochloric acid and then extracted with ethyl acetate (70 ml×3). The extract is washed with water (50 ml×2) and saturated sodium chloride solution (50 ml×2). The extract is dried over anhydrous sodium sulphate and evaporated to dryness. The final product is obtained by applying high vacuum to remove residual solvent.

Coupling of Fmoc-Dhc-OH to resin-bound peptide: Fmoc-Dhc-OH (100 mg, 0.24 mmole) is activated in DCM and DMF (1:1, v/v, 3 mL) with HOBt (36 mg, 0.24 mmole) and DICl (37 uL, 0.24 mmole) at 0° C. for 5 min. The mixture is then added to a vessel containing the resin-bound peptide (0.04 mmole, 0.25 g amino-peptide resin). After shaking for 2 h the solution is removed by filtration on a glass sinter funnel (porosity 3) and the resin washed with DCM and DMF (3×30 mL each). The reaction is monitored for completion using the TNBSA test. If necessary a double coupling is performed.

Palmitoylation of the two hydroxyl groups of the Fmoc-Dhc-peptide resin: Palmitic acid (204 mg, 0.8 mmole), DIPCDl (154 uL, 1 mmole) and DMAP (9.76 mg, 0.08_mmole) are dissolved in 2 mL of DCM and 1 mL of DMF. The resin-bound Fmoc-Dhc-peptide_resin (0.04 mmole, 0.25 g) is suspended in this solution and shaken for 16 h at room temperature. The solution is removed by filtration and the resin then washed with DCM and DMF thoroughly to remove any residue of urea. The removal of the Fmoc group is accomplished with 2.5% DBU (2×5 min).

Cleavage of peptide from the solid support: Reagent B (93% TFA, 5% water and 2% triisopropylsilane) for two hours. NB the peptide will not precipitate in chilled ether. Most of the TFA must be removed and then the residue is dissolved in 50% acetonitrile and purified immediately or freeze-dried.

Purification and Characterisation of INNA-003 and INNA-006:

Following cleavage from the solid support, INNA-003 and INNA-006 were purified by reversed-phase high-performance liquid chromatography using a C4 VYDAC column (10 mm×250 mm; Alltech, NSW, Australia) installed in a Waters HPLC system (Waters Millipore, Milford, MA, USA). Identity of the target materials were determined by mass spectrometry and the purified material was then characterised by analytical HPLC using a VYDAC C8 column (4.6 mm×250 mm) and found to be greater than 95%. Mass analysis was carried out using an Agilent 1100 Series LC/MSD ion-trap mass spectrometer (Agilent, Palo Alto, CA, USA).

Preparation of INNA-004 and Pam2CysSK4 (INNA-005)

Pam2Cys-SK4 (INNA-005) was obtained from Invivo-Gen and has the structure shown below.

Pam2Cys-SK4 (INNA-005):

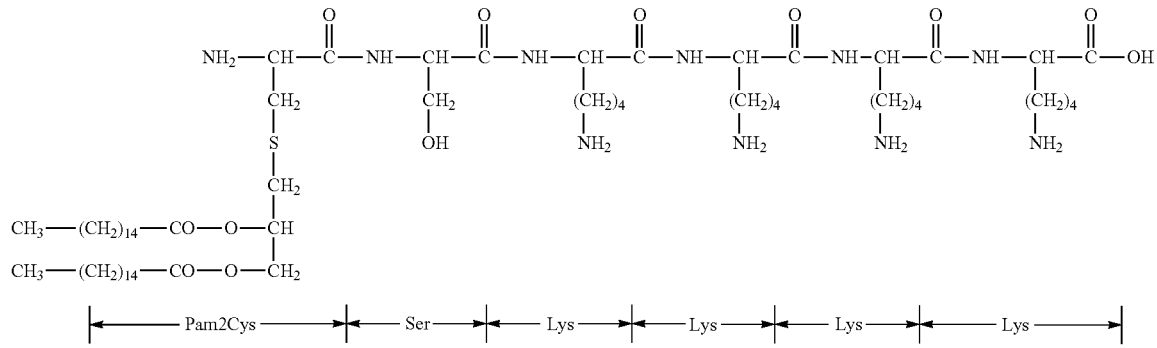

In the case of INNA-004 (see below) two serine residues are coupled seriatim following addition of 4 Lysine residues and in the case of Pam2Cys-SK4 a single serine is incorporated following addition of the 4 Lysine residues.

INNA-004:

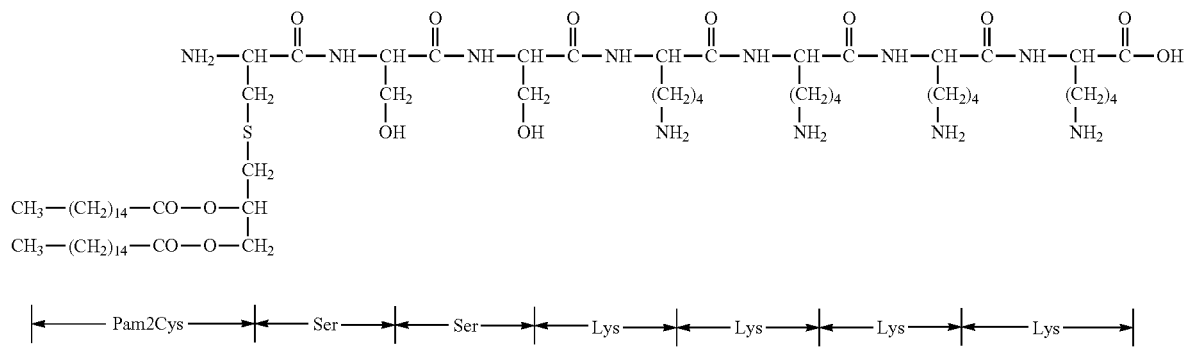

Synthesis of Pam$_3$Cys-Ser-PEG3000

To a polystyrene-polyoxyethylene graft copolymer (TentaGel PAP; Rapp Polymere GmbH, Tubingen, Germany) was coupled Fmoc-Ser(tBu)—OH. Pam3Cys was then coupled to this structure as described previously (Zeng, W. et al., *J. Immunol.* 2002. 169: 4905-12). Cleavage of the PEG-lipopeptide-conjugate was performed by treating the solid support with Reagent B which comprises of triisopropylsilane, phenol, water and TFA in a ratio of 20, 50, 50 and 880. The conjugate solutions was filtered from the resin, precipitated in chilled diethylether and purified by repeated precipitation from diethylether. PEG3000 refers to the molecular weight not the number of ethylene oxide units.

A schematic representation of the solid phase synthesis of Pam$_3$Cys-Ser-PEG3000 is shown below:

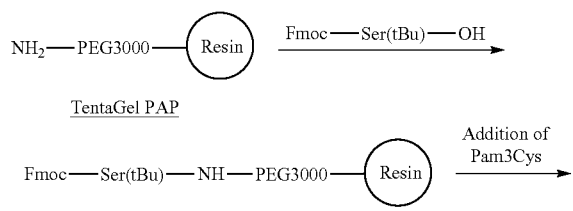

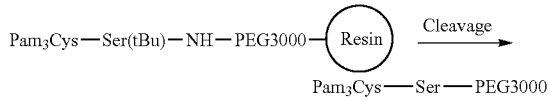

The Pam3Cys-Ser-PEG3000 preparation was readily soluble in water. LC-MS analysis of the material showed a single major peak with an average mass of 3,900 Da (expected mass 3,977 Da).

Amino acid analysis (AAA) was used to determine the content of the Pam3Cys-Ser-PEG3000 preparation. There are two amino acid residues in Pam$_3$Cys-Ser-PEG3000, cysteine and serine. The serine residue is the only one capable of detection by AAA because the cysteine residue is destroyed during the hydrolysis process. The content of Pam3Cys-Ser-PEG3000 was determined to be approximately 71%.

Preparation of compound (2) or Pam2Cys-Thr-PEG, a single threonine is incorporated following the addition of the PEG11 moiety. The addition of Pam2Cys (lipidation) was carried out as described above.

Preparation of compound (3) or Pam2Cys-homoSer-PEG, a single homo-serine is incorporated following the addition of the PEG11 moiety. The addition of Pam2Cys (lipidation) was carried out as described above.

Preparation of compound (4) or Pam2Cys-phosphoSer-PEG, a single phosphoserine is incorporated following the addition of the PEG11 moiety. The addition of Pam2Cys (lipidation) was carried out as described above.

Preparation of Pam2Cys-Ser-PEG3, PEG3 moiety instead of PEG11 was coupled following the coupling of the first amino acid glycine. After the coupling of a single serine residue the addition of Pam2Cys (lipidation) was carried out as described above.

Preparation Pam2Cys-Ser-PEG5, PEG5 instead of PEG11 moiety was coupled following the coupling of the first amino acid glycine. After the coupling of a single serine residue the addition of Pam2Cys (lipidation) was carried out as described above.

Preparation of compound (5), PEG27 instead of PEG11 moiety was coupled following the coupling of the first amino acid glycine. After the coupling of a single serine residue the addition of Pam2Cys (lipidation) was carried out as described above Preparation of compound (6), PEG27 moiety was coupled sequentially twice following the coupling of the first amino acid glycine. After the coupling of a single serine residue the addition of Pam2Cys (lipidation) was carried out as described above.

Example 2—Activation of Human TLR2

The potency of the compounds as activators of human and mouse TLR-2s was tested in an in vitro assay. The assay assesses NF-kB activation in the HEKBlue-mTLR-2 cell line. These cells have been stably transfected with mouse TLR-2 and express TLR-1 and TLR-6 endogenously at sufficient levels to allow for fully-functional TLR-1/2 and TLR-2/6 activation.

Toll-Like Receptor 2 (TLR2) stimulation is tested by assessing NF-kB activation in the HEKBlue-hTLR2 cell line. These cells have been stably transfected with human TLR2 and express TLR1 and TLR6 endogenously at a level sufficient to allow for fully-functional TLR1/2 and TLR2/6 activation. The activity of the test articles are tested on human TLR2 as potential agonists. The test articles are evaluated at seven concentrations and compared to control ligands. These steps are performed in triplicate.

In these assays, INNA-006 was significantly more potent than INNA-003. Although INNA-005 activated human TLR2, it did not display significant efficacy in the functional assays described in the Examples below.

Agonist activity of compounds against Human TLR-2 In Vitro:

| Compound | TLR-2 Activation Activity (EC50, pM) |
|---|---|
| INNA-003 | 38 |
| Pam2CysSK4 (INNA-005) | 3.7 |
| INNA-006 | 7.7 |

Example 3—URT Virus Challenge

In these studies an upper respiratory tract (URT) influenza virus challenge model was utilised in mice, using a dose of infectious virus which will replicate in the URT and then progress to the lungs. The URT model has been used to determine which compounds can prevent replication and dissemination of influenza virus from the URT to the lungs.

Cytokine and chemokine profiles in the nasal turbinates, trachea, lungs and sera of animals following URT treatment with three doses or a single dose of INNA-003 or INNA-006 were also measured.

The cytokine profiles of mice which were pre-treated with three doses of INNA-003 or INNA-006 followed by challenge with Udorn virus were also measured. Pre-treatment with up to three doses of INNA-006 shows a major reduction in viral load in the lungs with no detectable change in any of the inflammatory cytokines measured.

Experimental Animals

Groups of 5 male or female, 6-8 week old C57BL/6 mice were used for all studies. After administration of saline, the compound or viral challenge, mice were monitored daily for weight changes, and behavioural or physical changes.

URT Administration of Compounds

Mice were anaesthetized by isoflurane inhalation and saline or various doses of the compounds, diluted in saline, were administered intranasally in a total volume of 10 µl using a pipettor. For the multi-treatment experiments mice received 3 doses of INNA-003 or INNA-006 every second day over a 5 day period.

Preparation of Influenza Virus

A/Udorn/307/72 (H3N2) influenza virus (ie. Udorn virus) was propagated in the allantoic cavity of 10 day-old embryonated hens' eggs. Eggs were inoculated with approximately $10^3$ pfu of virus in 0.1 ml of saline. After 2 days incubation at 35° C. the eggs were chilled at 4° C. and allantoic fluid harvested and clarified by centrifugation. Viral infectivity titre (pfu/mL) was determined by plaque assay as described below and aliquots of the allantoic fluid were stored at −80° C. until used.

URT Virus Challenge

Mice were anaesthetised with isofluorane and inoculated intranasally with 500 pfu of Udorn virus in 10 µl of saline, using a pipettor. On day 5 post-challenge the nasal turbinates, trachea and lung were harvested to assess viral loads.

Extraction and Preparation of Nasal Turbinates, Trachea and Lung Homogenates

Mice were killed by $CO_2$ asphyxiation 24 hours post-treatment or 5 days post-influenza challenge. Nasal turbinates, trachea and lungs from each mouse were collected in 1.5 mL of RPMI-1640 medium with antibiotics (100 ug/mL penicillin, 180 ug/mL streptomycin and 24 ug/mL gentamicin) and kept on ice until processed. Tissues were homogenised using a tissue homogeniser and the resulting organ homogenates then centrifuged at 2,000 rpm for 5 min to remove cell debris. Supernatants were collected and stored at −80° C. for subsequent measurements.

Assessment of Viral Titres

Titres of infectious Udorn virus were determined by plaque assay on confluent monolayers of Madin Darby canine kidney (MDCK) cells. Six-well tissue culture plates were seeded with $1.2 \times 10^6$ MDCK cells per well in 3 ml of RP10 (RPMI-1640 medium supplemented with 10% (v/v) heat inactivated FCS, 260 ug/mL glutamine, 200 ug/mL sodium pyruvate and antibiotics). After overnight incubation at 37° C. in 5% $CO_2$ confluent monolayers were washed with RPMI. Test supernatant,s serially diluted in RPMI with antibiotics, were added to duplicate wells of monolayers. After incubation at 37° C. in 5% $CO_2$ for 45 min, monolayers were overlaid with 3 mL of agarose overlay medium containing 0.9% agarose and 2 ug/mL trypsin-TPCK treated in Leibovitz L15 medium pH6.8 with glutamine and antibiotics. Plates were incubated for 3 days at 37° C. in 5% $CO_2$ and virus-mediated cell lysis then counted as plaques on the cell layer. The total organ viral titres (plaque forming units, PFU) for individual animals were then calculated.

Determination of Cytokine Levels in Nasal Turbinates, Trachea, Lungs and Sera

IFN-γ, IL-2, IL-4, TNF, IL-10, IL-6, KC, MCP-1, RANTES, IL-12/IL-23p40 and IL-17A present in nasal turbinates, trachea, lung homogenates and serum samples were measured using a BD Cytometric Bead Array (CBA) Flex Kit according to the manufacturer's instructions with the exception that a total of 0.15 µl of each capture bead suspension and 0.15 µl of each PE-detection reagent was used in each 50 µl sample. Samples were analysed using a Bection Dickinson FACSCanto II flow cytometer and the data analysed using FCAP Array multiplex software.

Statistical Analyses

A one-way analysis of variance (ANOVA) with Tukey comparison of all column tests was used. A two-way ANOVA with Bonferroni's test was used to compare the same treatment groups in the single and 3 repeat dose regimes. A p-value ≤0.0322 was considered statistically significant. Statistical analyses were performed using GraphPad Prism, version 7.0.

Example 4—Assessing the Effect of Pre-Treatment with Different Doses of INNA-003, Pam2Cys-SK4 or INNA-006 on the Outcome of URT Challenge with Udorn Virus This experiment was performed to determine the antiviral effect of URT pre-treatment with various doses of INNA-003, INNA-006 or Pam2Cys-Ser-K4.

On day 0 mice (5 animals/group) received either saline, 5 nmoles, 0.1 nmoles or 0.005 nmoles of INNA-003, Pam2Cys-SK4 or INNA-006, administered intranasally in 10 µl after being anaesthetized with isoflurane. On day 1 following administration with TLR2 agonist, mice were challenged intranasally with 500 pfu of Udorn virus in a volume of 10 µl after being anaesthetized with isoflurane. Mice were killed on day 5 and nasal turbinates trachea and lungs were removed, homogenised and frozen for subsequent analyses.

The experimental design is summarised in FIG. 20.

Figure 1:
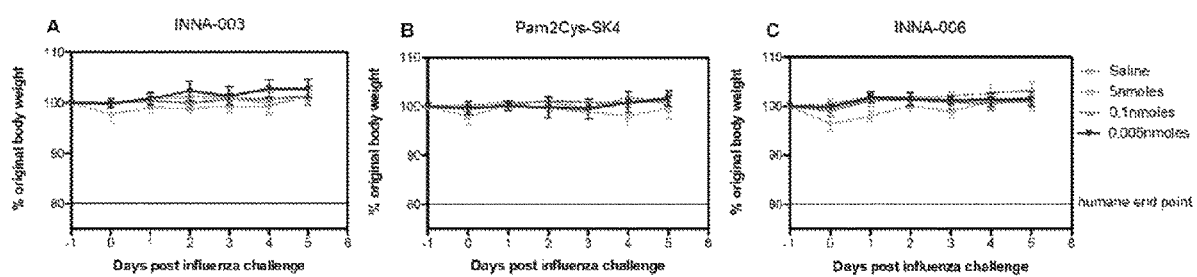
FIG. 1: Percentage change in body weight of mice receiving URT treatment with the different TLR2 agonists. Groups of C57BL/6 mice (n=5) were inoculated intranasally with various doses of (A) INNA-003, (B) Pam2Cys-SK4 or (C) INNA-006 in 10 µl of saline while anaesthetised. After 24 hours, mice were anaesthetized and challenged intranasally with 500 pfu of A/Udorn/307/72 (H3N2) influenza virus (ie. Udorn virus) in 10 µl of saline. Error bars depict s.d. and the horizontal line at 80% represents the limit of weight loss i.e. 20% acceptable according to the AEC.

Relative to baseline, there was little or no weight loss in C57BL/6 mice treated with INNA-003, Pam2Cys-SK4 or INNA-006 in the dose range 0.005 nmoles-5 nmoles (FIG. 1). Body weights returned to normal over a period of 1-2 days.

Figure 2:
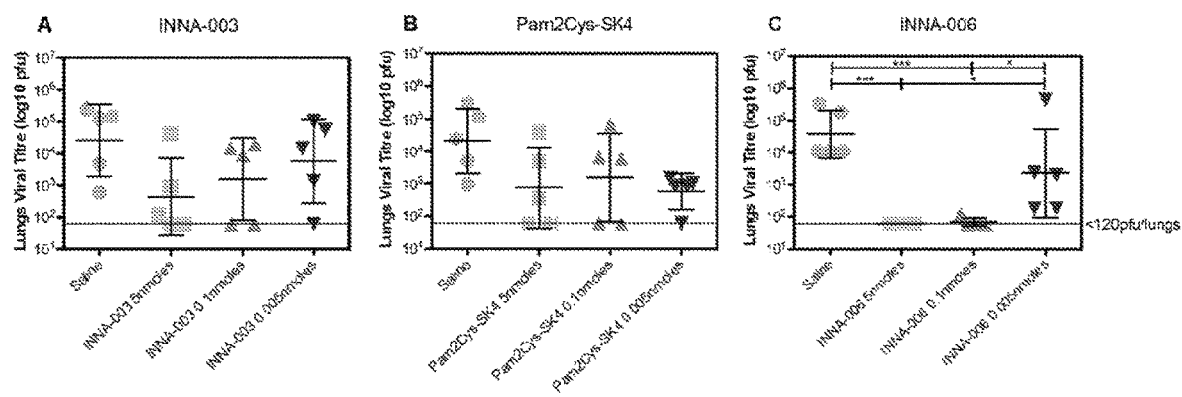
FIG. 2: Prophylactic URT treatment with TLR2 agonists prior to URT challenge with Udorn virus. Groups of C57BL/6 mice (5 animals per group) were inoculated intranasally with different doses of (A) INNA-003, (B) Pam2Cys-SK4 or (C) INNA-006 in 10 µl of saline while anaesthetised. After 24 hours, mice were anaesthetized by isoflurane inhalation and challenged intranasally with 500 pfu of Udorn influenza virus in 10 µl of saline. Viral titers in the lungs were determined by plaque formation in MDCK cell monolayers 5 days after viral challenge. Error bars depict s.d. and statistical significance (\*\*\*P=0.0002 & \*P=0.0322) were obtained using a one-way ANOVA with Tukey comparing all columns within a test.

At doses of 5 nmoles and 0.1 nmoles of INNA-006, progression of influenza virus to the lungs was significantly inhibited in mice treated 1 day prior to viral challenge (FIG. 2). Mice receiving 0.005, 0.1 or 5 nmoles of INNA-003 or Pam2Cys-SK4, or 0.005 nmoles of INNA-006 displayed partial inhibition of influenza virus progression to the lungs. Influenza virus titres in the nasal turbinates of all mice were ~100-fold higher than the titre of the challenge dose confirming successful viral challenge using the URT model (data not shown).

These results showed that a compound where a single serine separates Pam2Cys and PEG has the most potent effect at inhibiting viral progression. As shown in the Figures, INNA-006 is 10-100 times more effective than INNA-003 or Pam2Cys-SK4 at inhibiting viral progression.

Example 5—Assessing the Progression of Udorn Virus to the Lower Respiratory Tract of C57BL/6 Mice Following URT Challenge with 500 Pfu of Udorn Virus Using Groups with Larger (n=10) Numbers of Mice This experiment compares the effect on viral progression to the lungs of mice pre-treated with varying doses of INNA-003 and INNA-006 following challenge with Udorn virus.

On day 0, mice (10 animals/group) received either saline, 5 nmoles, 0.5 nmoles, or 0.05 nmoles of INNA-006 or 0.5 nmoles or 0.05 nmoles of INNA-003 administered intranasally in a 10 µl volume after being anaesthetised with isoflurane. On day 1 following administration of the TLR2 agonists, mice were challenged intranasally with 500 pfu of Udorn virus in a 10 µl volume after being anaesthetised with isoflurane. Mice were killed on day 5 and nasal turbinates and lungs were removed, homogenised and frozen for subsequent examination.

The experimental design is summarised in FIG. 20.

Again little weight loss was observed in mice treated with INNA-003 or INNA-006 in the dose range 0.05 nmoles-5 nmoles (FIG. 3).

At doses of 5 nmoles and 0.5 nmoles of INNA-006, progression of influenza virus to the lungs was significantly inhibited in mice treated 1 day prior to viral challenge (FIG. 4). Mice receiving 0.5 nmoles of INNA-003 or 0.05 nmoles of INNA-006 displayed partial inhibition of influenza virus progression to the lungs. Little or no apparent inhibition of virus titre was apparent in the treatment group receiving 0.05 nmoles INNA-003.

The presence of influenza virus in the nasal turbinates of mice was also assessed (data not shown). All mice except a single animal which received 5 nmoles of INNA-006 had detectable levels of virus in their nasal turbinates. The particular mouse with little or no virus in its nasal turbinates also had no detectable virus in its lungs. The cause of this is not known.

Example 6—Assessing Effects of Multiple Doses of TLR2 Agonists when Administered to the URT The treatment protocol for this study is summarised in Table 1. Groups of 5 female C57BL/6 mice received either 3 treatment doses or a single treatment dose of INNA-003 or INNA-006 at 2 different concentrations. All treatments were administered to the URT of anaesthetised mice in 10 µl volumes. Mice were weighed daily and one day after the final treatment, animals were killed and blood, nasal turbinates, trachea and lungs harvested, homogenised and assayed for cytokine content.

TABLE 1

Inoculation protocol to assess the effect of multiple doses of INNA-003 and INNA-006 measured by weight loss and cytokine profiles.

| Group | Treatment | Number of doses | Day(s) inoculum administered | Day of Tissue Harvest |
|---|---|---|---|---|
| 1 | Saline | 3 | Days 0, 2, 4 | Day 5 |
| 2 | INNA-003 0.5 nmoles | 3 | Days 0, 2, 4 | Day 5 |
| 3 | INNA-003 0.05 nmoles | 3 | Days 0, 2, 4 | Day 5 |
| 4 | INNA-006 0.5 nmoles | 3 | Days 0, 2, 4 | Day 5 |
| 5 | INNA-006 0.05 nmoles | 3 | Days 0, 2, 4 | Day 5 |
| 6 | Saline | 1 | Day 4 | Day 5 |
| 7 | INNA-003 0.5 nmoles | 1 | Day 4 | Day 5 |

TABLE 1-continued

Inoculation protocol to assess the effect of multiple doses of INNA-003 and INNA-006 measured by weight loss and cytokine profiles.

| Group | Treatment | Number of doses | Day(s) inoculum administered | Day of Tissue Harvest |
|---|---|---|---|---|
| 8 | INNA-003 0.05 nmoles | 1 | Day 4 | Day 5 |
| 9 | INNA-006 0.5 nmoles | 1 | Day 4 | Day 5 |
| 10 | INNA-006 0.05 nmoles | 1 | Day 4 | Day 5 |

The experimental design is summarised in FIG. 21.

Relative to baseline, there was no significant weight loss apparent in C57BL/6 mice following URT treatment with either a single dose or 3 consecutive doses of INNA-003 or INNA-006 at concentrations of 0.05 nmoles or 0.5 nmoles (FIG. 5). The greatest weight loss, 1.89%±1.15%, was observed following the first of 3 repeated doses of 0.5 nmoles INNA-003.

FIGS. 6, 7 and 8 shows the cytokine/chemokine profiles that were detected in the nasal turbinates, lungs, trachea and sera of mice following either a single or 3 repeat doses (0.5 nmoles or 0.05 nmoles) of INNA-003 or INNA-006. The cytokine/chemokine profiles detected in lungs, trachea and sera showed no discernible differences when compared between groups of animals treated with either single or triple dose regimes. Differences in the cytokine/chemokine profiles were observed in nasal turbinates (FIGS. 6 and 7) with an increase in proinflammatory cytokines and chemokines including IL-6, KC & MCP-1. These increases were detected in a dose-dependent manner for both INNA-003 and INNA-006 when compared to saline control treatment (FIGS. 6 and 7). Mice treated with a single dose of INNA-006 (0.5 nmoles) showed increased RANTES secretion in the nasal turbinates when compared to animals that received INNA-003.

Mice that were treated with 3 repeat doses of either INNA-006 or INNA-003 showed a marked decrease in cytokine/chemokine levels in the nasal turbinates, lungs and sera when compared to mice that had received a single dose of either compound (FIG. 8).

Statistically significant increases of IL-6, and KC levels were apparent in the nasal turbinates of mice treated with agonist compared with those treated with saline but these increases were significantly less in animals receiving multiple treatments (FIG. 8). For example, the level of IL-6 was approximately 25-fold lower in the nasal turbinates of mice treated with 3 doses (0.5 nmoles) of either INNA-003 or INNA-006 (~22 pg/ml and 15 pg/ml respectively) when compared to levels detected in mice that received a single dose of the same compound. In mice receiving a single dose (0.5 nmoles) of agonist, there was an approximately 125-fold (530 pg/ml: 4 pg/ml) increase in IL-6 levels with 0.5 nmoles INNA-003 and a 98-fold increase (~395 pg/ml: ~4 pg/ml) with INNA-006.

A statistically significant difference was detected in the levels of KC present in nasal turbinates of mice that received a single treatment of TLR2 agonist viz, a 2-fold increase for animals receiving 0.5 nmoles INNA-003 (~76 pg/ml: 27 pg/ml) and INNA-006 (~83 pgml: ~27 pg/ml) with no statistically significanct difference observed between the 3 dose treatment groups receiving 3 doses of TLR2 agonist or saline.

There was no significance of KC in the lungs of mice treated with either INNA-003 or INNA-006 after a single dose compared to the saline control (FIG. 8). However a statistical significance was apparent in the levels of KC in lungs of mice treated with the 3-dose regime (FIG. 13); both 0.5 and 0.05 nmole doses of INNA-006 produced a moderate 2fold increase of KC secretion in lungs compared to INNA-003 (~14 pg/ml:7.5 pg/ml) and a 3fold increase compared to the saline control treatments (~14 pg/ml:~5 pg/ml).

There was a statistically significant, 2-fold reduction, of KC levels in the lung when treated with 3 doses of INNA-003 when compared to INNA-006 treatment (~7.5 pg/ml: ~16.3 pg/ml)).

The effect of administering multiple doses of INNA-003 or INNA-006 to the URT of mice treated with 3 doses of 0.5 nmoles of compound administered 2 days apart showed no significant weight losses or any obvious physical or behavioural changes. When these mice were challenged with influenza virus one day after the third dose, significant reduction in dissemination of virus to lungs was observed in animals treated with 3 doses of 0.5 nmoles of INNA-006.

Example 7—Effect of Multiple Doses of INNA-003 or INNA-006 Followed by Challenge with Influenza Virus on Body Weight and Lung Virus Titres The treatment and challenge protocol for this study is summarised in Table 2. Groups of 5 C57BL/6 mice were treated with 3 doses of either saline, INNA-003 or INNA-006. One day after the third dose mice were challenged with influenza virus and 5 days later lungs were collected for determination of viral titres. Levels of selected cytokines were also measured in nasal turbinates and lungs of these animals.

TABLE 2

Inoculation protocol to assess the anti-viral efficacy of multiple doses of INNA-003 and INNA-006.

| Group | Treatment | Number of doses | Day(s) inoculum is administered* | Day of URT challenge with 500pfu Udorn virus^ |
|---|---|---|---|---|
| 1 | Saline | 3 | Days 0, 2, 4 | Day 5 |
| 2 | INNA-003 0.5 nmoles | 3 | Days 0, 2, 4 | Day 5 |
| 3 | INNA-006 0.5 nmoles | 3 | Days 0, 2, 4 | Day 5 |

The experimental design is summarised in FIG. 22.

Relative to baseline, there was no statistically significant weight loss in mice treated with 0.5 nmoles of INNA-003 or INNA-006 (FIG. 9).

Following three repeated doses of 0.5 nmoles of INNA-006, progression of influenza virus to the lungs was significantly inhibited compared to animals which received saline. Mice receiving three doses of 0.5 nmoles of INNA-003 displayed partial inhibition of influenza virus progression to the lungs (FIG. 10). As shown in FIG. 10, INNA-006 is about 10-100 times more effective than INNA-003 at inhibiting viral progression.

The amounts of influenza virus in the nasal turbinates of mice was also determined (data not shown) to demonstrate that all animals had increased levels of virus (approximately 20 fold increase) in the nasal turbinates indicating successful introduction and subsequent replication of virus.

Example 8—TLR2 Activation by Various Compounds

Comparison of the abilities of various compounds to stimulate luciferase activity in an NF-κB cell-based reporter system was determined. Compounds tested include INNA-006 (or compound (1)); INNA-013 (or compound (4)); INNA-014 (or compound (3)); INNA-015 (or compound (2)); INNA-010; INNA-011 (or compound (5)); INNA-012 (or compound (6)); and INNA-009. HEK293T cells, transiently co-transfected with a human TLR2 plasmid and a luciferase-NF-κB plasmid reporter system, were exposed to various dilutions of each compound. Successful receptor binding and subsequent signal transduction events were determined by measuring the luminescence due to luciferase activity (results shown in FIG. 11—left to right columns for each concentration are in the following order INNA-006 (or compound (1)); INNA-013 (or compound (4)); INNA-014 (or compound (3)); INNA-015 (or compound (2)); INNA-010; INNA-011 (or compound (5)); INNA-012 (or compound (6)); and INNA-009.

The results demonstrate that the most potent compounds were those with a single serine, threonine or homoserine separating the Pam2Cys and PEG, or a length of 12, 28, or two groups of 28, ethylene oxide monomers. However, all compounds resulted in successful receptor binding and subsequent signal transduction.

Example 9—Comparison of INNA-006 and Pam3Cys-Ser-PEG3000 Using an In Vitro Luciferase Assay Comparison of the in vitro TLR2 agonistic activity of Pam3Cys-Ser-PEG3000 and INNA-006: HEK293T cells, transiently co-transfected with a human TLR2 plasmid and a luciferase-NF-κB plasmid reporter system, were exposed to various dilutions of INNA-006 or Pam3Cys-Ser-PEG3000.

Successful receptor binding and subsequent signal transduction events were determined by measuring the luminescence due to luciferase activity (FIG. 12). The results demonstrate that Pam3Cys-Ser-PEG3000 is inferior to INNA-006 in its ability to signal NF-κB in the dose range tested (12.2 pM to 3.125 pM).

Example 10—TLR Binding and Specificity

INNA-006 was assessed for its ability to activate a range of other TLR pattern recognition receptors. These assessments were conducted using both human and mouse TLR panels. These assays detect a secreted embryonic alkaline phosphatase (SEAP) reporter under the control of a promoter which is inducible by NF-κB activation in HEK293 cells.

The secreted embryonic alkaline phosphatase (SEAP) reporter is under the control of a promoter inducible by the transcription factor NF-κB. This reporter gene allows the monitoring of signaling through the TLR, based on the activation of NF-κB. In a 96-well plate (200 μL total volume) containing the appropriate cells (50,000-75,000 cells/well), 20 μL of the test article or the positive control ligand is added to the wells. The media added to the wells is designed for the detection of NF-κB induced SEAP expression. After a 16-24 hr incubation the optical density (OD) is read at 650 nm on a Molecular Devices SpectraMax 340PC absorbance detector.
Control Ligands
    hTLR2: HKLM (heat-killed *Listeria monocytogenes*) at 1×108 cells/mL
    hTLR3: Poly(I:C) HMW at 1 μg/mL
    hTLR4: *E. coli* K12 LPS at 100 ng/mL
    hTLR5: *S. typhimurium* flagellin at 100 ng/mL
    hTLR7: CL307 at 1 μg/mL
    hTLR8: CL075 at 1 μg/mL
    hTLR9: CpG ODN2006 at 1 μg/mL.

Under the conditions tested, it was confirmed that INNA-006 was able to activate its proposed target (TLR-2) and showed no activation of any other TLR tested in these assays (FIG. 13).

Example 11—Assessing the Effect of Pre-Treatment with INNA-011 on the Outcome of Challenge with Udorn Virus The effect on viral replication of treatment with 5 nmoles of INNA-011 7 days prior to influenza challenge with 500 pfu of Udorn virus was investigated. On day 0, mice (10 animals/group) received either saline or 5 nmoles of INNA-011 administered intranasally in a volume of 10 μl while anaesthetised.

On day 7 following administration of INNA-011, mice were challenged intranasally with 500 pfu Udorn virus in a volume of 10 μl while anaesthetised. Mice were killed 5 days after challenge with virus and nasal turbinates, trachea and lungs were removed, homogenised and supernatants frozen for subsequent determination of viral titres.

Little or no weight loss was apparent in C57BL/6 mice treated with INNA-011 using a dose of 5 nmoles (data not shown).

Mice treated on Day-7 with 5 nmoles INNA-011 were able to significantly inhibit progression of influenza virus to the lungs when compared to saline controls (FIG. 14).

Example 12—Synthesis of the R and S Isomers of INNA-006 and INNA-011, Around the Chiral Centre of 2,3-bis(palmitoyloxy)propyl R and S isomers of the Pam2 moiety of Fmoc S-2,3-di(palmitoyloxypropyl)-cysteine (Fmoc-Dpc) were purchased from Bachem Inc. which were then used to synthesise the R and S-Pam2 isomers of INNA-006 and INNA-011 as described in Example 1 above.

The synthesised compounds were characterised using HPLC, mass spectrometry and amino acid analysis (AAA). The stereochemistry of the compounds was determined by measuring their optical activity using standard methods in the art.

Example 13—Comparison of the In Vitro Agonist Activity of the R-Pam2, L-Cys Diastereomer and the S-Pam2, L-Cys Diastereomer of INNA-006 and INNA-011

Toll-Like Receptor 2 (TLR2) stimulation was tested by assessing N-kB activation in the HEK-Blue hTLR2 cell line. These cells have been stably transfected with human TLR2 and express TLR1 and TLR6 endogenously at a level sufficient to allow for fully-functional TLR1/2 and TLR2/6 activation. The activity of the test articles were tested on human TLR2 as potential agonists. The test articles were evaluated at seven concentrations and compared to control ligands (see list below). These steps were performed in triplicate.
Control Ligands
    hTLR2 Dose Response:
    HKLM (heat-killed *Listeria monocytogenes*) at:
    1×108, 2.5×107, 6.3×106, 1.6×106, 3.9×105, 9.8×104 and 2.4×104 cells/mL TLR-Control Cell Line HEK293/Null1 Dose Response:

TNFα at 1,000, 250, 62.5, 15.6, 3.9, 0.98 and 0.24 ng/mL

Test Articles and Materials

| | |
|---|---|
| Article 2: | INNA-006.04 (R-Pam2, L-Cys diastereomer) |
| Stock Concentration: | 5 mg/mL |
| Storage Condition: | 4° C. |
| Final Concentrations: | 500, 125, 31.3, 7.8, 1.9, 0.5, 0.12 pg/mL |
| Article 3: | INNA-006.05 (S-Pam2, L-Cys diastereomer) |
| Stock Concentration: | 5 mg/mL |
| Storage Condition: | 4° C. |
| Final Concentrations: | 500, 125, 31.3, 7.8, 1.9, 0.5, 0.12 pg/mL |
| Article 4: | 20% INNA-006.04 (R-Pam2, L-Cys diastereomer) and 80% INNA-006.05 (S-Pam2, L-Cys diastereomer) |
| Stock Concentration: | 5 mg/mL |
| Storage Condition: | 4° C. |
| Final Concentrations: | 500, 125, 31.3, 7.8, 1.9, 0.5, 0.12 pg/mL |
| Article 5: | 50% INNA-006.04 (R-Pam2, L-Cys diastereomer) and 50% INNA-006.05 (S-Pam2, L-Cys diastereomer) |
| Stock Concentration: | 5 mg/mL |
| Storage Condition: | 4° C. |
| Final Concentrations: | 500, 125, 31.3, 7.8, 1.9, 0.5, 0.12 pg/mL |
| Article 6: | 80% INNA-006.04 (R-Pam2, L-Cys diatereomer) and 20% INNA-006.05 (S-Pam2, L-Cys diastereomer) |
| Stock Concentration: | 5 mg/mL |
| Storage Condition: | 4° C. |
| Final Concentrations: | 500, 125, 31.3, 7.8, 1.9, 0.5, 0.12 pg/mL |
| Article 8: | INNA-011.03 (R-Pam2, L-Cys diastereomer) |
| Stock Concentration: | 5 mg/mL |
| Storage Condition: | 4° C. |
| Final Concentrations: | 500, 125, 31.3, 7.8, 1.9, 0.5, 0.12 pg/mL |
| Article 9: | INNA-011.04 (S-Pam2, L-Cys diatereomer) |
| Stock Concentration: | 5 mg/mL |
| Storage Condition: | 4° C. |
| Final Concentrations: | 500, 125, 31.3, 7.8, 1.9, 0.5, 0.12 pg/mL |
| Article 10: | 20% INNA-011.03 (R-Pam2, L-Cys diastereomer) and 80% INNA-011.04 (S-Pam2, L-Cys diastereomer) |
| Stock Concentration: | 5 mg/mL |
| Storage Condition: | 4° C. |
| Final Concentrations: | 500, 125, 31.3, 7.8, 1.9, 0.5, 0.12 pg/mL |
| Article 11: | 50% INNA-011.03 (R-Pam2, L-Cys diastereomer) and 50% INNA-011.04 (S-Pam2, L-Cys diastereomer) |
| Stock Concentration: | 5 mg/mL |
| Storage Condition: | 4° C. |
| Final Concentrations: | 500, 125, 31.3, 7.8, 1.9, 0.5, 0.12 pg/mL |
| Article 12: | 80% INNA-011.03 (R-Pam2, L-Cys diastereomer) and 20% INNA-011.04 (S-Pam2, L-Cys diastereomer) |
| Stock Concentration: | 5 mg/mL |
| Storage Condition: | 4° C. |
| Final Concentrations: | 500, 125, 31.3, 7.8, 1.9, 0.5, 0.12 pg/mL |

Preparation of Test Articles

Test articles 2, 3, 8 and 9 were prepared as follows:

Each article was provided as 5 mg of dry powder and resuspended in 1 mL of sterile, endotoxin-free for a 5 mg/mL solution.

A series of five 1:10 serial dilutions are performed by mixing 20 μL of the previous highest dilution, starting with the 5 mg/mL stock, with 180 μL sterile, endotoxin-free water. The concentration of the fifth dilution is 50 ng/mL From the 50 ng/mL solution, make a 5 ng/mL solution by mixing 80 μL of the 50 ng/mL with 720 μL sterile, endotoxin-free water.

Follow by preparing six 1:4 dilutions by mixing 60 μL of the previous highest dilution with 180 μL sterile, endotoxin-free water.

Test articles 4, 5, 6, 10, 11 and 13 were prepared as follows:

Using the previously prepared 5 ng/mL solutions of articles 2, 3, 8, and 9, six solutions consisting of the following ratios were prepared. The final volume of each solution is 200 μL.

Article 4 consists of 20% Article 2 and 80% Article 3
Article 5 consists of 50% Article 2 and 50% Article 3
Article 6 consists of 80% Article 2 and 20% Article 3
Article 10 consists of 20% Article 8 and 80% Article 9
Article 11 consists of 50% Article 8 and 50% Article 9
Article 13 consists of 80% Article 8 and 20% Article 9

Using the newly prepared 5 ng/mL solutions, six 1:4 dilutions are prepared by mixing 60 μL of the previous highest dilution with 180 μL sterile, endotoxin-free water.

General Procedure

The secreted embryonic alkaline phosphatase (SEAP) reporter is under the control of a promoter inducible by the transcription factor NF-κB. This reporter gene allows the monitoring of signaling through the TLR, based on the activation of NF-κB. In a 96-well plate (200 μL total volume) containing the appropriate cells (50,000-75,000 cells/well), 20 μL of the test article or the positive control ligand is added to the wells. The media added to the wells is designed for the detection of NF-κB induced SEAP expression. After a 20 hour incubation the optical density (OD) is read at 650 nm on a Molecular Devices SpectraMax 340PC absorbance detector.

Results

Human TLR2 Dose Response:

Results are provided as optical density values (650 nm) and shown in FIGS. 15, 16 and 17. As shown in the Figures, the R-Pam2, L-Cys diastereomer (R, L-diastereomer) of INNA-006 and INNA-011 is significantly more active than the S-Pam2, L-Cys diastereomer (S, L diastereomer). However, the S-Pam2, L-Cys diastereomer (S, L diastereomer) is still potent.

Example 14—Synthesis of INNA-006 and INNA-011 Analogues

General Synthesis Protocol for Assembly of INNA-011 Analoques:

Reagents: The solid phase support, TentaGel S RAM resin (substitution factor 0.24 mmol/g; Rapp Polymere, Tubingen, Germany) was used throughout with glycine coupled to the solid phase support as the first residue (see below). The amino acid derivatives: Fmoc-Gly-OH, Fmoc-Ser(tBu)—OH and Fmoc-N-Me-Cys(Trt)-OH were btained from Auspep or Merck. Fmoc-NH—(PEG)$_{27}$-COOH (88 atoms) was from Merck (Cat #851033, Darmstadt, Germany). Borane-dimethylamine-complex (abbreviated as ABC) was from Sigma-Aldrich (cat #180238-5G). 16% (w/v) formaldehyde (methanol free) was from Pierce (cat #28906) or alternatively a 16% methanol-free solution of paraformaldehyde was obtained from from Electron Microscopy Sciences (cat #15710). The sources of other materials are indicated in the Appendices.

Acylation: A 4-fold molar excess of Fmoc amino acid, 0-benzotriazole-N,N,N',N'-tetramethyl-uroniumhexafluorophosphate (HBTU) and a 6-fold molar excess of diisopropylethylamine (DIPEA) were used in all acylation steps. All acylation reactions were carried out for 60 minutes or as indicated in each individual step and completion of reaction confirmed by trinitrobenezene sulfonic acid (TNBSA) test. Removal of the Fmoc protective group from α-amino groups was achieved by exposing the solid phase support to 2.5% diazabicyclo[5.4.0]undec-7-ene (DBU; Sigma, Steinheim, Germany) for 2×5 minutes. Dimethylformamide (DMF; Auspep, Melbourne, Australia) was used to wash the solid phase support between each acylation and de-protection steps. The coupling of Fmoc-NH—(PEG)$_{27}$-COOH was carried out in the same way as the coupling of amino acids.

Synthesis of Fmoc-PEG27-Gly-Resin

Fmoc-Gly (297 mg, 1 mmole in 4 ml of DMF) was added as the first amino acid to the solid support (0.5 g, 0.125 mmole), followed by coupling of Fmoc-NH-PEG$_{27}$-COOH (300 mg, 0.194 mmole; 0.237 mmole of HBTU, 0.26 mmole of HOBT and 0.36 mmole of DIPEA in 2 ml of DMF) for 2 hrs. After washing, equal portions (0.0425 mmole) of the solid phase support, to which was attached Fmoc-NH-PEG27-Gly, was used to assemble the four different analogues as described below.

Addition of Pam2Cys

Synthesis of S-(2,3-dihydroxypropyl)cysteine: Triethylamine (6 g, 8.2 ml, 58 mmoles) was added to L-cysteine hydrochloride (3 g, 19 mmole) and 3-bromo-propan-1,2-diol (4.2 g, 2.36 ml, 27 mmole) in water and the solution held at room temperature for 3 days. The solution was reduced in vacuo at 40° C. to a white residue which was then precipitated with acetone (300 ml) and the precipitate isolated by centrifugation. The precipitate was washed twice with acetone and dried to yield S-(2,3-dihydroxypropyl)cysteine as a white amorphous powder.

Synthesis of N-Fluorenylmethoxycarbonyl-S-(2,3-dihydroxypropyl)-cysteine (Fmoc-Dhc-OH): S-(2,3-dihydroxypropyl) cysteine (2.45 g, 12.6 mmole) was dissolved in 9% sodium carbonate (20 ml). A solution of fluorenylmethoxycarbonyl-N-hydroxysuccinimide (3.45 g, 10.5 mmole) in acetonitrile (20 ml) was then added and the mixture stirred for 2 h, diluted with water (240 ml) and extracted with diethyl ether (25 ml×3). The aqueous phase was acidified to pH2 with concentrated hydrochloric acid and then extracted with ethyl acetate (70 ml×3). The extract was washed with water (50 ml×2) and saturated sodium chloride solution (50 ml×2). The extract was dried over anhydrous sodium sulphate and evaporated to dryness. The final product was obtained by applying high vacuum to remove residual solvent.

Coupling of Fmoc-Dhc-OH to resin-bound peptide: Fmoc-Dhc-OH (100 mg, 0.24 mmole) was activated in DCM and DMF (1:1, v/v, 3 mL) with HOBt (36 mg, 0.24 mmole) and DICl (37 uL, 0.24 mmole) at 0° C. for 5 min. The mixture was then added to a vessel containing the resin-bound peptide (0.04 mmole, 0.25 g amino-peptide resin). After shaking for 2 h the solution was removed by filtration on a glass sinter funnel (porosity 3) and the resin washed with DCM and DMF (3×30 mL). The reaction was monitored for completion using the TNBSA test. If necessary a double coupling was performed.

Palmitoylation of the two hydroxyl groups of the Fmoc-Dhc-peptide resin: Palmitic acid (204 mg, 0.8 mmole), DIPCDl (154 uL, 1 mmole) and DMAP (9.76 mg, 0.08 mmole) were dissolved in 2 mL of DCM and 1 mL of DMF. The resin-bound Fmoc-Dhc-peptide resin (0.04 mmole, 0.25 g) was suspended in this solution and shaken for 16 h at room_temperature. The supernatant was removed by filtration and the resin thoroughly washed with DCM and_DMF to remove any residue of urea. The removal of the Fmoc group was accomplished using 2.5% DBU (2×5 min).

Cleavage of peptide from the solid support: The solid support bearing the assembled lipopeptide was exposed to reagent B (93% TFA, 5% water and 2% triisopropylsilane) for two hours. NB the peptide will not precipitate in chilled ether. Most of the TFA must be removed and the residue is then dissolved in 50% acetonitrile and purified immediately or freeze-dried.

Purification and characterisation: Following cleavage from the solid support, each of the analogues were purified by reversed-phase HPLC using a C4 Vydac column (10 mm×250 mm; Alltech, NSW, Australia) installed in a Waters HPLC system (Waters Millipore, Milford, MA, USA). Identification of the target materials were determined by mass spectrometry and the purified material was then characterised by analytical HPLC using a VYDAC C8 column (4.6 mm×250 mm) and found to be greater than 95%. Mass analysis was carried out using an Agilent 1100 Series LC/MSD ion-trap mass spectrometer (Agilent, Palo Alto, CA, USA).

Synthesis of N-acetyl-INNA-011

Synthesis of N-acetyl-INNA-011 was carried out by acetylation of the amino group of cysteine residue of Pam2Cys with the peptide still attached to the solid phase as set out in the below schematic. Cleavage from the solid support and purification yielded the final product.

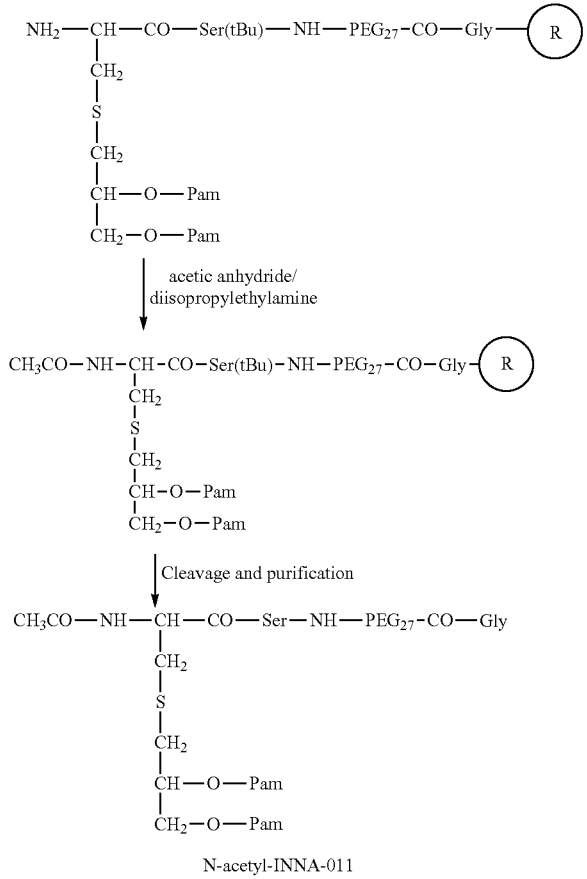

N-acetyl-INNA-011

Following the removal of Fmoc group, 220 mg (0.5 mmole) of N-Fluorenylmethoxycarbonyl-S-(2,3-dihydroxypropyl)-cysteine (Fmoc-Dhc-OH), 67 mg of HOBt and 200 μl of DICl in 2 ml of DMF were added to one of the portions of Fmoc-NH-PEG$_{27}$-Gly-resin made as described above and the reaction was held at RT for 3 hrs. The two hydroxyl groups were palmitoylated as described above. The Fmoc group was removed and the exposed α-amino group acetylated by incubation with 1 ml of acetylanhydride and 100 µl of DIPEA for 30 mins. The peptide was cleaved from the solid support and purified as described below. The qualitative analysis of the purified final product was carried out by amino acid analysis (AAA) and LC-MS analysis.

Synthesis of N-methyl-INNA-011 and L-Homo-cysteine-INNA-006

The synthesis of N-methyl-INNA-011 was carried out using a protocol for synthesis of Pam2Cys-containing peptides as described in the below schematic. Briefly, Fmoc-N-methyl-Cys(Trt)-OH was coupled to Ser(tBu)-NH-PEG27-Gly which was attached to the solid support. The primary α-amino group was then blocked with a tert-butyloxycarbonyl (Boc) group. The subsequent removal of the protecting trityl group and alkylation of the sulfhydryl group with 1-bromo-2,3-propanediol followed by palmitoylation of the two vicinal hydroxyl groups yielded N-methyl-INNA-011.

The Trt group was removed by immersing the peptide resin in an iodine solution (254 mg of iodine in 8 ml of DMF) pre-chilled in a salt-ice bath for 5 mins. The whole peptide-resin and iodine suspension was kept on ice-salt for 1 hr. The peptide resin was washed in a glass sinter funnel with saturated ascorbic acid until the the peptide resin was colourless and then further washed with DMF. The peptide was then treated with dithiolthreitol (154 mg in 1.5 ml of DMF plus 0.5 ml of 0.2M phosphate buffer at pH8) for 1 hr at RT. Following thorough washing with DMF the exposed sulfhydryl group was alkylated by suspending the peptide resin in 200 µl of 1-bromo-2,2-propanediol and 10 µl of DIPEA in 1 ml of DMF for 3 hrs. The final palmitoylation of the two hydroxy groups was carried out as described above. The peptide was cleaved from the solid support and purified as described below. The qualitative analysis of the purified final product was carried out by AAA and LC-MS analysis.

L-Homo-cysteine-INNA-006 was synthesised by using Fmoc-homoCys(Trt)-OH and Ser(tBu)-NH-PEG11-Gly in the above method.

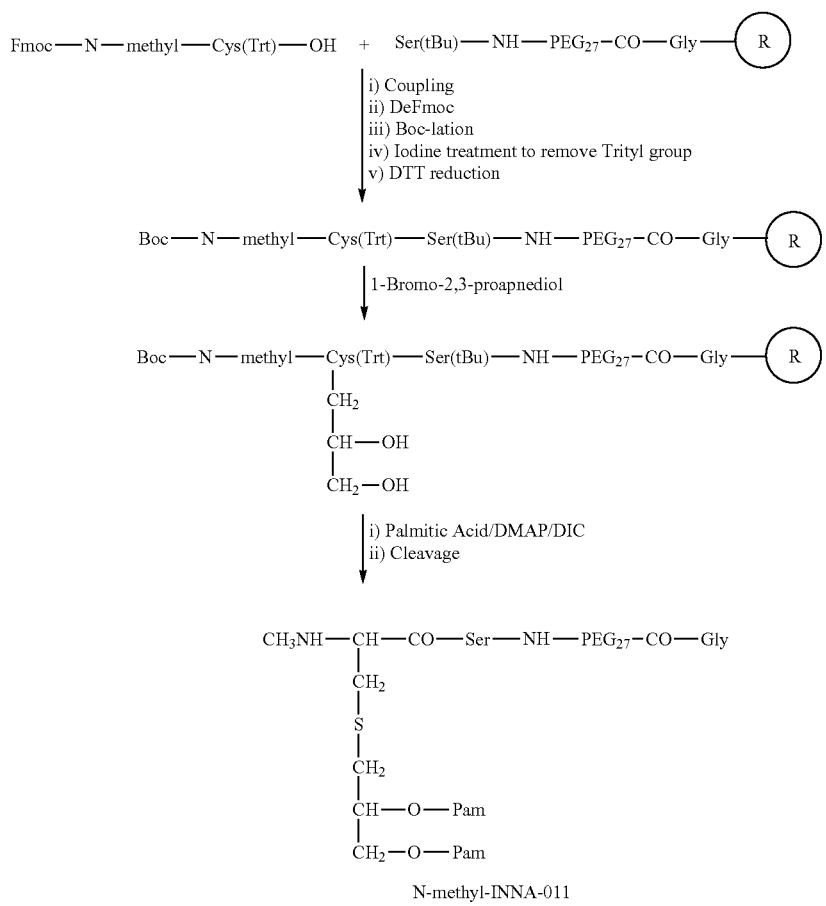

To one of the portions of Fmoc-NH-PEG$_{27}$-COOH was added Fmoc-N-methyl-Cys(Trt)-OH (102 mg, 0.17 mmole, 65 mg of HBTU, 23 mg of HOBt and 46 µl of DIPEA in 2 ml of DMF) for 2 hr. The Fmoc-group was removed and the exposed primary amino group then blocked with di-tert-butyl-dicarbonate (1 ml plus 100 µl of DIPEA) overnight.

Synthesis of N,N-dimethyl-INNA-011

N,N-dimethyl-INNA-011 was prepared by reductive methylation of the primary alpha-amino group of Pam$_2$Cys present in INNA-011 in the presence of formaldehyde and borane-dimethylamine-complex (ABC) as set out in the below schematic.

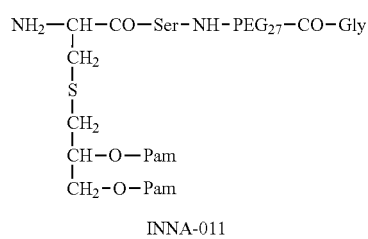

INNA-011

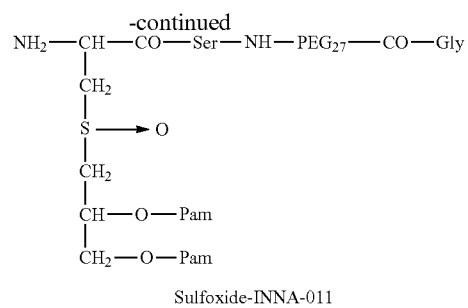

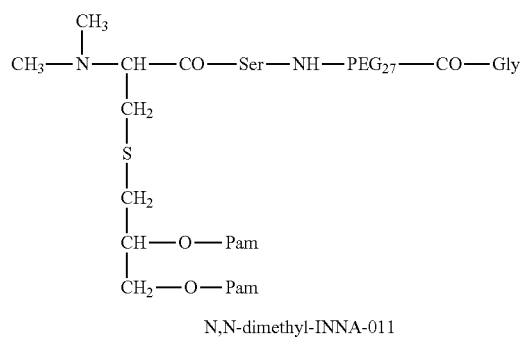

N,N-dimethyl-INNA-011

A solution of borane-dimethylamine complex, ABC (220 mg in 1 ml of water, 3.3 M) was freshly made. To 5 mg of INNA-011 was added 1 ml of 3.3M solution of ABC followed by addition, 3 times, of 187 µl 16% formaldehyde solution (NB. this reaction is strongly exothermic). The reaction was left at RT for 3 hrs. An additional 187 µl of 16% formaldehyde solution was then added and incubated at RT for 1 hr. LC-MS analysis indicated that reaction was complete. The product was isolated by semipreparative HPLC. Qualitative analysis of the purified product was carried out by LC-MS and amino acid analysis.

Synthesis of Sulfoxide-INNA-011

Sulfoxide-INNA-011 was prepared by oxidising INNA-011 in the presence of hydrogen peroxide as set out in the below schematic. Briefly, INNA-011 was dissolved in water and to it was added an equal volume of 30% hydrogen peroxide. The reaction was held at RT overnight (16 hrs). The majority of the final product was sulfoxide-INNA-011 with a very small amount of sulfone-INNA-011. These two oxidation products were easily separated by HPLC.

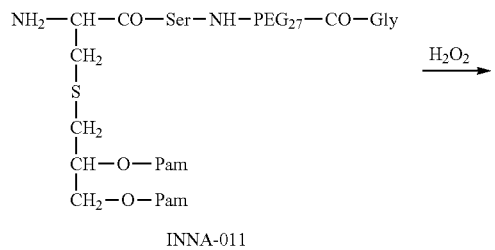

INNA-011

Sulfoxide-INNA-011

To 10 mg of INNA-011 dissolved in 300 µl of water was added 300 µl of 30% hydrogen peroxide (Sigma-Aldrich) and the reaction was held at RT overnight. LC-MS analysis indicated a completed reaction and the final product was isolated by semipreparative HPLC. Quality analysis of the purified product was carried out by AAA and LC-MS.

Peptide Quantitation

Quantitation of the four analogues of INNA-011 was done by amino acid analysis performed in vacuo by hydrolysis of samples at 110° C. in sealed glass vials in the presence of 6N HCl containing 0.1% phenol. Derivatisation of amino acids was then carried out using Waters AccQTag reagents according to the manufacturer's instructions followed by analysis on a Waters Acquity UPLC System (Waters Millipore) using an AccQTag ultra column (2.1 mm×100 mm; Waters Millipore).

Determination of Biological Activity In Vitro

NF-kB reporter gene assay: HEK293T cells were cultured in 96-well plates at $4 \times 10^4$ cells per well and transfected 24 h later with 100 ng of an NF-kB luciferase reporter gene, 50 ng of TK-Renilla-luciferase expressing plasmid (Promega corporation, Madison, USA) with or without 5 ng TLR2-expressing plasmid in the presence of 0.8 µl Fugene 6 (Roche Diagnostic) was then added to each well. Lipopeptides are added to the wells 24 h later at a series of concentrations as indicated in each graph. Cell lysates were prepared 5 h after stimulation using reporter lysis buffer (Promega Corporation, Madison, USA). Luciferase activities in the cell lysates were determined using a reagent kit (Promega Corporation, Madison, USA) and a FLUOstar microplate reader by BMG Labtech, Ortenberg, Germany. The NF-kB-dependent firefly luciferase activity is normalised with NF-kB-independent renilla luciferase activity. The relative stimulation was calculated as the ratio of the stimulated to non-stimulated samples.

Comparison of the abilities of N-acetyl-, N-methyl-, N,N-dimethyl and sulfoxide-INNA-011, and INNA-011 to stimulate luciferase activity in an NF-κB cell-based reporter system is shown in FIG. 18. All modifications still retained potent activity, with only small variations in potency.

N-methyl-INNA-006 stimulated luciferase activity in an NF-κB cell-based reporter system to a similar level as INNA-006 (data not shown). N-methyl-INNA-006 retained potent activity, with only a small reduction in potency relative to INNA-006.

Example 15

Biophysical Characterisation

INNA-011 and INNA-006 form micelle-type aggregates in both aqueous and organic solutions. The size distribution and polydispersity of particles of INNA-006 and INNA-011 were determined by dynamic light scattering (DLS) and size exclusion chromatography (University of Melbourne). Size exclusion chromatography analysis suggests that in saline solution both INNA-006 and INNA-011 aggregate in a micelle formation as a single uniform species. INNA-011 however demonstrated a more uniform distribution of particle sizes at all concentrations as examined by DLS.

INNA-006

Using size exclusion chromatography and LC-MS analysis, it was determined that INNA-006 at 0.3 mg/ml is present in PBS solution as a single uniform species with a Stokes radius of ~6.3 nm and a molecular weight of ~377,000. This corresponds to the assembly in a micelle formation of about 266 individual INNA-006 molecules.

As the concentration of INNA-006 is increased, material with a particle size centered on a radius of ~7 nm accumulates within 2 hours of the sample preparation as measured by DLS. This accumulation starts at a concentration of ~16 $\mu$M, (0.02 mg/ml, represents the 0.16 nmole/10 $\mu$l curve) and is clearly discernable at 125 $\mu$M (0.17 mg/ml, represents the 1.25 nmole/10 $\mu$l curve) and above. Other species are apparent within the data set at both smaller and at larger radii and may reflect the establishment of various equilibria between monomer and higher order complexes which approach a more stable equilibrium with particle size distribution stabilising around 7 nm.

INNA-011

Using size exclusion chromatography and LC-MS analysis, it was determined that INNA-011 at 0.4 mg/ml is present in saline solution as a single uniform species with a Stoke's radius of ~7.3 nm and a molecular weight of ~566,000. This corresponds to the assembly in a micelle formation of about 267 individual INNA-011 molecules.

INNA-011 demonstrated a uniform distribution of particle sizes at all concentrations examined (ranging from 2 mM to 8 $\mu$M in PBS (represents the 20 –0.08 nmole/10 $\mu$l)), within 2 hours of sample preparation and at 3 days after storage at ambient temperatures (Data not shown). At the concentrations of 2 mM to 8 pM particle sizes (7.4-7.7 nm) were larger than that observed with INNA-006 and additional species outside of this main sequence were more ordered and less dominant.

Off-Target Activity

INNA-006 and INNA-011 were subjected to assessment in the Eurofins SafetyScreen44 assay. This profiling panel provides early identification of significant off-target interactions for the optimization of safety margins.

At 1 $\mu$M INNA-011 and INNA-006 do not show any off-target effect in the Eurofins SafetyScreen44 (as determined by less than 10% inhibition against tested targets). NB: 1 $\mu$M is 200,000 time the $EC_{50}$ for INNA-006 and 50,000 time the $EC_{50}$ for INNA-011 as determined using InvivoGen's in vitro assay.

In Vitro Cross Species Plasma Stability Study

The in vitro plasma stability of INNA-006 and INNA-011 in rat, dog and human plasma was determined at 37° C. over a 4 h time course.

INNA-006 exhibited a half-life of: rat (5.7 h), dog (8.9 h) and the human half-life could not be calculated due to insufficient degradation during the course of the experiment.

INNA-011 exhibited a half-life of: rat (5.9 h) and both dog and the human half-life could not be calculated due to insufficient degradation during the course of the experiment.

Thus, both INNA-006 and INNA-011 displayed a marginally better correlation of plasma stability between dog and human plasma than between rat and human plasma stability.

In Vitro Cross Species Hepatocyte Stability Study

The in vitro intrinsic clearance of INNA-006 and INNA-011 was determined at 0.5 $\mu$M in rat, dog, cynomolgus monkey and human hepatocytes at 37° C.

INNA-006 exhibits low $Cl_{int}$ (<2 $\mu$L/min/million cells) across all species with a half-life of >375 min determined for rat, dog, monkey and human.

INNA-011 also exhibits low $Cl_{int}$ (2 $\mu$L/min/million cells or lower) across all species, however is marginally less stable than INNA-006 with half-lives of: rat (>375 min), dog (284 min), monkey (173 min) and human (328 min) determined.

This data is consistent with either poor cellular penetration of both compounds and/or high metabolic stability.

The invention claimed is:

1. A compound selected from the group consisting of:

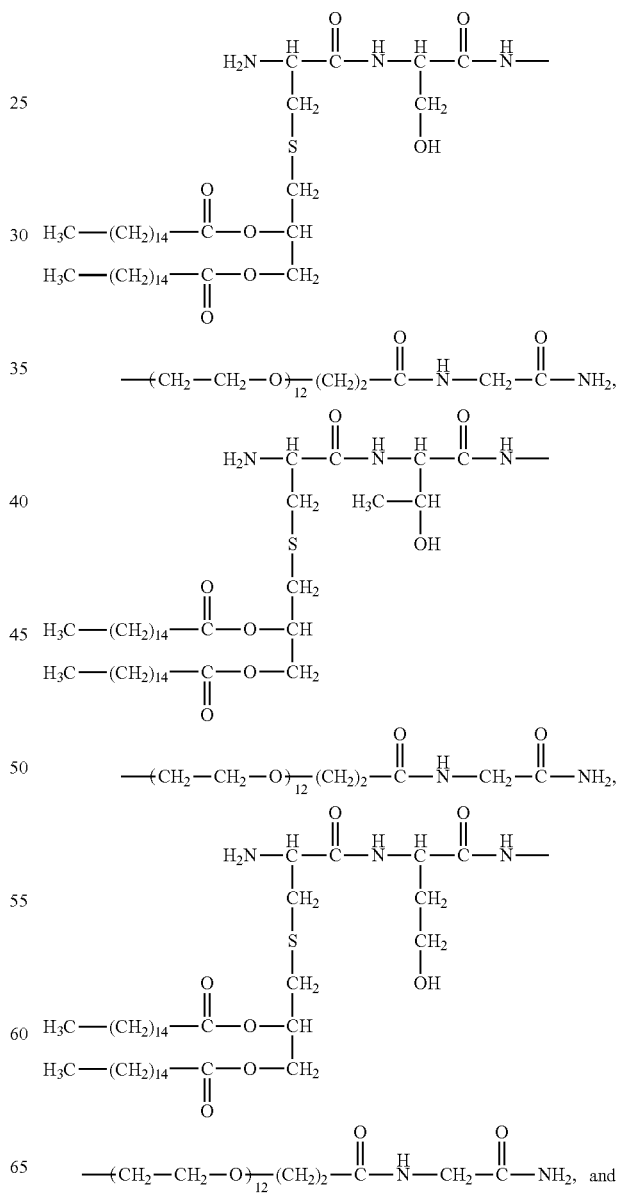

-continued
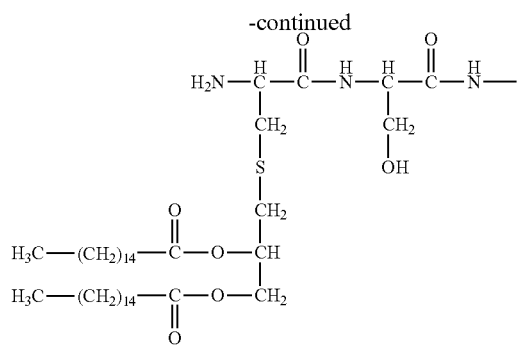
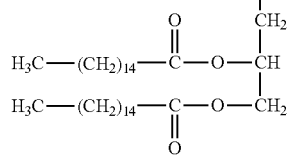
or a pharmaceutically acceptable salt thereof.
2. The compound according to claim 1, wherein the compound is:
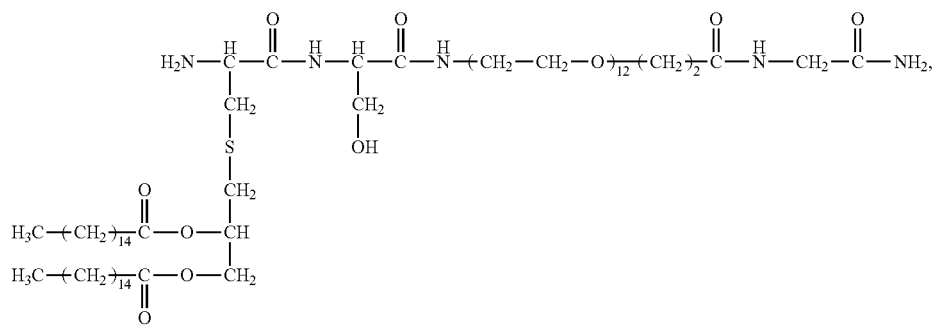 [SMILES: CCC(=O)OCC(CSCC(N)C(=O)NC(CO)C(=O)NCCOCC(=O)NCC(N)=O)OC(=O)CC]
or a pharmaceutically acceptable salt thereof.
3. The compound according to claim 1, wherein the compound is:
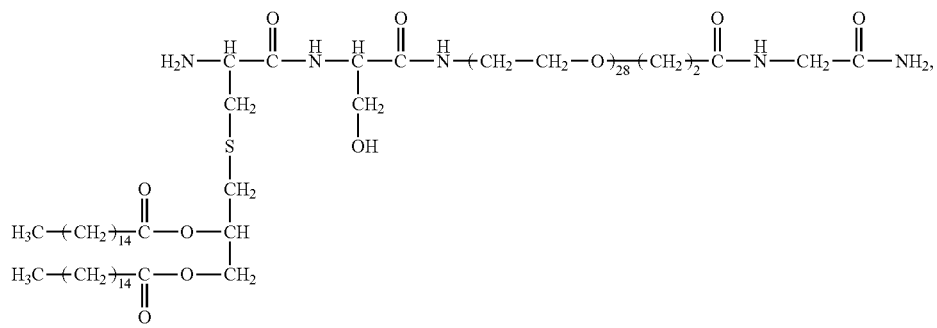 [SMILES: CCC(=O)OCC(CSCC(N)C(=O)NC(CO)C(=O)NCCOCC(=O)NCC(N)=O)OC(=O)CC]
or a pharmaceutically acceptable salt thereof.

4. A compound:
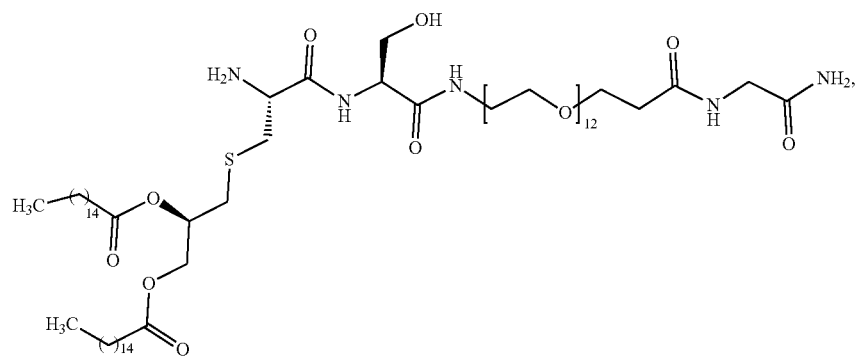
or a pharmaceutically acceptable salt thereof.
5. A compound:
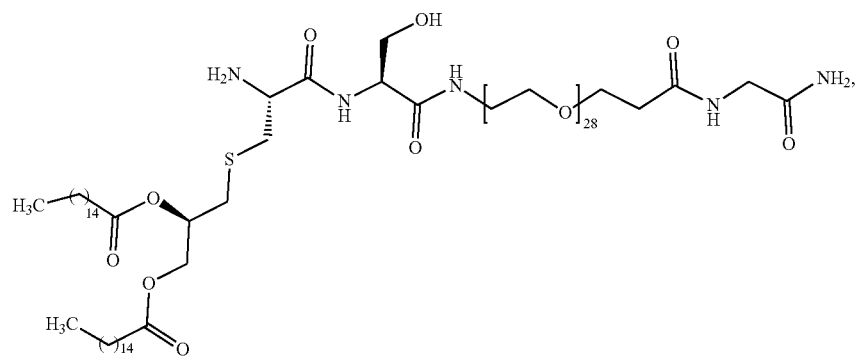
or a pharmaceutically acceptable salt thereof.
* * * * *

UNITED STATES PATENT AND TRADEMARK OFFICE
CERTIFICATE OF CORRECTION

| | | |
|---|---|---|
| PATENT NO. | : 12,195,557 B2 | Page 1 of 1 |
| APPLICATION NO. | : 16/768341 | |
| DATED | : January 14, 2025 | |
| INVENTOR(S) | : David Jackson et al. | |

It is certified that error appears in the above-identified patent and that said Letters Patent is hereby corrected as shown below:

In the Claims

Column 135, Claim number 1, Line number 20, recites, in part:
"–$(CH_2\text{-}CH_2\text{-}O)_{26}$-"

Which should recite:
"–$(CH_2\text{-}CH_2\text{-}O)_{28}$-"

Signed and Sealed this
Twenty-fourth Day of June, 2025

Coke Morgan Stewart
*Acting Director of the United States Patent and Trademark Office*